(12) United States Patent
Mylari

(10) Patent No.: US 6,849,629 B2
(45) Date of Patent: Feb. 1, 2005

(54) PYRIDAZINONE ALDOSE REDUCTASE INHIBITORS

(75) Inventor: Banavara L. Mylari, Waterford, CT (US)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 10/370,895

(22) Filed: Feb. 20, 2003

(65) Prior Publication Data

US 2003/0162784 A1 Aug. 28, 2003

Related U.S. Application Data

(62) Division of application No. 10/104,664, filed on Mar. 21, 2002, now Pat. No. 6,579,879.
(60) Provisional application No. 60/280,051, filed on Mar. 30, 2001.

(51) Int. Cl.[7] .................... A61K 31/506; C07D 403/12
(52) U.S. Cl. ........................ 514/252.01; 514/252.04; 514/252.05; 514/252.06; 544/238
(58) Field of Search .................... 544/238; 514/252.01, 514/252.04, 252.05, 252.06

(56) References Cited

U.S. PATENT DOCUMENTS

| | | | |
|---|---|---|---|
| 4,251,528 A | 2/1981 | Brittain et al. | 424/250 |
| 4,939,140 A | 7/1990 | Larson et al. | 514/222 |
| 4,996,204 A | 2/1991 | Mylari et al. | 514/248 |
| 5,675,023 A | 10/1997 | Igarashi et al. | 549/400 |
| 5,834,466 A | 11/1998 | Ramasamy et al. | 514/227.5 |
| 6,218,409 B1 | 4/2001 | Ikeda et al. | 514/342 |
| 6,579,879 B2 * | 6/2003 | Mylari | 514/252.01 |

FOREIGN PATENT DOCUMENTS

| | | | |
|---|---|---|---|
| FR | 2647676 | 6/1989 | A61K/31/50 |
| WO | WO 9217446 | 10/1992 | |
| WO | WO 9915523 | 4/1999 | C07D/407/14 |
| WO | WO 0287584 | 11/2002 | A61K/31/50 |
| WO | 2003057691 | * 7/2003 | |

OTHER PUBLICATIONS

Petric et al. Chemical Abstracts, vol. 84, No. 74205b (1976).*
Mylari et al. J. Med. Chem. vol. 46, p. 228302286 (2003).*
Medicinal Chemistry (3rd. Ed.) by Alfred Burger, p. 64–72 (1970).*

* cited by examiner

Primary Examiner—Richard L. Raymond
(74) Attorney, Agent, or Firm—Peter C. Richardson; Gregg C. Benson; Carl J. Goddard

(57) ABSTRACT

The present invention relates to novel pyridazinone compounds, pharmaceutical compositions comprising those compounds and to methods of using such compounds and compositions to inhibit aldose reductase, lower sorbitol levels and, thus, lower fructose levels, and/or treat or prevent diabetic complications such as diabetic neuropathy, diabetic retinopathy, diabetic nephropathy, diabetic cardiomyopathy, diabetic microangiopathy and diabetic macroangiopathy in mammals. This invention also relates to methods of affording cardioprotection to subjects not suffering from diabetes. This invention also relates to pharmaceutical compositions and kits comprising a combination of an aldose reductase inhibitor (ARI) of this invention and a sorbitol dehydrogenase inhibitor and to methods of using such compositions or kits to treat or prevent the above diabetic complications in mammals. This invention also relates to other combinations with the ARIs of this invention, including combinations with adenosine agonists; NHE-1 inhibitors; glycogen phosphorylase inhibitors; selective serotonin reuptake inhibitors; GABA agonists; antihypertensive agents; 3-hydroxy-3-methylglutaryl coenzyme A reductase inhibitors; phosphodiesterase-5 inhibitors; and to glucose lowering agents.

52 Claims, No Drawings

PYRIDAZINONE ALDOSE REDUCTASE INHIBITORS

CROSS-REFERENCE TO RELATED APPLICATIONS

This application is a divisional under 35 U.S.C. §121 of U.S. application Ser. No. 10/104,664, filed Mar. 21, 2002, now U.S. Pat. No. 6,579,879, issued Jun. 17, 2003, which claims priority to U.S. Provisional Application Ser. No. 60/280,051, filed Mar. 30, 2001.

FIELD OF THE INVENTION

The present invention relates to novel sulfonyl pyridazinone compounds, pharmaceutical compositions comprising those compounds and to methods of using such compounds and compositions to inhibit aldose reductase, lower sorbitol levels and, thus, lower fructose levels, and/or treat or prevent diabetic complications such as diabetic neuropathy, diabetic retinopathy, diabetic nephropathy, diabetic cardiomyopathy, diabetic microangiopathy and diabetic macroangiopathy in mammals. This invention also relates to pharmaceutical compositions and kits comprising a combination of an aldose reductase inhibitor (ARI) of Formula I herein and a sorbitol dehydrogenase inhibitor and to methods of using such compositions or kits to treat or prevent the above diabetic complications in mammals. This invention also relates to other combinations with the ARIs of Formula I, including combinations with NHE-1 inhibitors; adenosine agonists; glycogen phosphorylase inhibitors (GPIs); selective serotonin reuptake inhibitors (SSRIs); γ-amino-butyric acid (GABA) agonists; antihypertensive agents; 3-hydroxy-3-methylglutaryl coenzyme A reductase inhibitors (vastatins); phosphodiesterase-5 (PDE5) inhibitors; and to glucose lowering compounds. This invention also relates to pharmaceutical compositions and kits comprising such combinations and to methods of using such compositions and kits to treat or prevent the aforesaid diabetic complications. This invention also relates to novel compounds that are useful as intermediates for preparing the sulfonyl pyridazinone compounds of this invention.

BACKGROUND OF THE INVENTION

The enzyme aldose reductase is involved in regulating the reduction of aldoses, such as glucose and galactose, to their corresponding polyols, such as sorbitol and galactitol. Sulfonyl pyridazinone compounds of Formula I of this invention, prodrugs of such compounds and pharmaceutically acceptable salts of such compounds and prodrugs, are useful as aldose reductase inhibitors in the treatment and prevention of diabetic complications of humans and other mammals associated with increased polyol levels in certain tissues (e.g., nerve, kidney, lens and retina tissue) of affected humans and other mammals.

French Patent Publication No. 2647676 discloses pyridazinone derivatives having substituted benzyl side chains and benzothiazole side chains described as being inhibitors of aldose reductase.

U.S. Pat. No. 4,251,528 discloses various aromatic carbocyclic oxophthalazinyl acetic acid compounds, which are described as possessing aldose reductase inhibitory properties.

Commonly assigned U.S. Pat. No. 4,939,140 discloses heterocyclic oxophthalazinyl acetic acid compounds useful as aldose reductast inhibitors.

Commonly assigned U.S. Pat. No. 4,996,204 discloses pyridopyridazinone acetic acid compounds useful as aldose reductase inhibitors.

SUMMARY OF THE INVENTION

The present invention is directed to compounds of Formula I,

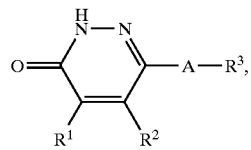

prodrugs thereof and pharmaceutically acceptable salts of said compounds and said prodrugs, wherein:

A is S, SO or $SO_2$;

$R^1$ and $R^2$ are each independently hydrogen or methyl;

$R^3$ is $Het^1$, —$CHR^4Het^1$ or $NR^6R^7$;

$R^4$ is hydrogen or $(C_1-C_3)$alkyl;

$R^6$ is $(C_1-C_6)$alkyl, aryl or $Het^2$;

$R^7$ is $Het^3$;

$Het^1$ is pyridyl, pyrimidyl, pyrazinyl, pyridazinyl, quinolyl, isoquinolyl, quinazolyl, quinoxalyl, phthalazinyl, cinnolinyl, naphthyridinyl, pteridinyl, pyrazinopyrazinyl, pyrazinopyridazinyl, pyrimidopyridazinyl, pyrimidopyrimidyl, pyridopyrimidyl, pyridopyrazinyl, pyridopyridazinyl, pyrrolyl, furanyl, thienyl, imidazolyl, oxazolyl, thiazolyl, pyrazolyl, isoxazolyl, isothiazolyl, triazolyl, oxadiazolyl, thiadiazolyl, tetrazolyl, indolyl, benzofuranyl, benzothienyl, benzimidazolyl, benzoxazolyl, benzothiazolyl, indazolyl, benzisoxazolyl, benzisothiazolyl, pyrrolopyridyl, furopyridyl, thienopyridyl, imidazolopyridyl, oxazolopyridyl, thiazolopyridyl, pyrazolopyridyl, isoxazolopyridyl, isothiazolopyridyl, pyrrolopyrimidyl, furopyrimidyl, thienopyrimidyl, imidazolopyrimidyl, oxazolopyrimidyl, thiazolopyrimidyl, pyrazolopyrimidyl, isoxazolopyrimidyl, isothiazolopyrimidyl, pyrrolopyrazinyl, furopyrazinyl, thienopyrazinyl, imidazolopyrazinyl, oxazolopyrazinyl, thiazolopyrazinyl, pyrazolopyrazinyl, isoxazolopyrazinyl, isothiazolopyrazinyl, pyrrolopyridazinyl, furopyridazinyl, thienopyridazinyl, imidazolopyridazinyl, oxazolopyridazinyl, thiazolopyridazinyl, pyrazolopyridazinyl, isoxazolopyridazinyl or isothiazolopyridazinyl; $Het^1$ is optionally substituted with up to a total of four substituents each independently selected from halo, formyl, $(C_1-C_6)$alkoxycarbonyl, $(C_1-C_6)$alkylenyloxycarbonyl, $(C_1-C_4)$alkoxy-$(C_1-C_4)$alkyl, $C(OH)R^{12}R^{13}$, $(C_1-C_4)$alkylcarbonylamido, $(C_3-C_7)$cycloalkylcarbonylamido, phenylcarbonylamido, benzyl, phenyl, naphthyl, imidazolyl, pyridyl, triazolyl, benzimidazolyl, oxazolyl, isoxazolyl, thiazolyl, oxadiazolyl, thiadiazolyl, tetrazolyl, thienyl, benzothiazolyl, pyrrolyl, pyrazolyl, quinolyl, isoquinolyl, benzoxazolyl, pyridazinyl, pyridyloxy, pyridylsulfonyl, furanyl, phenoxy, thiophenoxy, $(C_1-C_4)$alkylsulfenyl, $(C_1-C_4)$alkylsulfonyl, $(C_3-C_7)$cycloalkyl, $(C_1-C_6)$alkyl optionally substituted with up to three fluoro, or $(C_1-C_4)$alkoxy optionally substituted with up to five fluoro; said benzyl, phenyl, naphthyl, imidazolyl, pyridyl, triazolyl, benzimidazolyl, oxazolyl, isoxazolyl, thiazolyl, oxadiazolyl, thiadiazolyl, tetrazolyl, thienyl, benzothiazolyl, pyrrolyl, pyrazolyl, quinolyl, isoquinolyl, benzoxazolyl, pyridazinyl, pyridyloxy, pyridylsulfonyl, furanyl, phenoxy, thiophenoxy, in the definition of substituents for $Het^1$ are optionally substituted with up to three substituents independently selected from hydroxy, halo, hydroxy-$(C_1-C_4)$alkyl, $(C_1-C_4)$alkoxy-$(C_1-C_4)$alkyl, $(C_1-C_6)$alkylsulfenyl, $(C_1-C_6)$alkylsulfinyl, $(C_1-C_6)$alkylsulfonyl, $(C_1-C_6)$alkyl optionally substituted with up to five fluoro and $(C_1-C_6)$alkoxy optionally substituted with up to five fluoro; said imidazolyl, oxazolyl, isoxazolyl, thiazolyl and pyrazolyl in the definition of substituents for $Het^1$ are optionally substituted with up to two substituents independently selected from hydroxy, halo, $C_1-C_6$ alkyl, hydroxy-$(C_1-C_4)$alkyl, $(C_1-C_4)$alkoxy-$(C_1-C_4)$alkyl, $C_1-C_4$alkyl-phenyl optionally substituted in the phenyl portion with one Cl, Br, OMe, Me or $SO_2$-phenyl wherein said $SO_2$-phenyl is optionally substituted in the phenyl portion with one Cl, Br, OMe, Me, $(C_1-C_4)$alkyl optionally substituted with up to five fluoro, or $(C_1-C_4)$alkoxy optionally substituted with up to three fluoro;

$R^{12}$ and $R^{13}$ are each independently hydrogen or $(C_1-C_4)$ alkyl;

$Het^2$ and $Het^3$ are each independently imidazolyl, pyridyl, triazolyl, benzimidazolyl, oxazolyl, isoxazolyl, thiazolyl, oxadiazolyl, thiadiazolyl, tetrazolyl, thienyl, benzothiazolyl, pyrrolyl, pyrazolyl, quinolyl, isoquinolyl, benzoxazolyl, pyridazinyl, pyridyloxy, pyridylsulfonyl, furanyl, phenoxy, thiophenoxy; $Het^2$ and $Het^3$ are each independently optionally substituted with up to a total of four substituents each independently selected from halo, formyl, $(C_1-C_6)$ alkoxycarbonyl, $(C_1-C_6)$alkylenyloxycarbonyl, $(C_1-C_4)$alkoxy-$(C_1-C_4)$alkyl, $C(OH)R^{18}R^{19}$, $(C_1-C_4)$ alkylcarbonylamido, $(C_3-C_7)$ cycloalkylcarbonylamido, phenylcarbonylamido, phenyl, naphthyl, imidazolyl, pyridyl, triazolyl, benzimidazolyl, oxazolyl, isoxazolyl, thiazolyl, oxadiazolyl, thiadiazolyl, tetrazolyl, thienyl, benzothiazolyl, pyrrolyl, pyrazolyl, quinolyl, isoquinolyl, benzoxazolyl, pyridazinyl, pyridyloxy, pyridylsulfonyl, furanyl, phenoxy, thiophenoxy, $(C_1-C_4)$alkylsulfenyl, $(C_1-C_4)$alkylsulfonyl, $(C_3-C_7)$ cycloalkyl, $(C_1-C_4)$alkyl optionally substituted with up to three fluoro or $(C_1-C_4)$alkoxy optionally substituted with up to five fluoro; said phenyl, naphthyl, imidazolyl, pyridyl, triazolyl, benzimidazolyl, oxazolyl, isoxazolyl, thiazolyl, oxadiazolyl, thiadiazolyl, tetrazolyl, thienyl, benzothiazolyl, pyrrolyl, pyrazolyl, quinolyl, isoquinolyl, benzoxazolyl, pyridazinyl, pyridyloxy, pyridylsulfonyl, furanyl, phenoxy, thiophenoxy, in the definition of substituents for $Het^2$ and $Het^3$ are optionally substituted with up to three substituents independently selected from hydroxy, halo, hydroxy-$(C_1-C_4)$alkyl, $(C_1-C_4)$ alkoxy-$(C_1-C_4)$alkyl, $(C_1-C_4)$alkyl optionally substituted with up to five fluoro and $(C_1-C_4)$alkoxy optionally substituted with up to five fluoro; said imidazolyl, oxazolyl, isoxazolyl, thiazolyl and pyrazolyl in the definition of substituents for $Het^2$ and $Het^3$ are optionally substituted with up to two substituents independently selected from hydroxy, halo, hydroxy-$(C_1-C_4)$ alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to three fluoro; and $R^{18}$ and $R^{19}$ are each independently hydrogen or $(C_1-C_4)$alkyl, provided that when $R^3$ is $NR^6R^7$, then A is $SO_2$.

A preferred group of compounds, designated Group A, are those compounds of Formula I, prodrugs thereof and pharmaceutically acceptable salts of said compounds and said prodrugs, wherein A is $SO_2$; $R^1$ and $R^2$ are each hydrogen; $R^3$ is $Het^1$ optionally substituted with up to a total of four substituents.

A preferred group of compounds within Group A, designated Group B, are those compounds, prodrugs thereof and pharmaceutically acceptable salts of said compounds and said prodrugs, wherein $Het^1$ is 5H-furo-[3,2c]pyridin-4-one-2-yl, furano[2,3b]pyridin-2-yl, thieno[2,3b]pyridin-2-yl, indol-2-yl, indol-3-yl, benzofuran-2-yl, benzothien-2-yl, imidazo[1,2a]pyridin-3-yl, pyrrol-1-yl, imidazol-1-yl, indazol-1-yl, tetrahydroquinol-1-yl or tetrahydroindol-1-yl, wherein said $Het^1$ is optionally independently substituted with up to a total of two substituents each independently selected from fluoro, chloro, bromo, $(C_1-C_6)$alkyl, $(C_1-C_6)$ alkoxy, trifluoromethyl, hydroxy, benzyl or phenyl; said benzyl and phenyl are each optionally independently substituted with up to three halo, $(C_1-C_6)$alkyl, $(C_1-C_6)$alkoxy, $(C_1-C_6)$alkylsulfonyl, $(C_1-C_6)$alkylsulfinyl, $(C_1-C_6)$ alkylsulfenyl, trifluoromethyl or hydroxy.

A preferred group of compounds within Group B, designated Group C, are those compounds, prodrugs thereof and pharmaceutically acceptable salts of said compounds and said prodrugs, wherein $Het^1$ is indol-2-yl, benzofuran-2-yl, benzothiophen-2-yl, furano[2,3b]pyridin-2-yl, thieno[2,3b] pyridin-2-yl or imidazo[1,2a]pyridin-4-yl, wherein said $Het^1$ is optionally independently substituted with up to a total of two substituents independently selected from fluoro, chloro, bromo, $(C_1-C_6)$alkyl, $(C_1-C_6)$alkoxy, trifluoromethyl and phenyl; said phenyl being optionally substituted with up to two substituents independently selected from fluoro, chloro and $(C_1-C_6)$alkyl.

A preferred group of compounds within Group C, designated Group D, are those compounds, prodrugs thereof and pharmaceutically acceptable salts of said compounds and said prodrugs, wherein $Het^1$ is indol-2-yl or indol-3-yl, said indol-2-yl or indol-3-yl being optionally independently substituted with up to two substituents each independently selected from fluoro, chloro and methyl.

A preferred compound within Group D is the compound wherein $Het^1$ is 5-chloro-indol-2-yl, a prodrug thereof or a pharmaceutically acceptable salt of said compound or prodrug.

Another preferred compound within Group D is the compound wherein $Het^1$ is 5-fluoro-indol-2-yl, a prodrug thereof or a pharmaceutically acceptable salt of said compound or prodrug.

Another preferred compound within Group D is the compound wherein $Het^1$ is unsubstituted indol-2-yl, a prodrug thereof or a pharmaceutically acceptable salt of said compound or said prodrug.

Another preferred compound within Group D is the compound wherein wherein $Het^1$ is unsubstituted indol-3-yl, a prodrug thereof or a pharmaceutically acceptable salt of said compound or prodrug.

Another group of preferred compounds within Group C, designated Group E, are those compounds, prodrugs thereof and pharmaceutically acceptable salts of said compounds and said prodrugs, wherein $Het^1$ is benzofuran-2-yl optionally substituted with up to two substituents each independently selected from methyl, methoxy, chloro, fluoro, ethyl, 4-fluorophenyl, trifluoromethyl, isopropyl, phenyl and hydroxy.

A group of preferred compounds within Group E are those compounds, prodrugs thereof and pharmaceutically acceptable salts of said compounds and said prodrugs, wherein $Het^1$ is 5-chloro-benzofuran-2-yl, 5,7-dichloro-benzofuran-2-yl, benzofuran-2-yl, 5-chloro-3-methyl-benzofuran-2-yl, 5-fluoro-3-methyl-benzofuran-2-yl, 3-methyl-5-trifluoromethyl-benzofuran-2-yl, 5-chloro-3-phenyl-benzofuran-2-yl, 3-phenyl-benzofuran-2-yl, 3-(4-fluoro-phenyl)-benzofuran-2-yl, 5-chloro-benzofuran-2-yl and 3-ethyl-5-methyl-benzofuran-2-yl or 3-methyl-benzofuran-2-yl.

Another group of preferred compounds within Group E, designated Group F, are those compounds, prodrugs thereof and pharmaceutically acceptable salts of said compounds and said prodrugs wherein $Het^1$ is 3-methylbenzofuran-2-yl, optionally substituted with up to one additional substituent each independently selected from methyl, methoxy, chloro, fluoro, ethyl, 4-fluorophenyl, trifluoromethyl, isopropyl, phenyl and hydroxy.

A preferred compound within Group F is the compound wherein said additional substituent is 5-chloro, a prodrug thereof or a pharmaceutically acceptable salt of said compound or prodrug. The potassium salt of this compound is particularly preferred.

Another preferred compound within Group F is the compound wherein said additional substituent is 5-fluoro, a prodrug thereof or a pharmaceutically acceptable salt of said compound or prodrug.

Another preferred compound within Group F is the compound wherein said additional substituent is 5-trifluoromethyl, a prodrug thereof or a pharmaceutically acceptable salt of said compound or prodrug.

Another group of preferred compounds within Group C, designated Group G, are those compounds, prodrugs thereof and pharmaceutically acceptable salts of said compounds and said prodrugs, wherein $Het^1$ is benzothien-2-yl optionally substituted with up to two substituents each independently selected from methyl and chloro.

A preferred compound within Group G is the compound wherein $Het^1$ is benzothien-2-yl, a prodrug thereof or a pharmaceutically acceptable salt of said compound or prodrug.

Another preferred compound within Group G is the compound wherein $Het^1$ is 5-chloro-3-methylbenzothien-2-yl, a prodrug thereof or a pharmaceutically acceptable salt of said compound or prodrug.

Another preferred group of compounds of Formula I are those compounds, prodrugs thereof and pharmaceutically acceptable salts of said compounds and said prodrugs wherein A is $SO_2$ and $R^3$ is $CHR^4Het^1$, said $Het^1$ being optionally substituted with up to a total of four substituents each independently selected from halo, formyl, $(C_1-C_6)$alkoxycarbonyl, $(C_1-C_6)$alkylenyloxycarbonyl, $(C_1-C_4)$alkoxy-$(C_1-C_4)$alkyl, $C(OH)R^{12}R^{13}$, $(C_1-C_4)$alkylcarbonylamido, $(C_3-C_7)$cycloalkylcarbonylamido, phenylcarbonylamido, benzyl, phenyl, naphthyl, imidazolyl, pyridyl, triazolyl, benzimidazolyl, oxazolyl, isoxazolyl, thiazolyl, oxadiazolyl, thiadiazolyl, tetrazolyl, thienyl, benzothiazolyl, pyrrolyl, pyrazolyl, quinolyl, isoquinolyl, benzoxazolyl, pyridazinyl, pyridyloxy, pyridylsulfonyl, furanyl, phenoxy, thiophenoxy, $(C_1-C_4)$alkylsulfenyl, $(C_1-C_4)$alkylsulfonyl, $(C_3-C_7)$cycloalkyl, $(C_1-C_6)$alkyl optionally substituted with up to three fluoro, or $(C_1-C_4)$alkoxy optionally substituted with up to five fluoro; said benzyl, phenyl, naphthyl, imidazolyl, pyridyl, triazolyl, benzimidazolyl, oxazolyl, isoxazolyl, thiazolyl, oxadiazolyl, thiadiazolyl, tetrazolyl, thienyl, benzothiazolyl, pyrrolyl, pyrazolyl, quinolyl, isoquinolyl, benzoxazolyl, pyridazinyl, pyridyloxy, pyridylsulfonyl, furanyl, phenoxy, thiophenoxy, in the definition of substituents for $Het^1$ are optionally substituted with up to three substituents independently selected from hydroxy, halo, hydroxy-$(C_1-C_4)$alkyl, $(C_1-C_4)$alkoxy-$(C_1-C_4)$alkyl, $(C_1-C_6)$alkylsulfenyl, $(C_1-C_6)$alkylsulfinyl, $(C_1-C_6)$alkylsulfonyl, $(C_1-C_6)$alkyl optionally substituted with up to five fluoro and $(C_1-C_6)$ alkoxy optionally substituted with up to five fluoro; said imidazolyl, oxazolyl, isoxazolyl, thiazolyl and pyrazolyl in the definition of substituents for $Het^1$ are optionally substituted with up to two substituents independently selected from hydroxy, halo, $C_1-C_6$)alkyl, hydroxy-$(C_1-C_4)$alkyl, $(C_1-C_4)$alkoxy-$(C_1-C_4)$alkyl, $C_1-C_4$)alkyl-phenyl optionally substituted in the phenyl portion with one Cl, Br, OMe, Me or $SO_2$-phenyl wherein said $SO_2$-phenyl is optionally substituted in the phenyl portion with one Cl, Br, OMe, Me, $(C_1-C_4)$alkyl optionally substituted with up to five fluoro, or $(C_1-C_4)$alkoxy optionally substituted with up to three fluoro;

$R^{12}$ and $R^{13}$ are each independently hydrogen or $(C_1-C_4)$ alkyl.

This invention is also directed to compounds of Formula I, prodrugs thereof and pharmaceutically acceptable salts of said compounds and said prodrugs, wherein:

A is $SO_2$;

$R^1$ and $R^2$ are each independently selected from hydrogen and methyl;

$R^3$ is $Het^1$;

$Het^1$ is indol-2-yl, indol-3-yl, benzofuran-2-yl, benzofuran-3-yl, benzothien-2-yl, benzothien-3-yl, imidazo[1,2a]pyridinyl, pyrrolyl, imidazolyl, indazolyl, tetrahydroquinolyl or tetrahydroindolyl, wherein said $Het^1$ is optionally independently substituted with up to a total of two substituents each independently selected from chloro, methyl, benzyl, methoxy, fluoro, 4-fluorophenyl, isopropyl, phenyl, trifluoromethyl, ethyl and hydroxy.

This invention is also directed to compounds of Formula I, prodrugs thereof and pharmaceutically acceptable salts of said compounds and said prodrugs, wherein:

A is $SO_2$;

$R^1$ and $R^2$ are each independently selected from hydrogen and methyl;

$R^3$ $Het^1$;

$Het^1$ is indol-2-yl or indol-3-yl, said indol-2-yl or indol-3-yl being optionally independently substituted with up to two substituents each independently selected from methyl, methoxy and chloro.

This invention is also directed to compounds of Formula I, prodrugs thereof and pharmaceutically acceptable salts of said compounds and said prodrugs, wherein:

A is $SO_2$;

$R^1$ and $R^2$ are each independently selected from hydrogen and methyl;

$R^3$ is $Het^1$;

$Het^1$ is benzofuran-2-yl, said benzofuran-2-yl being optionally independently substituted with up to two substituents each independently selected from methyl, methoxy, chloro, fluoro, ethyl, 4-fluorophenyl, trifluoromethyl, isopropyl, phenyl and hydroxy.

This invention is also directed to compounds selected from 6-(indole-2-sulfonyl)-2H-pyridazin-3-one; 6-(5-chloro-3-methyl-benzofuran-2-sulfonyl)-2H-pyridazin-3-one; 6-(benzofuran-2-sulfonyl)-2H-pyridazin-3-one; 6-(5- methoxy-benzofuran-2-sulfonyl)-2H-pyridazin-3-one; 6-(3,5-dimethyl-benzofuran-2-sulfonyl)-2H-pyridazin-3-one; 6-(5,7-dichloro-benzofuran-2-sulfonyl)-2H-pyridazin-3-one; 6-(5-chloro-benzofuran-2-sulfonyl)-2H-pyridazin-3-one; 6-(3-methyl-benzofuran-2-sulfonyl)-2H-pyridazin-3-one; 6-(5-trifluoromethyl-3-methyl-benzofuran-2-sulfonyl)-2H-pyridazin-3-one; 6-(5-chloro-3-isopropyl-benzofuran-2-sulfonyl)-2H-pyridazin-3-one; 6-(5-fluoro-3-methyl-benzofuran-2-sulfonyl)-2H-pyridazin-3-one; 6-(6-chloro-3-methyl-benzofuran-2-sulfonyl)-2H-pyridazin-3-one; 6-(3-hydroxy-benzofuran-2-sulfonyl)-2H-pyridazin-3-one; 6-(5-chloro-3-hydroxy-benzofuran-2-sulfonyl)-2H-pyridazin-3-one; 6-(5-chloro-3-methyl-benzothiophene-2-sulfonyl)-2H-pyridazin-3-one; 6-(5-methyl-benzothiophene-2-sulfonyl)-2H-pyridazin-3-one; 6-benzothiophene-2-sulfonyl)-2H-pyridazin-3-one; 6-(3-phenyl-benzofuran-2-sulfonyl)-2H-pyridazin-3-one; 6-(3-[4-fluorophenyl]-benzofuran-2-methylsulfonyl)-2H-pyridazin-3-one; 6-(thieno[2,3b]pyridine-2-sulfonyl)-2H-pyridazin-3-one; 2-(6-oxo-1,6-dihydro-pyridazine-3-sulfonyl)-5H-furo[3.2-c]pyridin-4-one; 6-(5-chloro-3-ethyl-benzofuran-2-sulfonyl)-2H-pyridazin-3-one; 6-(imidazo[1,2a]pyridine-3-sulfonyl)-2H-pyridazin-3-one; 6-(6-chloro-indole-2-sulfonyl)-2H-pyridazin-3-one; 6-(5-methoxy-indole-2-sulfonyl)-2H-pyridazin-3-one; 6-(5-chloro-indole-2-sulfonyl)-2H-pyridazin-3-one; 6-(6-fluoro-indole-2-sulfonyl)-2H-pyridazin-3-one; 6-(5,6-methylenedioxy-indole-2-sulfonyl)-2H-pyridazin-3-one; 6-(7-chloro-indole-2-sulfonyl)-2H-pyridazin-3-one; 6-(5-chloro-3-phenyl-2-sulfonyl)-2H-pyridazin-3-one; 6-(3-chloro-indole-2-sulfonyl)-2H-pyridazin-3-one; 6-(N-benzylindole-5-sulfonyl)-2H-pyridazin-3-one; 6-(5-chloro-3-methyl-benzofuran-2-methylsulfonyl)-2H-pyridazin-3-one; 6-(indole-3-sulfonyl)-2H-pyridazin-3-one; 6-(N-methylindole-2-sulfonyl)-2H-pyridazin-3one; 6-(pyrrole-1-sulfonyl)2H-pyridazin-3-one; 6-(imidazole-1-sulfonyl)2H-pyridazin-3-one; 6-(indole-1-sulfonyl)2H-pyridazin-3-one; 6-(3-chloro-indole-1-sulfonyl)2H-pyridazin-3-one; 6-(3-chloro-indazole-1-sulfonyl)2H -pyridazin-3-one; 6-(3-methyl-indole-1-sulfonyl)-2H-pyridazin-3-one; 6-(tetrahydroquinoline-1sulfonyl)-2H-pyridazin-3-one; 6-(3-[4-fluorophenyl]-benzofuran-2-sulfonyl)-2H-pyridazin-3-one; 6-(imidazo[1,2a]pyridine-4-sulfonyl)-2H-pyridazin-3-one and 6-(2,3-tetrahydro-indole-1-sulfonyl)2H-pyridazin-3-one.

A preferred group of compounds of the preceding paragraph are 6-(indole-2-sulfonyl)-2H-pyridazin-3-one; 6-(benzofuran-2-sulfonyl)-2H-pyridazin-3-one; 6-(5,7-dichloro-benzofuran-2-sulfonyl)-2H-pyridazin-3-one; 6-(5-chloro-benzofuran-2-sulfonyl)-2H-pyridazin-3-one; 6-(3-methyl-benzofuran-2-sulfonyl)-2H-pyridazin-3-one; 6-(5-trifluoromethyl-3-methyl-benzofuran-2-sulfonyl)-2H-pyridazin-3-one; 6-(5-fluoro-3-methyl-benzofuran-2-sulfonyl)-2H-pyridazin-3-one; 6-(3-hydroxy-benzofuran-2-sulfonyl)-2H-pyridazin-3-one; 6-(5-chloro-3-methyl-benzofuran-2-sulfonyl)-2H-pyridazin-3-one; 6-(5-chloro-3-methyl-benzothiophene-2-sulfonyl)-2H-pyridazin-3-one; 6-benzothiophene-2-sulfonyl)-2H-pyridazin-3-one; 6-(3-[4-fluorophenyl]-benzofuran-2-sulfonyl)-2H-pyridazin-3-one; 6-(thieno[2,3b]pyridine-2-sulfonyl)-2H-pyridazin-3-one; 6-(5-chloro-3-ethyl-benzofuran-2-sulfonyl)-2H-pyridazin-3-one; 6-(5-chloro-indole-2-sulfonyl)-2H-pyridazin-3-one; 6-(5-chloro-3-phenyl-2-sulfonyl)-2H-pyridazin-3-one; 6-(5-chloro-3-methyl-benzofuran-2-methylsulfonyl)-2H-pyridazin-3-one; 6-(indole-3-sulfonyl)-2H-pyridazin-3-one; 6-(furano[2,3b]pyridine-2-sulfonyl)-2H-pyridin-3-one; 6-(5methyl-benzofuran2-sulfonyl)-2H-pyridazin-3-one; and 6-(imidazo[1,2a]pyridine-4-sulfonyl)-2H-pyridazin-3-one.

A preferred group of compounds of the preceding paragraph are 6-(benzofuran-2-sulfonyl)-2H-pyridazin-3-one; 6-(5,7-dichloro-benzofuran-2-sulfonyl)-2H-pyridazin-3-one; 6-(5-chloro-benzofuran-2-sulfonyl)-2H-pyridazin-3-one; 6-(3-methyl-benzofuran-2-sulfonyl)-2H-pyridazin-3-one; 6-(5-trifluoromethyl-3-methyl-benzofuran-2-sulfonyl)-2H-pyridazin-3-one; 6-(5-fluoro-3-methyl-benzofuran-2-sulfonyl)-2H-pyridazin-3-one; 6-(5-chloro-3-methyl-benzothiophene-2-sulfonyl)-2H-pyridazin-3-one; 6-(5-chloro-3-methyl-benzofuran-2-sulfonyl)-2H-pyridazin-3-one; 6-benzothiophene-2-sulfonyl)-2H-pyridazin-3-one; 6-(3-[4-fluorophenyl]-benzofuran-2-sulfonyl)-2H-pyridazin-3-one; 6-(5-chloro-3-ethyl-benzofuran-2-sulfonyl)-2H-pyridazin-3-one; 6-(5-chloro-3-phenyl-2-sulfonyl)-2H-pyridazin-3-one; and 6-(5-methyl-benzofuran-2-sulfonyl)-2H-pyridazin-3-one.

A preferred group of compounds of the preceding paragraph are 6-(5-trifluoromethyl-3-methyl-benzofuran-2-sulfonyl)-2H-pyridazin-3-one; 6-(5-chloro-3-methyl-benzofuran-2-sulfonyl)-2H-pyridazin-3-one and 6-(5-fluoro-3-methyl-benzofuran-2-sulfonyl)-2H-pyridazin-3-one.

Another preferred group of compounds of Formula I includes 6-(indole-2-sulfonyl)-2H-pyridazin-3-one, 6-(5-chloro-indole-2-sulfonyl)-2H-pyridazin-3-one, 6-(indole-3-sulfonyl)-2H-pyridazin-3-one, 6-(5-chloro-3-methyl-benzofuran-2-sulfonyl)-2H-pyridazin-3-one, 6-(5-fluoro-3-methyl-benzofuran-2-sulfonyl)-2H-pyridazin-3-one, 6-(5-trifluoromethyl-3-methyl-benzofuran-2-sulfonyl)-2H-pyridazin-3-one, 6-(5-chloro-3-methyl-benzothiophene-2-sulfonyl)-2H-pyridazin-3-one and 6-(benzothiophene-3-sulfonyl)-2H-pyridazin-3-one.

This invention is also directed to pharmaceutical compositions comprising a compound of Formula I, a prodrug thereof or a pharmaceutically acceptable salt of said compound or said prodrug. It is preferred that said pharmaceutical compositions additionally comprise a pharmaceutically acceptable vehicle, carrier or diluent.

This invention is also directed to methods for treating cardiac tissue ischemia in a mammal comprising administering to said mammal an effective amount of a compound of Formula I, a prodrug thereof or a pharmaceutically acceptable salt thereof. This invention is also directed to methods for treating cardiac tissue ischemia in a mammal comprising administering to said mammal a pharmaceutical composition comprising a compound of Formula I and a pharmaceutically acceptable vehicle, carrier or diluent. In these methods, said mammal maybe suffering from cardiac tissue ischemia or may be at risk of suffering from cardiac tissue ischemia. For example, a mammal at risk may be awaiting or undergoing cardiac, cardiovascular or other major surger.

This invention is also directed to methods of inhibiting aldose reductase in a mammal in need of inhibition of aldose reductase comprising administering an aldose reductase inhibiting amount of a compound of Formula I. This invention is also directed to methods of inhibiting aldose reductase in a mammal in need of inhibition of aldose reductase comprising administering a pharmaceutical composition comprising a compound of Formula I and a pharmaceutically acceptable vehicle, carrier or diluent.

This invention is also directed to methods of treating one or more diabetic complications in a mammal suffering from one or more diabetic complications comprising administering to said mammal an effective amount of a compound of Formula I, a prodrug thereof or a pharmaceutically acceptable salt of said compound or said prodrug. Diabetic complications which may be treated by the methods of this invention include, but are not limited to, diabetic neuropathy, diabetic nephropathy, diabetic cardiomyopathy, diabetic retinopathy, cataracts, foot ulcers, diabetic macroangiopathy and diabetic microangiopathy. This invention is also directed to methods of treating one or more diabetic complications in a mammal suffering from one or more diabetic complications comprising administering to said mammal an effective amount of a pharmaceutical composition as set forth herein.

This invention is also directed to pharmaceutical compositions comprising a combination of a first compound and a second compound; wherein said first compound is a compound of Formula I, a prodrug of said first compound or a pharmaceutically acceptable salt of said first compound or of said prodrug of said first compound and said second compound is a NHE-1 inhibitor, an adenosine agonist, a sorbitol dehydrogenase inhibitor (SDI), a glycogen phosphorylase inhibitor (GPI), a selective serotonin reuptake inhibitor (SSRI), a 3-hydroxy-3-methylglutaryl coenzyme A reductase inhibitor (a vastatin), a thiazolidinedione antidiabetic agent (a glitazone), a γ-aminobutyric acid (GABA) agonist, an angiotensin converting enzyme (ACE) inhibitor, angiotensin-II (A-II) receptor antagonist or a phosphodiesterase type 5 (PDE-5) inhibitor, a prodrug of said second compound or a pharmaceutically acceptable salt of said second compound or of said prodrug of said second compound. Particularly preferred second compounds for use in this invention include, but are not limited to, atorvastatin, sildenafil, sertraline, pregabalin, gabapentin, fluoxetine, cerivastatin, pravastatin, mevastatin, lovastatin, simvastatin, pioglitazone, rosiglitazone, benazepril and captopril, and pharmaceutically acceptable salts of said second compounds. This invention is also directed to methods of treating one or more diabetic complications in a mammal comprising administering to a mammal in need of such treatment a pharmaceutical composition as set forth in this paragraph.

This invention is also directed to a method of treating one or more diabetic complications in a mammal comprising administering to a mammal in need of such treatment a combination of a first compound and a second compound; wherein said first compound is a compound of claim 1, a prodrug thereof or a pharmaceutically acceptable salt thereof or of said prodrug, and said second compound is a NHE-1 inhibitor, an adenosine agonist, a sorbitol dehydrogenase inhibitor (SDI), a glycogen phosphorylase inhibitor (GPI), a selective serotonin reuptake inhibitor (SSRI), a 3-hydroxy-3-methylglutaryl coenzyme A reductase inhibitor (a vastatin), a thiazolidinedione antidiabetic agent (a glitazone), a γ-aminobutyric acid (GABA) agonist, an angiotensin converting enzyme (ACE) inhibitor, an angiotensin-II (A-II) receptor antagonist or a phosphodiesterase type 5 (PDE-5) inhibitor, a prodrug of said second compound or a pharmaceutically acceptable salt of said second compound or of said prodrug.

This invention is also directed to kits comprising:
a) a first unit dosage form comprising a compound of Formula I, a prodrug thereof or a pharmaceutically acceptable salt of said compound of Formula I or said prodrug and a pharmaceutically acceptable carrier, vehicle or diluent;
b) a second unit dosage form comprising:
a NHE-1 inhibitor;
an adenosine agonist;
a sorbitol dehydrogenase inhibitor;
a selective serotonin reuptake inhibitor;
a vastatin;
an angiotensin converting enzyme inhibitor;
a thiazolidinedione antidiabetic agent;
a glycogen phosphorylase inhibitor;
an angiotensin II receptor antagonist;
a γ-aminobutyric acid (GABA) agonist; and
a phosphodiesterase type 5 inhibitor;
a prodrug of said sorbitol dehydrogenase inhibitor, selective serotonin reuptake inhibitor, vastatin, angiotensin converting enzyme inhibitor, thiazolidinedione antidiabetic agent, glycogen phosphorylase inhibitor, angiotensin II reuptake inhibitor, γ-aminobutyric acid agonist or phosphodiesterase type 5 inhibitor, or a pharmaceutically acceptable salt thereof or of said prodrug and a pharmaceutically acceptable carrier, vehicle or diluent; and
c) a container.

This invention is also directed to intermediate compounds of Formula II,

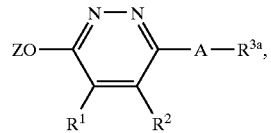

wherein:
A is S, SO or SO$_2$;
Z is (C$_1$–C$_6$)alkyl, phenyl or benzyl, said benzyl or phenyl being optionally substituted with one or two substituents each independently selected from chloro and methyl;
R$^1$ and R$^2$ are each independently hydrogen or methyl;
R$^{3a}$ is Het$^1$, —CHR$^4$Het$^1$;
R$^4$ is hydrogen or (C$_1$–C$_3$)alkyl;
Het$^1$ is pyridyl, pyrimidyl, pyrazinyl, pyridazinyl, quinolyl, isoquinolyl, quinazolyl, quinoxalyl, phthalazinyl, cinnolinyl, naphthyridinyl, pteridinyl, pyrazinopyrazinyl, pyrazinopyridazinyl, pyrimidopyridazinyl, pyrimidopyrimidyl, pyridopyrimidyl, pyridopyrazinyl, pyridopyridazinyl, pyrrolyl, furanyl, thienyl, imidazolyl, oxazolyl, thiazolyl, pyrazolyl, isoxazolyl, isothiazolyl, triazolyl, oxadiazolyl, thiadiazolyl, tetrazolyl, indolyl, benzofuranyl, benzothienyl, benzimidazolyl, benzoxazolyl, benzothiazolyl, indazolyl, benzisoxazolyl, benzisothiazolyl, pyrrolopyridyl, furopyridyl, thienopyridyl, imidazolopyridyl, oxazolopyridyl, thiazolopyridyl, pyrazolopyridyl, isoxazolopyridyl, isothiazolopyridyl, pyrrolopyrimidyl, furopyrimidyl, thienopyrimidyl, imidazolopyrimidyl, oxazolopyrimidyl, thiazolopyrimidyl, pyrazolopyrimidyl, isoxazolopyrimidyl, isothiazolopyrimidyl, pyrrolopyrazinyl, furopyrazinyl, thienopyrazinyl, imidazolopyrazinyl, oxazolopyrazinyl, thiazolopyrazinyl, pyrazolopyrazinyl, isoxazolopyrazinyl, isothiazolopyrazinyl, pyrrolopyridazinyl, furopyridazinyl, thienopyridazinyl, imidazolopyridazinyl, oxazolopyridazinyl, thiazolopyridazinyl, pyrazolopyridazinyl, isoxazolopyridazinyl or isothiazolopyridazinyl; Het$^1$ is independently optionally substituted with up to a total of four substituents each independently selected from halo, formyl, $(C_1-C_6)$alkoxycarbonyl, $(C_1-C_6)$ alkylenyloxycarbonyl, $(C_1-C_4)$alkoxy-$(C_1-C_4)$alkyl, $C(OH)R^{12}R^{13}$, $(C_1-C_4)$alkylcarbonylamido, $(C_3-C_7)$ cycloalkylcarbonylamido, phenylcarbonylamido, phenyl, naphthyl, imidazolyl, pyridyl, triazolyl, benzimidazolyl, oxazolyl, isoxazolyl, thiazolyl, oxadiazolyl, thiadiazolyl, tetrazolyl, thienyl, benzothiazolyl, pyrrolyl, pyrazolyl, quinolyl, isoquinolyl, benzoxazolyl, pyridazinyl, pyridyloxy, pyridylsulfonyl, furanyl, phenoxy, thiophenoxy, $(C_1-C_4)$alkylsulfenyl, $(C_1-C_4)$alkylsulfonyl, $(C_3-C_7)$ cycloalkyl, $(C_1-C_4)$alkyl optionally substituted with up to three fluoro and $(C_1-C_4)$alkoxy optionally substituted with up to five fluoro; said phenyl, naphthyl, imidazolyl, pyridyl, triazolyl, benzimidazolyl, oxazolyl, isoxazolyl, thiazolyl, oxadiazolyl, thiadiazolyl, tetrazolyl, thienyl, benzothiazolyl, pyrrolyl, pyrazolyl, quinolyl, isoquinolyl, benzoxazolyl, pyridazinyl, pyridyloxy, pyridylsulfonyl, furanyl, phenoxy, thiophenoxy, in the definition of the substituents of $Het^1$ are optionally substituted with up to three substituents each independently selected from hydroxy, halo, hydroxy-$(C_1-C_4)$alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to five fluoro; said imidazolyl, oxazolyl, isoxazolyl, thiazolyl and pyrazolyl in the definition of the substituents of $Het^1$ are-optionally substituted with up to two substituents each independently selected from hydroxy, halo, $C_1-C_4$)alkyl, hydroxy-$(C_1-C_4)$ alkyl, $(C_1-C_4)$alkoxy-$(C_1-C_4)$alkyl and $C_1-C_4)$alkylphenyl optionally substituted in the phenyl portion with one Cl, Br, OMe, Me or $SO_2$-phenyl wherein said $SO_2$-phenyl is optionally substituted in the phenyl portion with one Cl, Br, OMe, Me, $(C_1-C_4)$alkyl optionally substituted with up to five fluoro, or $(C_1-C_4)$ alkoxy optionally substituted with up to three fluoro;

$R^{12}$ and $R^{13}$ are each independently hydrogen or $(C_1-C_4)$ alkyl.

A preferred group of compounds of Formula II, designated Group AA, are those compounds and pharmaceutically acceptable salts thereof wherein A is S, $R^1$ and $R^2$ are each H, $R^{3a}$ is $Het^1$ and Z is methyl.

A preferred group of compounds of Group AA, designated Group BB, are those compounds and pharmaceutically acceptable salts thereof wherein $Het^1$ is 5H-furo-[3,2c]pyridin-4-one-2-yl, furano[2,3b]pyridin-2-yl, thieno[2,3b]pyridin-2-yl, indol-2-yl, indol-3-yl, benzofuran-2-yl, benzothien-2-yl, imidazo[1,2a]pyridin-3-yl, pyrrol-1-yl, imidazol-1-yl, indazol-1-yl, tetrahydroquinol-1-yl or tetrahydroindol-1-yl, wherein said $Het^1$ is optionally independently substituted with up to a total of two substituents each independently selected from fluoro, chloro, bromo, $(C_1-C_6)$alkyl, $(C_1-C_6)$alkoxy, trifluoromethyl, hydroxy, benzyl and phenyl; said benzyl and phenyl are each optionally independently substituted with up to three halo, $(C_1-C_6)$ alkyl, $(C_1-C_6)$alkoxy, $(C_1-C_6)$alkylsulfonyl, $(C_1-C_6)$ alkylsulfinyl, $(C_1-C_6)$alkylsulfenyl, trifluoromethyl or hydroxy.

A preferred group of compounds of Group BB, designated Group CC, are those compounds and pharmaceutically acceptable salts thereof wherein $Het^1$ is indol-2-yl, benzofuran-2-yl or benzothien-2-yl, wherein said $Het^1$ is optionally independently substituted with up to a total of two substituents each independently selected from fluoro, chloro, bromo, $(C_1-C_6)$alkyl, $(C_1-C_6)$alkoxy, trifluoromethyl, hydroxy, benzyl and phenyl; said benzyl and phenyl are each optionally independently substituted with up to three halo, $(C_1-C_6)$alkyl, $(C_1-C_6)$alkoxy, $(C_1-C_6)$ alkylsulfonyl, $(C_1-C_6)$alkylsulfinyl, $(C_1-C_6)$alkylsulfenyl, trifluoromethyl or hydroxy.

A preferred compound of Group CC is the compound wherein $Het^1$ is 5-chloro-3-methyl-benzofuran-2-yl and pharmaceutically acceptable salts thereof.

Another preferred group of compounds of Formula II, designated Group DD, are those compounds and pharmaceutically acceptable salts thereof wherein A is $SO_2$, $R^1$ and $R^2$ are each H, $R^{3a}$ is $Het^1$ and Z is methyl.

A preferred group of compounds of Group DD, designated Group EE, are those compounds and pharmaceutically acceptable salts thereof wherein $Het^1$ is 5H-furo-[3,2c]pyridin-4-one-2-yl, furano[2,3b]pyridin-2-yl, thieno[2,3b]pyridin-2-yl, indol-2-yl, indol-3-yl, benzofuran-2-yl, benzothien-2-yl, imidazo[1,2a]pyridin-3-yl, pyrrol-1-yl, imidazol-1-yl, indazol-1-yl, tetrahydroquinol-1-yl or tetrahydroindol-1-yl, wherein said $Het^1$ is optionally independently substituted with up to a total of two substituents each independently selected from fluoro, chloro, bromo, $(C_1-C_6)$alkyl, $(C_1-C_6)$alkoxy, trifluoromethyl, hydroxy, benzyl and phenyl; said benzyl and phenyl are each optionally independently substituted with up to three halo, $(C_1-C_6)$ alkyl, $(C_1-C_6)$alkoxy, $(C_1-C_6)$alkylsulfonyl, $(C_1-C_6)$ alkylsulfinyl, $(C_1-C_6)$alkylsulfenyl, trifluoromethyl or hydroxy.

A preferred group of compounds of Group EE, designated Group FF, are those compounds and pharmaceutically acceptable salts thereof wherein $Het^1$ is indol-2-yl, benzofuran-2-yl or benzothien-2-yl, wherein said $Het^1$ is optionally independently substituted with up to a total of two substituents each independently selected from fluoro, chloro, bromo, $(C_1-C_6)$alkyl, $(C_1-C_6)$alkoxy, trifluoromethyl, hydroxy, benzyl and phenyl; said benzyl and phenyl are each optionally independently substituted with up to three halo, $(C_1-C_6)$alkyl, $(C_1-C_6)$alkoxy, $(C_1-C_6)$ alkylsulfonyl, $(C_1-C_6)$alkylsulfinyl, $(C_1-C_6)$alkylsulfenyl, trifluoromethyl or hydroxy.

A preferred compound of Group FF is the compound wherein $Het^1$ is 5-chloro-3-methyl-benzofuran-2-yl and pharmaceutically acceptable salts thereof.

Another preferred group of compounds of Formula II, designated Group GG, are those compounds and pharmaceutically acceptable salts thereof wherein A is SO, $R^1$ and $R^2$ are each H, $R^{3a}$ is $Het^1$ and Z is methyl.

A preferred group of compounds within Group GG, designated Group HH, are those compounds and pharmaceutically acceptable salts thereof wherein $Het^1$ is 5H-furo-[3,2c]pyridin-4-one-2-yl, furano[2,3b]pyridin-2-yl, thieno[2,3b]pyridin-2-yl, indol-2-yl, indol-3-yl, benzofuran-2-yl, benzothien-2-yl, imidazo[1,2a]pyridin-3-yl, pyrrol-1-yl, imidazol-1-yl, indazol-1-yl, tetrahydroquinol-1-yl or tetrahydroindol-1-yl, wherein said $Het^1$ is optionally independently substituted with up to a total of two substituents each independently selected from fluoro, chloro, bromo, $(C_1-C_6)$alkyl, $(C_1-C_6)$alkoxy, trifluoromethyl, hydroxy, benzyl and phenyl; said benzyl and phenyl are each optionally independently substituted with up to three halo, $(C_1-C_6)$ alkyl, $(C_1-C_6)$alkoxy, $(C_1-C_6)$alkylsulfonyl, $(C_1-C_6)$ alkylsulfinyl, $(C_1-C_6)$alkylsulfenyl, trifluoromethyl or hydroxy.

A preferred group of compounds within Group HH, designated Group II, are those compounds and pharmaceutically acceptable salts thereof wherein $Het^1$ is indol-2-yl, benzofuran-2-yl or benzothien-2-yl, wherein said $Het^1$ is optionally independently substituted with up to a total of two substituents each independently selected from fluoro, chloro, bromo, $(C_1-C_6)$alkyl, $(C_1-C_6)$alkoxy, trifluoromethyl, hydroxy, benzyl and phenyl; said benzyl and phenyl are each optionally independently substituted with up to three halo, $(C_1-C_6)$alkyl, $(C_1-C_6)$alkoxy, $(C_1-C_6)$alkylsulfonyl, $(C_1-C_6)$alkylsulfinyl, $(C_1-C_6)$alkylsulfenyl, trifluoromethyl or hydroxy.

A preferred compound within Group II is the compound wherein $Het^1$ is 5-chloro-3-methyl-benzofuran-2-yl and pharmaceutically acceptable salts thereof.

Another preferred group of compounds of Formula I, designated Group JJ, are those compounds and pharmaceutically acceptable salts thereof wherein A is S or SO; $R^1$ and $R^2$ are each H; and $R^3$ is $Het^1$.

A preferred group of compounds of Group JJ, designated Group KK, are those compounds and pharmaceutically acceptable salts thereof wherein A is S and $Het^1$ is 5H-furo-[3,2c]pyridin-4-one-2-yl, furano[2,3b]pyridin-2-yl, thieno[2,3b]pyridin-2-yl, indol-2-yl, indol-3-yl, benzofuran-2-yl, benzothien-2-yl, imidazo[1,2a]pyridin-3-yl, pyrrol-1-yl, imidazol-1-yl, indazol-1-yl, tetrahydroquinol-1-yl or tetrahydroindol-1-yl, wherein said $Het^1$ is optionally independently substituted with up to a total of two substituents each independently selected from fluoro, chloro, bromo, $(C_1-C_6)$alkyl, $(C_1-C_6)$alkoxy, trifluoromethyl, hydroxy, benzyl or phenyl; said benzyl and phenyl are each optionally independently substitute with up to three halo, $(C_1-C_6)$alkyl, $(C_1-C_6)$alkoxy, $(C_1-C_6)$alkylsulfonyl, $(C_1-C_6)$alkylsulfinyl, $(C_1-C_6)$alkylsulfenyl, trifluoromethyl or hydroxy.

A preferred group of compounds of Group KK, designated Group LL, are those compounds and pharmaceutically acceptable salts thereof wherein $Het^1$ is indol-2-yl, benzofuran-2-yl or benzothien-2-yl, wherein said $Het^1$ is optionally independently substituted with up to a total of two substituents each independently selected from fluoro, chloro, bromo, $(C_1-C_6)$alkyl, $(C_1-C_6)$alkoxy, trifluoromethyl, hydroxy, benzyl and phenyl; said benzyl and phenyl are each optionally independently substituted with up to three halo, $(C_1-C_6)$alkyl, $(C_1-C_6)$alkoxy, $(C_1-C_6)$ alkylsulfonyl, $(C_1-C_6)$alkylsulfinyl, $(C_1-C_6)$alkylsulfenyl, trifluoromethyl or hydroxy.

A preferred compound of Group LL is the compound wherein $Het^1$ is 5-chloro-3-methyl-benzofuran-2-yl and pharmaceutically acceptable salts thereof.

Another group of preferred compounds within Group JJ, designated Group MM, are those compounds and pharmaceutically acceptable salts thereof wherein A is SO and $Het^1$ is 5H-furo-[3,2c]pyridin-4-one-2-yl, furano[2,3b]pyridin-2-yl, thieno[2,3b]pyridin-2-yl, indol-2-yl, indol-3-yl, benzofuran-2-yl, benzothien-2-yl, imidazo[1,2a]pyridin-3-yl, pyrrol-1-yl, imidazol-1-yl, indazol-1-yl, tetrahydroquinol-1-yl or tetrahydroindol-1-yl, wherein said $Het^1$ is optionally independently substituted with up to a total of two substituents each independently selected from fluoro, chloro, bromo, $(C_1-C_6)$alkyl, $(C_1-C_6)$alkoxy, trifluoromethyl, hydroxy, benzyl and phenyl; said benzyl and phenyl are each optionally independently substituted with up to three halo, $(C_1-C_6)$alkyl, $(C_1-C_6)$alkoxy, $(C_1-C_6)$alkylsulfonyl, $(C_1-C_6)$alkylsulfinyl, $(C_1-C_6)$alkylsulfenyl, trifluoromethyl or hydroxy.

A group of preferred compounds within Group MM, designated Group NN, are those compounds and pharmaceutically acceptable salts thereof wherein $Het^1$ is indol-2-yl, benzofuran-2-yl or benzothien-2-yl, wherein said $Het^1$ is optionally independently substituted with up to a total of two substituents each independently selected from fluoro, chloro, bromo, $(C_1-C_6)$alkyl, $(C_1-C_6)$alkoxy, trifluoromethyl, hydroxy, benzyl and phenyl; said benzyl and phenyl are each optionally independently substituted with up to three halo, $(C_1-C_6)$alkyl, $(C_1-C_6)$alkoxy, $(C_1-C_6)$ alkylsulfonyl, $(C_1-C_6)$alkylsulfinyl, $(C_1-C_6)$alkylsulfenyl, trifluoromethyl or hydroxy.

A preferred compound within Group NN is the compound wherein $Het^1$ is 5-chloro-3-methyl-benzofuran-2-yl and pharmaceutically acceptable salts thereof.

Particularly preferred intermediates for use in the synthesis of certain of the compounds of Formula I of this invention include, but are not limited to 6-(5-chloro-3-methyl-benzofuran-2-sulfenyl)-2H-pyridazin-3-one; 3-methoxy-6-(5-chloro-3-methyl-benzofuran-2-sulfonyl)-pyridazine; 3-methoxy-6-(5-chloro-3-methyl-benzofuran-2-sulfenyl)-pyridazine; 3-methoxy-6-(5-chloro-3-methyl-benzofuran-2-sulfinyl)-pyridazine; and 6-(5-chloro-3-methyl-benzofuran-2-sulfinyl)-2H-pyridazin-3-one.

Another preferred intermediate is 5-chloro-2-mercapto-3-methylbenzofuran.

The subject invention also includes isotopically-labeled compounds, which are identical to those recited in Formula I and Formula II, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, sulfur, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. Compounds of Formula I and Formula II of the present invention, prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ or $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. Further, substitution with heavier isotopes such as deuterium, i.e., $^2H$, may afford certain therapeutic advantages resulting from greater metabolic stability, for example increased in vivo half-life or reduced dosage requirements and, hence, may be preferred in some circumstances. Isotopically labeled compounds of Formula I and Formula II of this invention and prodrugs thereof can generally be prepared by carrying out the procedures disclosed in the Schemes and/or in the Examples and Preparations below, by substituting a readily available isotopically labeled reagent for a non-isotopically labeled reagent.

The term "reduction" is intended to include partial prevention or prevention which, although greater than that which would result from taking no compound or from taking a placebo, is less than 100% in addition to substantially total prevention.

The term "treating", "treat" or "treatment" as used herein includes preventative (e.g., prophylactic) and palliative treatment.

By "pharmaceutically acceptable" it is meant the carrier, diluent, excipients, and/or salt must be compatible with the other ingredients of the formulation, and not deleterious to the recipient thereof.

The expression "prodrug" refers to a compound that is a drug precursor which, following administration, releases the drug in vivo via some chemical or, physiological process (e.g., a prodrug on being brought to the physiological pH or through enzyme action is converted to the desired drug form).

By "alkylene" is meant saturated hydrocarbon (straight or branched chain) wherein a hydrogen atom is removed from each of the terminal carbons. Exemplary of such groups (assuming the designated length encompasses the particular example) are methylene, ethylene, propylene, butylene, pentylene, hexylene, heptylene.

By "sulfenyl" is meant S, by "sulfinyl" is meant SO and by "sulfonyl" is meant $SO_2$.

By "halo" is meant chloro, bromo, iodo, or fluoro.

By "alkyl" is meant straight or branched chain saturated hydrocarbon or branched saturated hydrocarbon. Exemplary of such alkyl groups (assuming the designated length encompasses the particular example) are methyl, ethyl, propyl, isopropyl butyl, sec-butyl, tertiary butyl, pentyl, isopentyl, neopentyl, tertiary pentyl, 1-methylbutyl, 2-methylbutyl, 3-methylbutyl, hexyl, isohexyl, heptyl and octyl.

By "alkoxy" is meant straight chain saturated alkyl or branched saturated alkyl bonded through an oxygen. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, neopentoxy, tertiary pentoxy, hexoxy, isohexoxy, heptoxy and octoxy.

By "aryl" is meant a carbon-containing aromatic ring. Examples of such aryl groups include phenyl and naphthyl.

It is to be understood that if a carbocyclic or heterocyclic moiety may be bonded or otherwise attached to a designated substrate through differing ring atoms without denoting a specific point of attachment, then all possible points are intended, whether through a carbon atom or, for example, a trivalent nitrogen atom. For example, the term "pyridyl" means 2-, 3-, or 4-pyridyl, the term "thienyl" means 2-, or 3-thienyl, and so forth.

The expression "pharmaceutically acceptable salts" includes both pharmaceutically acceptable acid addition salts and pharmaceutically acceptable cationic salts, where appropriate. The expression "pharmaceutically-acceptable cationic salts" is intended to include, but is not limited to, such salts as the alkali metal salts, (e.g., sodium and potassium), alkaline earth metal salts (e.g., calcium and magnesium), aluminum salts, ammonium salts, and salts with organic amines such as benzathine (N,N'-dibenzylethylenediamine), choline, diethanolamine, ethylenediamine, meglumine (N-methylglucamine), benethamine (N-benzylphenethylamine), diethylamine, piperazine, tromethamine (2-amino-2-hydroxymethyl-1,3-propanediol) and procaine. The expression "pharmaceutically-acceptable acid addition salts" is intended to include, but is not limited to, such salts as the hydrochloride, hydrobromide, sulfate, hydrogen sulfate, phosphate, hydrogen phosphate, dihydrogenphosphate, acetate, succinate, citrate, methanesulfonate (mesylate) and p-toluenesulfonate (tosylate) salts. A particularly preferred salt is the sodium salt.

Pharmaceutically acceptable cationic salts of the compounds of this invention may be readily prepared by reacting the free acid form of said compounds with an appropriate base, usually one equivalent, in a co-solvent. Typical bases are sodium hydroxide, sodium methoxide, sodium ethoxide, sodium hydride, potassium methoxide, potassium carbonate, sodium carbonate, magnesium hydroxide, calcium hydroxide, benzathine, choline, diethanolamine, piperazine and tromethamine. The salt is isolated by concentration to dryness or by addition of a non-solvent. In many cases, salts are preferably prepared by mixing a solution of the acid with a solution of a different salt of the-cation (sodium or potassium ethylhexanoate, magnesium oleate), and employing a solvent (e.g., ethyl acetate) from which the desired cationic salt precipitates, or can be otherwise isolated by concentration and/or addition of a non-solvent. They can be further purified by crystallization from ($C_1$–$C_6$)alcoholic solvents such as methanol, ethanol or isopropanol or from ketonic solvents such as acetone, methyl ethyl ketone or methyl isobutyl ketone.

The acid addition salts of the compounds of this invention may be readily prepared by reacting the free base form of said compounds with the appropriate acid. When the salt is of a monobasic acid (e.g., the hydrochloride, the hydrobromide, the p-toluenesulfonate, the acetate), the hydrogen form of a dibasic acid (e.g., the hydrogen sulfate, the succinate) or the dihydrogen form of a tribasic acid (e.g., the dihydrogen phosphate, the citrate), at least one molar equivalent and usually a molar excess of the acid is employed. However when such salts as the sulfate, the hemisuccinate, the hydrogen phosphate or the phosphate are desired, the appropriate and exact chemical equivalents of acid will generally be used. The free base and the acid are usually combined in a co-solvent from which the desired salt precipitates, or can be otherwise isolated by concentration and/or addition of a non-solvent. They can be further purified by crystallization from ($C_1$–$C_6$)alcoholic solvents such as methanol, ethanol or isopropanol or from ketonic solvents such as acetone, methyl ethyl ketone or methyl isobutyl ketone.

Prodrugs of this invention may be formed by substituting a compound of Formula I at the 2-nitrogen position of the pyridazin-3-one ring as shown below:

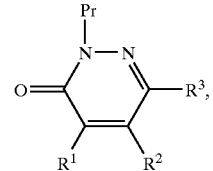

wherein Pr is ($C_1$–$C_6$)alkyl or benzyl. These prodrugs may be prepared by reacting a compound of Formula I with a compound of the formula Pr—X, wherein Pr is as defined above and X is bromo, chloro or iodo in the presence of a base such as, for example, sodium hydride or n-butyl lithium in a reaction inert solvent, such as, for example, dimethylformamide, tetrahydrofuran or ether. The reaction is generally carried out at temperatures ranging from about 0° C. to about room temperature when using sodium hydride as the base. When using n-butyl lithium or a similar base, the reaction is generally carried out at temperatures ranging from about −60° C. to about 0° C. Other processes for preparing such prodrugs will be readily apparent to the skilled person.

As used herein, the expressions "reaction inert solvent" and "inert solvent" refer to a solvent or mixture of solvents which does not interact with starting materials, reagents, intermediates or products in a manner which adversely affects the yield of the desired product.

The chemist of ordinary skill will recognize that certain compounds of Formula I of this invention will contain one or more atoms which may be in a particular stereochemical or geometric configuration, giving rise to stereoisomers and configurational isomers. All such isomers and mixtures thereof are included in this invention. Compounds of Formula I may be chiral. In such cases, the isomer wherein $R^1$ has the R configuration is preferred. Hydrates and solvates of the compounds of Formula I of this invention are also included.

The chemist of ordinary skill in the art will also recognize that certain compounds of Formula I of this invention can exist in tautomeric form, i.e., that an equilibrium exists between two isomers which are in rapid equilibrium with each other. A common example of tautomerism is keto-enol tautomerism, i.e.,

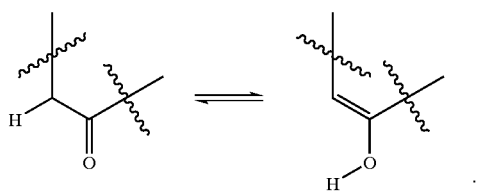

Examples of compounds which can exist as tautomers include hydroxypyridines, hydroxypyrmidines and hydroxyquinolines. In particular, a person skilled in the art will recognize that the pyridazinones of the instant invention can exist as two separate tautomers, e.g.,

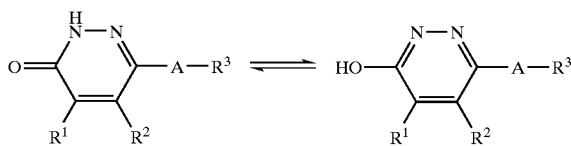

Other examples will be recognized by those skilled in the art. All such tautomers and mixtures thereof are included in this invention.

DMF means N,N-dimethylformamide. DMSO means dimethyl sulfoxide. THF means tetrahydrofuran.

Whenever the structure of a cyclic radical is shown with a bond drawn from outside the ring to inside the ring, it will be understood by those of ordinary skill in the art to mean that the bond may be attached to any atom on the ring with an available site for bonding. If the cyclic radical is a bicyclic or tricyclic radical, then the bond may be attached to any atom on any of the rings with an available site for bonding. For example,

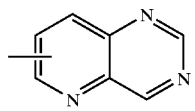

represents any or all of the following radicals:

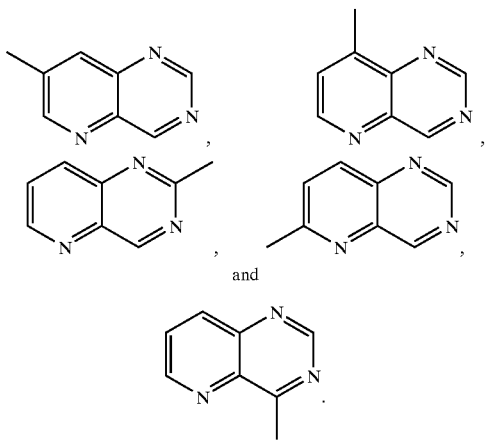

Other features and advantages will be apparent from the specification and claims which describe the invention.

DETAILED DESCRIPTION OF THE INVENTION

In general the compounds of Formula I of this invention can be made by processes which include processes analogous to those known in the chemical arts, particularly in light of the description contained herein. Certain processes for the manufacture of the compounds of Formula I of this invention are provided as further features of the invention and are illustrated by the following reaction schemes. Other processes are described in the experimental section.

Scheme 1

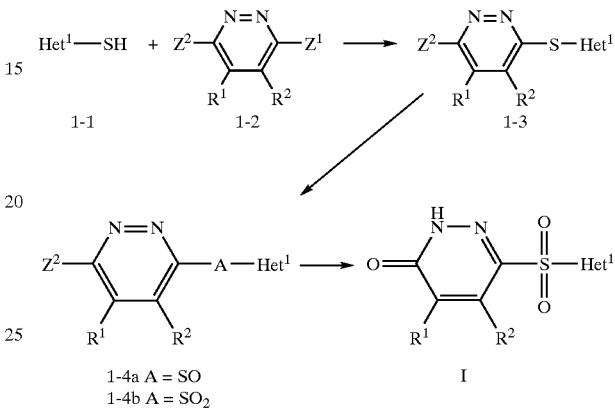

According to Scheme 1, compounds of Formula I, wherein $R^1$ and $R^2$ are as defined above and $R^3$ is $Het^1$, can be prepared from the corresponding pyridazine of formula 1-2 and a heterocyclic thiol of formula 1-1. A thiol 1-1, in which $R^3$ of the compounds of Formula I is $Het^1$, is reacted with a base such as an alkali metal $(C_1-C_6)$alkoxide in a $(C_1-C_6)$alkanol, to obtain the alkali metal salt of said thiol. Preferred alkali metal $(C_1-C_6)$alkoxides include, but are not limited to, sodium methoxide, sodium ethoxide and potassium t-butoxide. After evaporating the excess solvent, the resulting alkali metal salt of said thiol is refluxed with a compound of formula 1-2 wherein $Z^1$ and $Z^2$ are each independently selected from chloro, $(C_1-C_6)$alkoxy, phenyloxy or benzyloxy, said benzyloxy or phenyloxy being optionally substituted with one or two chloro or methyl groups in an aromatic hydrocarbon solvent or solvent system, for example, toluene, benzene or xylene. The reaction is allowed to stir overnight to obtain a compound of formula 1-3. The reaction is usually conducted at ambient pressure and at the refluxing temperature of the solvent used. Compounds of formula 1-3 can also be prepared by reacting compounds 1-2, wherein $R^1$, $R^2$, $Z^1$ and $Z^2$ are as defined above with a compound of formula 1-1 in a reaction inert solvent such as a polar non-aqueous solvent containing an alkali or alkali earth metal hydride or an alkali or alkali earth $(C_1-C_4)$alkoxide. Preferred such solvents include, but are not limited to, acetonitrile and ether solvents such as diglyme, tetrahydrofuran (THF) and dimethylformamide (DMF). Preferred such alkali or alkali earth metal hydrides include, but are not limited to, sodium hydride. Preferred alkali or alkali earth metal $(C_1-C_4)$alkoxides include, but are not limited to, potassium t-butoxide. The preferred metal hydride is sodium hydride. A particularly preferred solvent is DMF. Compounds of formula 1-3 can also be prepared by reacting a compound of formula 1-1 with a compound of formula 1-2, wherein the variables are as defined above, in a reaction inert solvent such as DMF, THF, diglyme or dioxane containing sodium carbonate, potassium carbonate, sodium bicarbonate or potassium bicarbonate. This reaction is usually conducted at ambient pressure and at temperatures between about 60° C. and about 120° C. A compound of formula 1-3 can be oxidized to afford a sulfoxide or a sulfonyl compound of formula 1-4a and/or 1-4b, respectively. A preferred procedure is oxidation of a compound of formula 1-3 with 30% hydrogen peroxide in the presence or absence of an organic acid such as formic acid or acetic acid. Another preferred oxidation procedure involves the use of peracid in the corresponding organic acid as solvent. Yet another preferred procedure is oxidation of a compound of formula 1-3 with a peracid, for example meta-chloroperbenzoic acid (MCPBA), in a halocarbon solvent, for example, methylene chloride, chloroform or ethylene chloride. In any case, the reaction is conducted at ambient pressure and at temperatures between about 20° C. and about −40° C. with careful reaction monitoring to avoid formation of N-oxides by over-oxidation at the nitrogen atom. The oxidation reaction is usually complete within three to six hours and proceeds through sulfoxide 1-4a, but occasionally may be complete prior to the passage of three hours, as determined by a person skilled in the art. If the reaction is conducted at between about 20° C. and about 30° C., and is stopped at between one to three hours, sulfoxide 1-4a can be isolated using separation procedures well known to a person skilled in the art. The resulting sulfone of formula 1-4b can then be hydrolyzed with a mineral acid such as, but not limited to, concentrated hydrochloric acid with no solvent or in a reaction inert solvent such as an ether solvent, for example, dioxane, tetrahydrofuran or diethyl ether, to obtain a compound of Formula I. The hydrolysis reaction is generally conducted at ambient pressure and at the refluxing temperature of the solvent used.

Scheme 1A

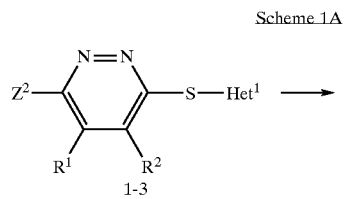

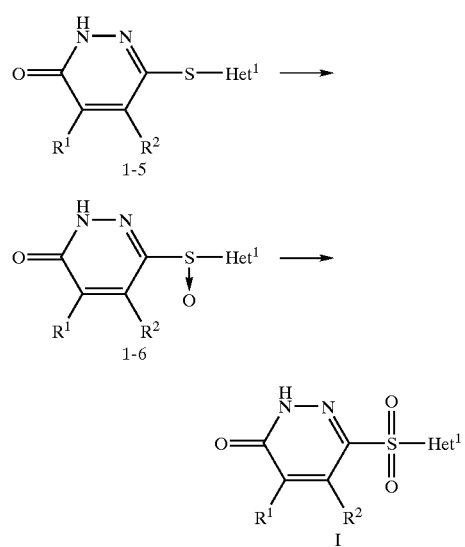

According to Scheme 1A, compounds of Formula I can also be prepared by reversing the order of the last two steps of Scheme I, i.e., by formation of the oxo compound of Formula I prior to oxidation of the sulfide of formula 1-5 to the sulfone of Formula I via the sulfoxide of Formula 1-6. Thus, a compound of formula 1-3 is hydrolyzed in the manner described above to afford a pyridazinone compound of formula 1-5, which is then oxidized in the manner described above to afford a compound of Formula I. Compounds of formula 1-6 can also be prepared by hydrolyzing compounds of formula 1-4a as described for Scheme 1.

Scheme 2

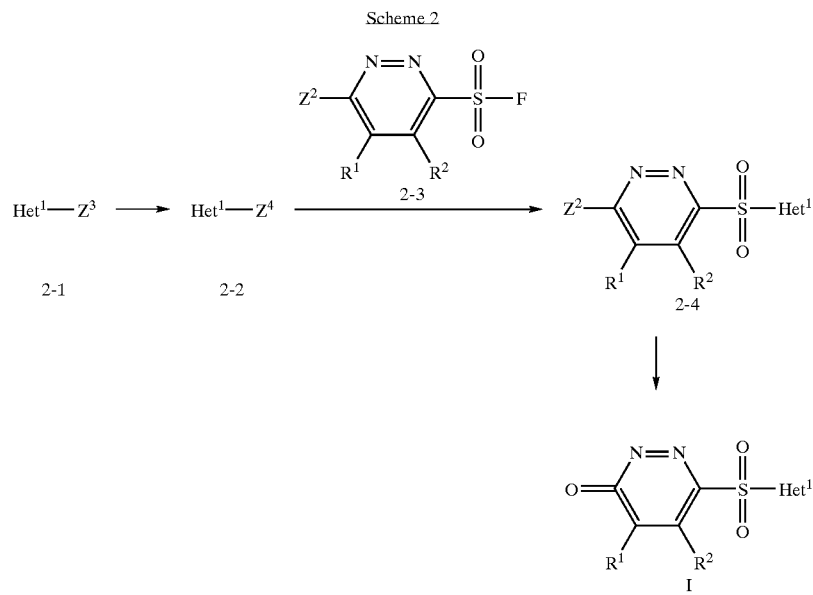

According to Scheme 2, compounds of Formula I can be prepared by reacting compounds of the formula $Het^1$-$Z^3$ where $Z^3$ is bromide, iodide or an acidic hydrogen with a suitable organometallic base to form compounds of the formula $Het^1$-$Z^4$ wherein $Z^4$ is the cation corresponding to the organometallic base. $Het^1$-$Z^4$ may in turn may be reacted with a fluorosulfonyl pyridazine compound of the formula 2-3 to form a sulfonyl pyridazine of the formula 2-4 which may be hydrolyzed to form a compound of Formula I. In the case where $Z^3$ is an acidic hydrogen, the hydrogen will be acidic enough such that said, hydrogen is removable by reaction with a base such as, but not limited to, $(C_1-C_6)$ alkyllithium, lithium diisopropylamide (LDA) or phenyl lithium. Thus, a compound of formula 2-1 in which $Z^3$ is bromide, iodide or a hydrogen of sufficient acidity, is reacted with a base such as, but not limited to, $(C_1-C_6)$alkyllithium, lithium diisopropylamide (LDA) or phenyl lithium to prepare a compound of formula 2-2, wherein $Z^4$ is lithium. A hydrogen of sufficient acidity is a hydrogen that can be removed from $Het^1$-$Z^3$ by the bases mentioned in the preceding sentence. The reaction is conducted in a reaction inert solvent such as an ether or a hydrocarbon solvent or a mixture of such solvents. Preferred solvents include, but are not limited to, diethyl ether, tetrahydrofuran, diglyme, benzene and toluene or mixtures thereof. The reaction is conducted at temperatures from about −78° C. to about 0° C. and at ambient pressure. A compound of formula 2-2 is reacted with a compound of formula 2-3 wherein $Z^2$ is chloro, $(C_1-C_6)$alkoxy, phenyloxy or benzyloxy, said phenyloxy or benzyloxy being optionally substituted with one or two chloro or methyl groups to form compounds of formula 2-4 wherein $Z^2$ is as defined above. The reaction is conducted in a reaction inert solvent such as an ether or a hydrocarbon solvent or a mixture of such solvents. Preferred solvents include, but are not limited to, diethyl ether, tetrahydrofuran, diglyme, benzene and toluene or mixtures thereof. The reaction is conducted at temperatures ranging, from about −78° C. to about 0° C. and at ambient pressure. Compounds 2-4 are hydrolyzed to form compounds of Formula I as described above.

Also according to Scheme 2, compounds of formula 2-4 may be prepared by reacting a compound of formula 2-2 wherein $Z^4$ is MgBr or MgI using standard Grignard reaction conditions, e.g., by reacting a compound of formula 2-1 wherein $Z^3$ is bromide or iodide with magnesium to form the compound of formula 2-2 which is reacted, preferably in situ, with a compound of formula 2-3 wherein $Z^2$ is as defined above. The reaction is generally conducted in a reaction inert solvent such as an ether or a hydrocarbon solvent or a mixture of such solvents. Preferred solvents include, but are not limited to, diethyl ether, tetrahydrofuran, diglyme, benzene and toluene or mixtures thereof. The reaction temperature ranges from about −10° C. to about 40° C. Formation of the Grignard reagent of formula 2-2 may be readily accomplished according to methods well known to those skilled in the art.

Scheme 3

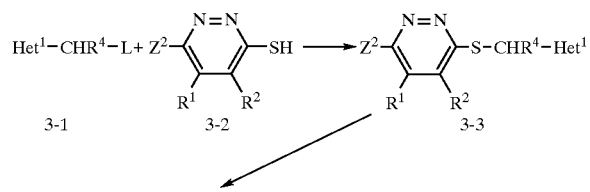

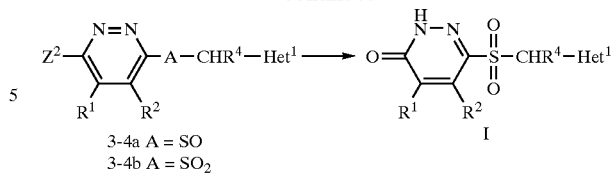

3-4a A = SO
3-4b A = $SO_2$

According to Scheme 3, compounds of Formula I wherein $R^1$, $R^2$, $Z^2$ and $Het^1$ are defined as described above and $R^3$ is $CHR^4$-$Het^1$ may be prepared by reacting a compound of the formula 3-1 with a compound of the formula 3-2 followed by further modification. Thus, a compound of the formula 3-1 wherein L is a leaving group such as chloro, bromo, iodo, methanesulfonyloxy, phenylsulfonyloxy wherein said phenyl of said phenylsulfonyloxy may be optionally substituted by one nitro, chloro, bromo or methyl is reacted with a compound of the formula 3-2, wherein $Z^2$ is as described above, to form a compound of the formula 3-3. The reaction is conducted in a reaction inert solvent such as methylene chloride, chloroform, diethyl ether, tetrahydrofuran, dioxane, acetonitrile or dimethylformamide at a temperature ranging from about room temperature to about 90° C. The reaction is conducted at ambient pressure. A compound of the formula 3-3 is then oxidized to form a sulfoxide or sulfonyl compound of the formula 3-4a and/or 3-4b, respectively, by reacting said compound of formula 3-3 with an oxidizing agent such as metachloroperbenzoic acid (MCPBA) in a reaction inert solvent or hydrogen peroxide in acetic acid. The sulfoxide of formula 3-4a may be isolated by halting the oxidation reaction as described in Scheme 1 above. When MCPBA is used, preferred reaction inert solvents include such solvents as methylene chloride and chloroform. The reaction is ordinarily performed at room temperature. When hydrogen peroxide is used as the oxidizing agent, the reaction is carried out as described above. Compounds of formula 3-4b thus prepared may be hydrolyzed to form compounds of Formula I according to conditions described in Scheme 1 above.

Scheme 4

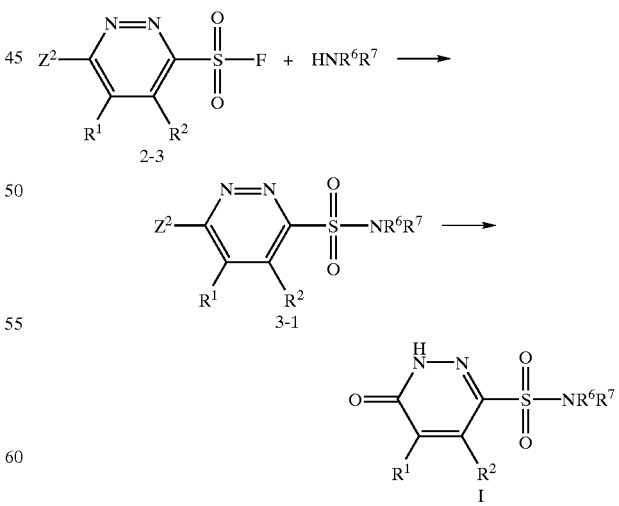

According to Scheme 4, compounds of Formula I wherein $R^1$, $R^2$ and Z are defined as set forth above and $R^3$ is —$NR^6R^7$ may be prepared from compounds of formula 2-3. Thus, a compound of formula 2-3 is reacted with an amine of the formula $HNR^6R^7$, wherein $R^6$ and $R^7$ are defined as set forth above, in the presence of excess $HNR^6R^7$ or a tertiary amine such as, but not limited to, triethyl amine or diisopropyl ethyl amine in a reaction inert solvent to form a compound of the formula 3-1. Preferred reaction inert solvents for this reaction include, but are not limited to, methylene chloride, chloroform, diethyl ether, tetrahydrofuran and dioxane. The reaction is preferably conducted at a temperature ranging from about 0° C. to about 100° C. Compounds of formula 3-1 thus prepared may be hydrolyzed to form compounds of Formula I as described above.

The starting materials and reagents for the above described compounds are also readily available or can be easily synthesized by those skilled in the art using conventional methods of organic synthesis. For example, many of the compounds used herein are related to, or are derived from, compounds found in nature, in which there is a large scientific interest and commercial need, and accordingly many such compounds are commercially available or are reported in the literature or are easily prepared from other commonly available substances by methods which are reported in the literature.

The compounds of Formula I of the present invention inhibit the bioconversion of glucose to sorbitol catalyzed by the enzyme aldose reductase and as such have utility in the treatment of diabetic complications including but not limited to such complications as diabetic neuropathy, diabetic retinopathy, diabetic nephropathy, diabetic cardiomyopathy, diabetic cataracts, tissue ischemia, diabetic microangiopathy and diabetic macroangiopathy. Such aldose reductase inhibition is readily determined by those skilled in the art according to standard assays known to those skilled in the art (e.g., B. L. Mylari at al., J. Med. Chem., 1991, 34, 108–122) and according to the protocol described in Example 51.

Cardioprotection, as indicated by a reduction in infarcted myocardium, can be induced pharmacologically using adenosine receptor agonists in isolated, retrogradely perfused rabbit hearts, as an in vitro model of myocardial ischemic preconditioning (Liu et al., Cardiovasc. Res., 28:1057–1061, 1994). The in vitro test described following demonstrates that a test compound (i.e., a compound as claimed herein) can also pharmacologically induce cardioprotection, i.e., reduced myocardial infarct size, when administered to a rabbit isolated heart. The effects of the test compound are compared to ischemic preconditioning and the A1/A3 adenosine agonist, APNEA 2-(4-aminophenyl) ethyl adenosine), that has been shown to pharmacologically induce cardioprotection in the rabbit isolated heart (Liu et al., Cardiovasc. Res., 28:1057–1061, 1994). The exact methodology is described below.

The protocol used for these experiments closely follows that described by Liu et al., Cardiovasc. Res., 28:1057–1061, 1994. Male New Zealand White rabbits (3–4 kg) are anesthetized with sodium pentobarbital (30 mg/kg, i.v.). After deep anesthesia is achieved (determined by the absence of an ocular blink reflex) the animal is intubated and ventilated with 100% $O_2$ using a positive pressure ventilator. A left thoracotomy is performed, the heart exposed, and a snare (2-0 silk) is placed loosely around a branch of the left anterior descending coronary artery, approximately ⅔ of the distance towards the apex of the heart. The heart is removed from the chest and rapidly (<30 cc) mounted on a Langendorff apparatus. The heart is retrogradely used via the aorta in a non-recirculating manner with a modified Krebs solution (NaCl 118.5 mM, KCl 4.7 mM, $MgSO_4$ 1.2 mM, $KH_2PO.sub.4$ 1.2 mM, $NaHCO_3$ 24.8 mM, $CaCl_2$ 2.5 mM, and glucose 10 mM), at a constant pressure of 80 mmHg and a temperature of 37° C. Perfusate pH is maintained at 7.4–7.5 by bubbling with 95% $O_2$/5% $CO_2$. Heart temperature is tightly controlled by using heated reservoirs for the physiological solution and water jacketing around both the perfusion tubing and the isolated heart. Heart rate and left ventricular pressures are determined via a latex balloon which is inserted in the let ventricle and connected by stainless steel tubing to a pressure transducer. The intraventricular balloon is inflated to provide a systolic pressure of 80–100 mmHg, and a diastolic pressure $\leq$10 mmHg. Total coronary flow is also continuously monitored using an in-line flow probe and normalized for heart weight.

The heart is allowed to equilibrate for 30 min, over which time the heart must show stable left ventricular pressures within the parameters outlined above. If the heart rate falls below 180 bpm at any time prior to the 30 min period of regional ischemia, the heart is paced at about 200 bpm for the remainder of the experiment. Ischemic preconditioning is induced by total cessation of cardiac perfusion (global ischemia) for 5 min, followed by reperfusion for 10 min. The global ischemia/reperfusion is repeated one additional time, followed by a 30 min regional ischemia. The regional ischemia is provided by tightening the snare around the coronary artery branch. Following the 30 min regional ischemia, the snare is released and the heart reperfused for an additional 120 min.

Pharmacological cardioprotection is induced by infusing the test compound at predetermined concentrations, starting 30 min prior to the 30 min regional ischemia, and continuing until the end of the 120 min reperfusion period. Hearts, which receive test compounds, do not undergo the two periods of ischemic preconditioning. The reference compound, APNEA (500 nM) is perfused through hearts (which do not receive the test compound) for a 5 min period which ends 10 min before the 30 min regional ischemia.

At the end of the 120 min reperfusion period, the coronary artery snare is tightened, and a 0.5% suspension of fluorescent zinc cadmium sulfate particles (1–10 $\mu$M) is perfused through the heart; this stains all of the myocardium, except that area at risk for infarct development (area-at-risk). The heart is removed from the Langendorff apparatus, blotted dry, weighed, wrapped in aluminum foil and stored overnight at −20° C. The next day, the heart is sliced into 2 mm transverse sections from the apex to just above the coronary artery snare. The slices are stained with 1% triphenyl tetrazolium chloride (TTC) in phosphate-buffered saline for 20 min at 37° C. Since TTC reacts with living tissue (containing NAD-dependent dehydrogenases), this stain differentiates between living (red stained) tissue, and dead tissue (unstained infarcted tissue). The infarcted area (no stain) and the area-at-risk (no fluorescent particles) are calculated for each slice of left ventricle using a precalibrated image analyzer. To normalize the ischemic injury for difference in the area-at-risk between hearts, the data is expressed as the ratio of infarct area vs. area-at-risk (%IA/AAR).

The activity and thus utility of the compounds of the present invention as medical agents in providing protection from ischemic damage to tissue in a mammal can be further demonstrated by the activity of the compounds in the in vitro assay described herein below. The assay also provides a means whereby the activities of the compounds of this invention can be compared with the activities of other known compounds. The results of these comparisons are useful for determining dosage levels in mammals, including humans, for inducing protection from ischemia.

The activity of an aldose reductase inhibitor in a tissue can be determined by testing the amount of aldose reductase inhibitor that is required to inhibit tissue sorbitol or lower tissue fructose (by inhibiting its production from sorbitol consequent to blocking aldose reductase). While not wishing to be bound by any particular theory or mechanism, it is believed that an aldose reductase inhibitor, by inhibiting aldose reductase, prevents or reduces ischemic damage as described hereinafter in the following paragraph and scheme.

When the supply of oxygenated blood to a tissue is interrupted or slowed down (ischemia) the cells in the oxygen-deficient tissue derive their energy (ATP) from glucose via glycolysis (which does not require the presence of oxygen). Glycolysis also requires a supply of $NAD^+$ and in an ischemic tissue the length of time glycolysis can be maintained becomes sensitive to the supply of $NAD^+$. Thus, it follows that sparing $NAD^+$. use by ARIs will enhance or prolong the ability of ischemic tissue to carry out glycolysis, i.e., to produce energy in the absence of oxygen and in turn enhance and prolong the survival of the cells in the tissue. Since, inhibition of AR will retard depletion of the tissue's $NAD^+$, an aldose reductase inhibitor is an effective anti-ischemic agent.

This invention also relates to therapeutic methods of treating or preventing diabetic complications in which a compound of Formula I of this invention is administered as part of an appropriate dosage regimen designed to obtain the benefits of the therapy. The appropriate dosage regimen, the amount of each dose administered and the intervals between doses of the compound will depend upon the compound of Formula I of this invention being used, the type of pharmaceutical formulation being used, the characteristics of the subject being treated and the severity of the conditions. Generally, in carrying out the methods of this invention, an effective dosage for the compounds of Formula I of this invention is in the range of about 0.01 mg/kg/day to about 500 mg/kg/day in single or divided doses. A preferred dosage range for the compounds of Formula I of this invention is about 0.1 mg/kg/day to about 100 mg/kg/day in single or divided doses. However, some variation in dosage will necessarily occur depending on the condition of the subject being treated. The individual responsible for dosing will, in any event, determine the appropriate dose for the individual subject.

The standard assays used to determine aldose reductase inhibiting activity, as referenced above, may be used to determine dosage levels in humans and other mammals of the compounds of Formula I of this invention. Such assays provide a means to compare the activities of the compounds of Formula I of this invention and other known compounds that are aldose reductase inhibitors. The results of these comparisons are useful for determining such dosage levels.

The term "Second Agents" hereinafter refers collectively to pharmaceutical compounds or agents that are NHE-1 inhibitors, adenosine agonists, sorbitol dehydrogenase inhibitors, selective serotonin reuptake inhibitors, 3-hydroxy-3-methylglutaryl coenzyme A reductase inhibitors, angiotensin converting enzyme inhibitors, thiazolidinedione antidiabetic agents, glycogen phosphorylase inhibitors, angiotensin II receptor antagonists, γ-aminobutyric acid agonist, phosphodiesterase type 5 inhibitors, prodrugs of said compounds or agents, and pharmaceutically acceptable salts of such compounds, agents and prodrugs. Use of the term in singular form, as in "a Second Agent" hereinafter refers to a pharmaceutical agent selected from said Second Agents. A Second Agent may be a pharmaceutical agent that shares more than one of the foregoing characteristics.

An additional aspect of this invention relates to pharmaceutical compositions comprising a compound of Formula I of this invention, and a Second Agent. Such compositions are hereinafter referred to collectively as the "combination compositions".

This invention also relates to therapeutic methods for treating or preventing diabetic complications in a mammal wherein a compound of Formula I of this invention and a Second Agent are administered together as part of the same pharmaceutical composition or separately. Such methods are hereinafter referred to collectively as the "combination therapies" of this invention. Combination therapies include therapeutic methods wherein a compound of Formula I of this invention and a Second Agent are administered together as part of the same pharmaceutical composition and to methods wherein these two agents are administered separately, either simultaneously or sequentially in any order.

This invention further provides pharmaceutical kits comprising a compound of Formula I of this invention and a Second Agent. Such kits may hereinafter be referred to as the "kits" of this invention.

Any selective serotonin reuptake inhibitor (SSRI) may be used as the Second Agent in the combination compositions, combination therapies and kits of this invention. The term selective serotonin reuptake inhibitor refers to an agent which inhibits the reuptake of serotonin by afferent neurons. Such inhibition is readily determined by those skilled in the art according to standard assays such as those disclosed in U.S. Pat. No. 4,536,518 and other U.S. patents recited in the next paragraph.

Preferred SSRIs which may be used in accordance with this invention include femoxetine, which may be prepared as described in U.S. Pat. No. 3,912,743; fluoxetine, which may be prepared as described in U.S. Pat. No. 4,314,081; fluvoxamine, which may be prepared as described in U.S. Pat. No. 4,085,225; indalpine, which may be prepared as described in U.S. Pat. No. 4,064,255; indeloxazine, which may be prepared as described in U.S. Pat. No. 4,109,088; milnacipran, which may be prepared as described in U.S. Pat. No. 4,478,836; paroxetine, which may be prepared as described in U.S. Pat. No. 3,912,743 or U.S. Pat. No. 4,007,196; sertraline, which may be prepared as described in U.S. Pat. No. 4,536,518; sibutramine, which may be prepared as described in U.S. Pat. No. 4,929,629; and zimeldine, which may be prepared as described in U.S. Pat. No. 3,928,369. Fluoxetine is also known as Prozac®. Sertraline hydrochloride, also known as Zoloft®, may be prepared as set forth in U.S. Pat. No. 4,536,518. Sibutramine is also known as Meridia®.

SSRIs are preferably administered in amounts ranging from about 0.01 mg/kg/day to about 500 mg/kg/day in single or divided doses, preferably about 10 mg to about 300 mg per day for an average subject, depending upon the SSRI and the route of administration. However, some variation in dosage will necessarily occur depending on the condition of the subject being treated. The individual responsible for dosing will, in any event, determine the appropriate dose for the individual subject.

Any 3-hydroxy-3-methylglutaryl coenzyme A (HMG-CoA) reductase inhibitor (vastatin) may be used as the Second Agent in the combination compositions, combination therapies and kits of this invention. The term 3-hydroxy-3-methylglutaryl coenzyme A (HMG-CoA) reductase inhibitor refers to a pharmaceutical agent which inhibits the enzyme 3-hydroxy-3-methylglutaryl-coenzyme A (HMG-CoA) reductase. This enzyme is involved in the conversion of HMG-CoA to mevalonate, which is one of the steps in cholesterol biosynthesis. Such inhibition is readily determined according to standard assays well known to those skilled in the art.

Preferred vastatins which may be used in accordance with this invention include atorvastatin, disclosed in U.S. Pat. No. 4,681,893, atorvastatin calcium, disclosed in U.S. Pat. No. 5,273,995, cerivastatin, disclosed in U.S. Pat. No. 5,502,199, dalvastatin, disclosed in European Patent Application Publication No. 738,510 A2, fluindostatin, disclosed in European Patent Application Publication No. 363,934 A1, fluvastatin, disclosed in U.S. Pat. No. 4,739,073, lovastatin, disclosed in U.S. Pat. No. 4,231,938, mevastatin, disclosed in U.S. Pat. No. 3,983,140, pravastatin, disclosed in U.S. Pat. No. 4,346,227, simvastatin, disclosed in U.S. Pat. No. 4,444,784 and velostatin, disclosed in U.S. Pat. No. 4,448,784 and U.S. Pat. No. 4,450,171. Especially preferred 3-hydroxy-3-methylglutaryl coenzyme A reductase inhibitors include atorvastatin, atorvastatin calcium, also known as Liptor®, lovastatin, also known as Mevacor®, pravastatin, also known as Pravachol®, and simvastatin, also known as Zocor®.

Vastatins are preferably administered in amounts ranging from about 0.1 mg/kg to about 1000 mg/kg/day in single or divided doses, preferably about 1 mg/kg/day to about 200 mg/kg/day for an average subject, depending upon the vastatin and the route of administration. However, some variation in dosage will necessarily occur depending on the condition of the subject being treated. The individual responsible for dosing will, in any event, determine the appropriate dose for the individual subject.

Any thiazolidinedione antidiabetic agent may be used in the combination compositions, combination therapies and kits of this invention. The term thiazolidinedione antidiabetic agent refers to a pharmaceutical agent that increases insulin sensitivity in tissues important for insulin action such as adipose tissue, skeletal muscle, and liver.

The following patents exemplify thiazolidinedione antidiabetic agents which can be used in the combination compositions, methods and kits of this invention: U.S. Pat. Nos. 4,340,605; 4,342,771; 4,367,234; 4,617,312; 4,687,777 and 4,703,052. Preferred thiazolidinedione antidiabetic agents include darglitazone, ciglitazone, pioglitazone, also known as Actos®, and rosiglitazone, also known as Avandia®.

Thiazolidinedione antidiabetic agents are preferably administered in amounts ranging from about 0.1 mg/day to about 100 mg/day in single or divided doses, preferably about 0.1 mg/day to about 50 mg/day for an average subject, depending upon the thiazolidinedione antidiabetic agent and the route of administration. However, some variation in dosage will necessarily occur depending on the condition of the subject being treated. The individual responsible for dosing will, in any event, determine the appropriate dose for the individual subject.

Any angiotensin converting enzyme (ACE) inhibitor may be used as the Second Agent in the combination compositions, combination therapies and kits of this invention. The term angiotensin converting enzyme inhibitor refers to a pharmaceutical agent which inhibits angiotensin converting enzyme activity. ACE is involved in the conversion of angiotensin I to the vasoconstrictor, angiotensin II. The activity of ACE inhibitors may readily be determined by methods known to those skilled in the art, including any of the standard assays described in the patents listed below.

Preferred ACE inhibitors include: alacepril, disclosed in U.S. Pat. No. 4,248,883; benazepril, disclosed in U.S. Pat. No. 4,410,520; captopril, disclosed in U.S. Pat. Nos. 4,046,889 and 4,105,776; ceronapril, disclosed in U.S. Pat. No. 4,452,790; delapril, disclosed in U.S. Pat. No. 4,385,051; enalapril, disclosed in U.S. Pat. No. 4,374,829; fosinopril, disclosed in U.S. Pat. No. 4,337,201; imadapril, disclosed in U.S. Pat. No. 4,508,727; lisinopril, disclosed in U.S. Pat. No. 4,555,502; moexipril, disclosed in U.S. Pat. No. 4,344,949; moveltopril, disclosed in Belgian Patent No. 893,553; perindopril, disclosed in U.S. Pat. No. 4,508,729; quinapril, disclosed in U.S. Pat. No. 4,344,949; ramipril, disclosed in U.S. Pat. No. 4,587,258; spirapril, disclosed in U.S. Pat. No. 4,470,972; temocapril, disclosed in U.S. Pat. No. 4,699,905; and trandolapril, disclosed in U.S. Pat. No. 4,933,361.

ACE inhibitors are preferably administered in amounts ranging from about 0.01 mg/kg/day to about 500 mg/kg/day in single or divided doses, preferably about 10 mg to about 300 mg per day for an average subject, depending upon the ACE inhibitor and the route of administration. However, some variation in dosage will necessarily occur depending on the condition of the subject being treated. The individual responsible for dosing will, in any event, determine the appropriate dose for the individual subject.

Any angiotensin-II receptor (A-II) antagonist may be used as the Second Agent in the combination compositions, combination therapies and kits of this invention. The term angiotensin-II receptor antagonist refers to a pharmaceutical agent that blocks the vasoconstrictor effects of angiotensin II by blocking the binding of angiotensin II to the $AT_1$ receptor found in many tissues, (e.g., vascular smooth muscle, adrenal gland). The activity of an A-II antagonist may readily be determined by methods known to those skilled in the art, including any of the standard assays described in the patents listed below.

Preferred A-II antagonists include: candesartan, which may be prepared as disclosed in U.S. Pat. No. 5,196,444; eprosartan, which may be prepared as disclosed in U.S. Pat. No. 5,185,351; irbesartan, which may be prepared as disclosed in U.S. Pat. No. 5,270,317; losartan, which may be prepared as disclosed in U.S. Pat. No. 5,138,069; and valsartan, which may be prepared as disclosed in U.S. Pat. No. 5,399,578. More preferred angiotensin-II receptor antagonists are losartan, irbesartan and valsartan.

A-II antagonists are preferably administered in amounts ranging from about 0.01 mg/kg/day to about 500 mg/kg/day in single or divided doses, preferably about 10 mg to about 300 mg per day for an average subject, depending upon the A-II antagonist and the route of administration. However, some variation in dosage will necessarily occur depending on the condition of the subject being treated. The individual responsible for dosing will, in any event, determine the appropriate dose for the individual subject.

Any γ-aminobutyric acid (GABA) agonist may be used as the Second Agent in the combination compositions, combination therapies and kits of this invention. The term γ-aminobutyric acid agonist refers to a pharmaceutical agent that binds to GABA receptors in the mammalian central nervous system. GABA is the major inhibitory neurotransmitter in the mammalian central nervous system. The activity of a GABA agonist may readily be determined by methods known to those skilled in the art, including the procedures disclosed in Janssens de Verebeke, P. et al., Biochem. Pharmacol., 31, 2257–2261 (1982), Loscher, W., Biochem. Pharmacol., 31, 837–842, (1982) and/or Phillips, N. et al., Biochem. Pharmacol., 31, 2257–2261.

Preferred GABA agonists include: muscimol, which may be prepared as disclosed in U.S. Pat. No. 3,242,190; progabide, which may be prepared as disclosed in U.S. Pat. No. 4,094,992; riluzole, which may be prepared as disclosed in U.S. Pat. No. 4,370,338; baclofen, which may be prepared as disclosed in U.S. Pat. No. 3,471,548; gabapentin (Neurontin®), which may be prepared as disclosed in U.S. Pat. No. 4,024,175; vigabatrin, which may be prepared as disclosed in U.S. Pat. No. 3,960,927; valproic acid, which may be prepared as disclosed in Carraz et al., Therapie, 1965, 20, 419; tiagabine (Gabitril®), which may be prepared as disclosed in U.S. Pat. No. 5,010,090; lamotrigine (Lamictal®), which may be prepared as disclosed in U.S. Pat. No. 4,602,017; pregabalin, which may be prepared as disclosed in U.S. Pat. No. 6,028,214; phenytoin (Dilantin®), which may be prepared as disclosed in U.S. Pat. No. 2,409,754; carbamazepine (Tegretol®), which may be prepared as disclosed in U.S. Pat. No. 2,948,718; and topiramate (Topamax®) which may be prepared as disclosed in U.S. Pat. No. 4,513,006; and analogs, derivatives, prodrugs and pharmaceutically acceptable salts of those GABA agonists.

In general, in accordance with this invention, the GABA agonist used in the combinations, pharmaceutical compositions, methods and kits of this invention will be administered in a dosage of about 4 mg/kg body weight of the subject to be treated per day to about 60 mg/kg body weight of the subject to be treated per day, in single or divided doses. However, some variation in dosage will necessarily occur depending upon the condition of the subject being treated. The person responsible for administration will, in any event, determine the appropriate dose for the individual subject. In particular, when used as the GABA agonist in this invention, pregabalin will be dosed at about 300 mg to about 1200 mg per day; gabapentin will be dosed at about 600 mg to about 3600 mg per day.

Any glycogen phosphorylase inhibitor (GPI) may be used as the Second Agent in the combination compositions, combination therapies and kits of this invention. The term glycogen phosphorylase inhibitor refers to any substance or agent or any combination of substances and/or agents which reduces, retards, or eliminates the enzymatic action of glycogen phosphorylase. Such actions are readily determined by those skilled in the art according to standard assays as described in U.S. Pat. No. 5,988,463.

U.S. Pat. No. 5,988,463, PCT application publication WO 96/39384 and PCT application publication WO96/39385 exemplify GPIs which can be used in the combination compositions, methods and kits of this invention, and refer to methods of preparing those GPIs.

GPIs are preferably administered in amounts ranging from about 0.005 mg/kg/day to about 50 mg/kg/day in single or divided doses, preferably about 0.1 mg/kg to about 15 mg/kg per day for an average subject, depending upon the GPI and the route of administration. However, some variation in dosage will necessarily occur depending on the condition of the subject being treated. The individual responsible for dosing will, in any event, determine the appropriate dose for the individual subject.

Any sorbitol dehydrogenase inhibitor (SDI) may be used as the Second Agent in the combination compositions, combination therapies and kits of this invention. The term sorbitol dehydrogenase inhibitor refers to any substance or agent or any combination of substances and/or agents which reduces, retards, or eliminates the enzymatic action of sorbitol dehydrogenase. Sorbitol dehydrogenase catalyzes the oxidation of sorbitol to fructose.

SDIs are disclosed in commonly assigned U.S. Pat. Nos. 5,728,704, 5,866,578 and PCT application publication WO 00/59510.

The activity of SDIs may be evaluated using the assays and methods disclosed in commonly assigned PCT application publication WO 00/59510 and other assays and methods known by those skilled in the art.

SDIs are preferably administered in amounts ranging from about 0.001 mg/kg/day to about 100 mg/kg/day in single or divided doses, preferably about 0.01 mg/kg to about 10 mg/kg per day for an average subject, depending upon the SDI and the route of administration. However, some variation in dosage will necessarily occur depending on the condition of the subject being treated. The person responsible for administration will, in any event, determine the appropriate dose for the individual subject.

Any phosphodiesterase type 5 (PDE-5) inhibitor may be used as the Second Agent in the combination compositions, combination therapies and kits of this invention. The term phosphodiesterase type 5 inhibitor refers to any substance or agent or any combination of substances and/or agents which reduces, retards, or eliminates the enzymatic action of cyclic guanosine monophosphate (cGMP)-specific PDE-5. Such actions are readily determined by those skilled in the art according to assays as described in PCT application publication WO 00/24745.

The following patent publications exemplify phosphodiesterase type 5 inhibitors which can be used in the combination compositions, methods and kits of this invention, and refer to methods of preparing those phosphodiesterase type 5 (PDE-5) inhibitors: PCT application publication WO 00/24745; PCT application publication WO 94/28902; European Patent application publication 0463756A1; European Patent application publication 0526004A1 and European Patent application publication 0201188A2. A preferred phosphodiesterase type 5 inhibitor is sildenafil, which may be prepared as set forth in U.S. Pat. No. 5,250,534. The citrate salt of sildenafil, also known as Viagra®, which may be prepared as disclosed in U.S. Pat. No. 5,955,611, is even more preferred.

PDE-5 inhibitors are preferably administered in amounts ranging from about 5 mg/day to about 500 mg/day in single or divided doses, preferably about 10 mg/day to about 250 mg/day, for an average subject depending upon the PDE-5 inhibitor and the route of administration. However, some variation in dosage will necessarily occur depending on the condition of the subject being treated. The individual responsible for dosing will, in any event, determine the appropriate dose for the individual subject.

Any adenosine agonist may be used as the Second Agent in the combination compositions, combination therapies and kits of this invention. The term adenosine agonist refers to any substances and/or agents which pharmacologically affect the cardioprotective effects of ischemic preconditioning by activating adenosine A-3 receptors.

The utility of the adenosine agonists as medical agents in the treatment of cardiac tissue ischemia is demonstrated by the activity of said agonists in conventional preclinical cardioprotection assays [see the in vivo assay in Klein, H. et al., Circulation 92:912–917 (1995); the isolated heart assay in Tracey, W. R. et al., Cardiovascular Research 33:410–415 (1997); the antiarrhythmic assay in Yasutake M. et al., Am. J. Physiol., 36:H2430–H2440 (1994); the NMR assay in Kolke et al., J. Thorac. Cardiovasc. Surg. 112: 765–775 (1996)] and the additional in vitro and in vivo assays described below. Such assays also provide a means whereby the activities of adenosine agonists can be compared with the activities of other known compounds. The results of these comparisons are useful for determining dosage levels in mammals, including humans, for the treatment of such diseases.

Human Adenosine A1 and A3 Receptor Assays
Materials

Full-length human adenosine, $A_1$ and $A_3$ receptor cDNA's subcloned into the eukaryotic expression vector pRcCMV (Invitrogen) were purchased from The Garvan Institute, Sydney, Australia. Chinese hamster ovary (CHO-K1) cells were obtained from the American Type Tissue Culture Collection (Rockville, Md., USA). DMEM and DMEM/F12 culture media and foetal calf serum were obtained from Gibco-BRL (Grand Island, N.Y., USA). The A1/A3 adenosine receptor agonist N6-(4-amino-3-[125I]iodobenzyl) adenosine ($^{125}$I-ABA) was prepared by New England Nuclear (Boston, Mass., USA). Adenosine deaminase (ADA) was obtained from Boehringer Mannheim (Indianapolis, Ind., USA). The phosphodiesterase inhibitor RO-20-1724 was obtained from Research Biochemicals International (Natick, Mass., USA).

Expression of Human Adenosine A1 and A3 Receptors

For stable expression studies, adenosine receptor $A_1$ and $A_3$ expression plasmids (20 µg) are transfected into CHO-K1 cells, or HEK 293s cells, respectively, grown in DMEM/F12 (CHO) or DMEM (HEK 293s), with 10% foetal calf serum media, using a calcium phosphate mammalian cell transfection kit (5 Prime-3 Prime). Stable transfectants are obtained by selection in complete media containing 500 µg/ml (CHO) or 700 µg/ml (HEK 293s) active neomycin (G418) and screened for expression by [$^{125}$I]-ABA binding.

Receptor Membrane Preparation

Cells stably expressing either human $A_1$ or human $A_3$ receptors are collected by centrifugation at 300×g for 5 minutes, the supernatant is discarded and the cell pellet is resuspended in cell buffer consisting of (mmoles/L): HEPES (10), $MgCl_2$ (5), PMSF (0.1), bacitracin (100 µg/ml), leupeptin (10 µg/ml), DNAse I (100 µg/ml), ADA (2 U/ml), pH 7.4. Crude cell membranes are prepared by repeated aspiration through a 21 gauge needle, collected by centrifugation at 60,000×g for 10 minutes and stored in cell buffer at −80° C.

Estimation of Compound Binding Affinity Constants ($K_i$)

Receptor membranes are resuspended in incubation buffer consisting of (mmoles/L): HEPES (10), EDTA (1), $MgCl_2$ (5), pH 7.4. Binding reactions (10–20 µg membrane protein) are carried out for one hour at room temperature in 250 µl incubation buffer containing 0.1 nM of $^{125}$I-ABA (2200 Ci/mmol) and increasing concentrations of compound (0.1 nM–30 µM). The reaction is stopped by rapid filtration with ice-cold PBS, through glass fibre filters (presoaked in 0.6% polyethylenimine) using a Tomtec 96-well harvester (Orange, Conn., USA). Filters are counted in a Wallac Microbeta liquid scintillation counter (Gaithersberg, Md., USA). Nonspecific binding is determined in the presence of 5 µM I-ABA. Compound inhibitory constants ($K_i$) are calculated by fitting binding data via nonlinear least squares regression analysis to the equation: % Inhibition=100/[1+ ($10^C/10^X)^D$], where X=log[compound concentration], C($IC_{50}$)=log [compound concentration at 50% inhibition], and D=the Hill slope. At the concentration of radioligand used in the present study (10 fold<$K_D$), $IC_{50}$=$K_i$.

Assessment of Human Adenosine A3 Receptor Agonist Activity

Adenosine A3 agonist activity is assessed by compound inhibition of isoproterenol-stimulated cAMP levels. HEK293s cells stably transfected with human A3 receptors (as described above) are washed with Phosphate Buffered Saline (PBS) (Ca/Mg-free) and detached with 1.0 mM EDTA/PBS. Cells are collected by centrifugation at 300×g for 5 minutes and the supernatant discarded. The cell pellet is dispersed and resuspended in cell buffer (DMEM/F12 containing 10 mM HEPES, 20 µM RO-20-1724 and 1 U/ml ADA). Following preincubation of cells (100,000/well) for 10 min at 37° C., 1 µM isoproterenol, with or without increasing concentrations (0.1 nM–300 nM) test compound, and the incubation is continued for 10 min. Reactions are terminated by the addition of 1.0 N HCl followed by centrifugation at 2000×g for 10 minutes. Sample supernatants (10 µl) are removed and cAMP levels determined by radioimmunoassay (New England Nuclear, Boston, Mass., USA). The basal and control isoproterenol-stimulated cAMP accumulation (pmol/ml/100,000 cells) are routinely 3 and 80, respectively. Smooth curves are fitted to the data via nonlinear least squares regression analysis to the equation: % isoproterenol-stimulated cAMP=100/[1+($10^X/10^C)^D$], where X=log [compound concentration], C($IC_{50}$)=log [compound concentration at 50% inhibition], and D=the Hill slope.

The therapeutic effects of the compounds of this invention in preventing heart tissue damage resulting from an ischemic insult can be demonstrated in vitro along lines presented in Tracey et al. (Cardiovasc. Res., 33:410–415, 1997).

The following patent publications exemplify adenosine agonists which can be used in the combination compositions, methods and kits of this invention, and refer to methods of preparing those adenosine agonists: U.S. Pat. Nos. 5,604,210; 5,688,774; 5,773,423; J. Med. Chem. 1994, 37, 636–646; J. Med. Chem. 1995, 38, 1174–1188; J. Med. Chem. 1995, 38, 1720–1735.

U.S. Pat. No. 5,817,760 discloses recombinant human adenosine receptors A1, A2a, A2b, and A3 which were prepared by cDNA cloning and polymerase chain reaction techniques. The recombinant adenosine receptors can be utilized in an assay to identify and evaluate entities that bind to or enhance binding to adenosine receptors.

Adenosine agonists are preferably administered in amounts ranging from about 0.001 mg/kg/day to about 100 mg/kg/day, for an average subject depending upon the adenosine agonist and the route of administration. An especially preferred dosage is about 0.01 mg/kg/day to about 50 mg/kg/day of an adenosine agonists. However, some variation in dosage will necessarily occur depending upon the condition of the subject being treated. The individual responsible for dosing will, in any event, determine the appropriate dose for the individual subject.

Any NHE-1 inhibitor may be used as the Second Agent in the combination compositions, combination therapies and kits of this invention. The term NHE-1 inhibitor refers to compounds which inhibit the sodium/proton ($Na^+/H^+$) exchange transport system and hence are useful as a therapeutic or prophylactic agent for diseases caused or aggravated by the acceleration of the sodium/proton ($Na^+/H^+$) exchange transport system, for example, cardiovascular diseases [e.g., arteriosclerosis, hypertension, arrhythmia (e.g. ischemic arrhythmia, arrhythmia due to myocardial infarction, myocardial stunning, myocardial dysfunction, arrhythmia after PTCA or after thrombolysis, etc.), angina pectoris, cardiac hypertrophy, myocardial infarction, heart failure (e.g. congestive heart failure, acute heart failure, cardiac hypertrophy, etc.), restenosis after PTCA, PTCI, shock (e.g. hemorrhagic shock, endotoxin shock, etc.)], renal diseases (e.g. diabetes mellitus, diabetic nephropathy, ischemic acute renal failure, etc.) organ disorders associated with ischemia or ischemic reperfusion [e.g. heart muscle ischemic reperfusion associated disorders, acute renal failure, or disorders induced by surgical treatment such as coronary artery bypass grafting (CABG) surgeries, vascular surgeries, organ transplantation, non-cardiac surgeries or percutaneous transluminal coronary angioplasty (PTCA)], cerebrovascular diseases (e.g. ischemic stroke, hemorrhagic stroke, etc.), cerebro ischemic disorders (e.g. disorders associated with cerebral infarction, disorders caused after cerebral apoplexy as sequelae, or cerebral edema. NHE-1 inhibitors can also be used as an agent for myocardial protection during coronary artery bypass grafting (CABG) surgeries, vascular surgeries, percutaneous transluminal coronary angioplasty (PTCA), PTCI, organ transplantation, or non-cardiac surgeries.

The utility of the combination of compounds of the present invention with NHE-1 inhibitors as medical agents in the treatment of diseases, such as are detailed herein in mammals (e.g. humans) for example, myocardial protection during surgery or mycardial protection in patients presenting with ongoing cardiac or cerebral ischemic events or chronic cardioprotection in patients with diagnosed coronary heart disease, or at risk for coronary heart disease, cardiac dysfunction or myocardial stunning is demonstrated by the activity of said combination in conventional preclinical cardioprotection assays [see the in vivo assay in Klein, H. et al., Circulation 92:912–917 (1995); the isolated heart assay in Scholz, W. et al., Cardiovascular Research 29:260–268 (1995); the antiarrhythmic assay in Yasutake M. et al., Am. J. Physiol., 36:H2430–H2440 (1994); the NMR assay in Kolke et al., J. Thorac. Cardiovasc. Surg. 112: 765–775 (1996)] and the additional in vitro and in vivo assays described below. Such assays also provide a means whereby the activities of the compounds of formula I of this invention can be compared with the activities of other known compounds. The results of these comparisons are useful for determining dosage levels in mammals, including humans, for the treatment of such diseases.

The following patent publications exemplify NHE-1 inhibitors which can be used in the combination compositions, methods and kits of this invention, and refer to methods of preparing those NHE-1 inhibitors: U.S. Pat. No. 5,698,581, European Patent Application Publication No. EP 803 501 A1, International Patent Application Publication Nos. WO 94/26709 and PCT/JP97/04650.

Preferred NHE-1 inhibitors include compounds of the formula NHE,

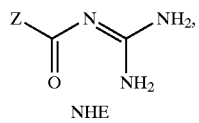

NHE a prodrug thereof or a pharmaceutically acceptable salt of said compound or of said prodrug, wherein Z in the compound of formula NHE is carbon connected and is a five-membered, diaza, diunsaturated ring having two contiguous nitrogens, said ring optionally mono-, di-, or tri-substituted with up to three substituents independently selected from $R^1$, $R^2$ and $R^3$; or Z in the compound of formula NHE carbon connected and is a five-membered, triaza, diunsaturated ring, said ring optionally mono- or di-substituted with up to two substituents independently selected from $R^4$ and $R^5$;

wherein $R^1$, $R^2$, $R^3$, $R^4$ and $R^5$ in the compound of formula NHE are each independently hydrogen, hydroxy-$(C_1-C_4)$alkyl, $(C_1-C_4)$alkyl, $(C_1-C_4)$alkylthio, $(C_3-C_4)$cycloalkyl, $(C_3-C_7)$cycloalkyl$(C_1-C_4)$alkyl, $(C_1-C_4)$alkoxy, $(C_1-C_4)$alkoxy$(C_1-C_4)$alkyl, mono-N— or di-N,N—$(C_1-C_4)$alkylcarbamoyl, M or M$(C_1-C_4)$alkyl, any of said previous $(C_1-C_4)$alkyl moieties optionally having from one to nine fluorines; said $(C_1-C_4)$alkyl or $(C_3-C_4)$cycloalkyl optionally mono- or di-substituted independently with hydroxy, $(C_1-C_4)$alkoxy, $(C_1-C_4)$alkylthio, $(C_1-C_4)$alkylsulfinyl, $(C_1-C_4)$alkylsulfonyl, $(C_1-C_4)$alkyl, mono-N— or di-N,N—$(C_1-C_4)$alkylcarbamoyl or mono-N— or di-N,N—$(C_1-C_4)$alkylaminosulfonyl; and said $(C_3-C_4)$cycloalkyl optionally having from one to seven fluorines;

wherein M in the compound of formula NHE is a partially saturated, fully saturated or fully unsaturated five to eight membered ring optionally having one to three heteroatoms selected independently from oxygen, sulfur and nitrogen, or, a bicyclic ring consisting of two fused partially saturated, fully saturated or fully unsaturated three to six membered rings, taken independently, optionally having one to four heteroatoms selected independently from nitrogen, sulfur and oxygen;

said M in the compound of formula NHE is optionally substituted, on one ring if the moiety is monocyclic, or one or both rings if the moiety is bicyclic, on carbon or nitrogen with up to three substituents independently selected from $R^6$, $R^7$ and $R^8$, wherein one of $R^6$, $R^7$ and $R^8$ is optionally a partially saturated, fully saturated, or fully unsaturated three to seven membered ring optionally having one to three heteroatoms selected independently from oxygen, sulfur and nitrogen optionally substituted with $(C_1-C_4)$alkyl and additionally $R^6$, $R^7$ and $R^8$ are optionally hydroxy, nitro, halo, $(C_1-C_4)$alkoxy, $(C_1-C_4)$alkoxycarbonyl, $(C_1-C_4)$alkyl, formyl, $(C_1-C_4)$alkanoyl, $(C_1-C_4)$alkanoyloxy, $(C_1-C_4)$alkanoylamino, $(C_1-C_4)$alkoxycarbonylamino, sulfonamido, $(C_1-C_4)$alkylsulfonamido, amino, mono-N— or di-N,N—$(C_1-C_4)$alkylamino, carbamoyl, mono-N— or di-N,N—$(C_1-C_4)$alkylcarbamoyl, cyano, thiol, $(C_1-C_4)$alkylthio, $(C_1-C_4)$alkylsulfinyl, $(C_1-C_4)$alkylsulfonyl, mono-N— or di-N,N—$(C_1-C_4)$alkylaminosulfonyl, $(C_2-C_4)$alkenyl, $(C_2-C_4)$alkynyl or $(C_5-C_7)$cycloalkenyl, wherein said $(C_1-C_4)$alkoxy, $(C_1-C_4)$alkyl, $(C_1-C_7)$alkanoyl, $(C_1-C_4)$alkylthio, mono-N— or di-N,N—$(C_1-C_4)$alkylamino or $(C_3-C_7)$cycloalkyl $R^6$, $R^7$ and $R^8$ substituents are optionally mono-substituted independently with hydroxy, $(C_1-C_4)$alkoxycarbonyl, $(C_3-C_7)$cycloalkyl, $(C_1-C_4)$alkanoyl, $(C_1-C_4)$alkanoylamino, $(C_1-C_4)$alkanoyloxy, $(C_1-C_4)$alkoxycarbonylamino, sulfonamido, $(C_1-C_4)$alkylsulfonamido, amino, mono-N— or di-N,N—$(C_1-C_4)$alkylamino, carbamoyl, mono-N— or di-N,N—$(C_1-C_4)$alkylcarbamoyl, cyano, thiol, nitro, $(C_1-C_4)$alkylthio, $(C_1-C_4)$alkylsulfinyl, $(C_1-C_4)$ alkylsulfonyl or mono-N— or di-N,N—($C_1$–$C_4$) alkylaminosulfonyl or optionally substituted with one to nine fluorines.

Especially preferred NHE-1 inhibitors include [1-(8-bromoquinolin-5-yl)-5-cyclopropyl-1H-pyrazole-4-carbonyl]guanidine; [1-(6-chloroquinolin-5-yl)-5-cyclopropyl-1H-pyrazole-4-carbonyl]guanidine; [1-(indazol-7-yl)-5-cyclopropyl-1H-pyrazole-4-carbonyl]guanidine; [1-(benzimidazol-5-yl)-5-cyclopropyl-1H-pyrazole-4-carbonyl]guanidine; [1-(1-isoquinolyl)-5-cyclopropyl-1H-pyrazole-4-carbonyl]guanidine; [5-cyclopropyl-1-(4-quinolinyl)-1H-pyrazole-4-carbonyl]guanidine; [5-cyclopropyl-1-(quinolin-5-yl)-1H-pyrazole-4-carbonyl]guanidine; [5-cyclopropyl-1-(quinolin-8-yl)-1H-pyrazole-4-carbonyl]guanidine; [1-(indazol-6-yl)-5-ethyl-1H-pyrazole-4-carbonyl]guanidine; [1-(indazol-5-yl)-5-ethyl-1H-pyrazole-4-carbonyl]guanidine; [1-(benzimidazol-5-yl)-5-ethyl-1H-pyrazole-4-carbonyl]guanidine; [1-(1-methylbenzimidazol-6-yl)-5-ethyl-1H-pyrazole-4-carbonyl]guanidine; 1-(5-quinolinyl)-5-n-propyl-1H-pyrazole-4-carbonyl]guanidine; [1-(5-quinolinyl)-5-isopropyl-1H-pyrazole-4-carbonyl]guanidine; [5-ethyl-1-(6-quinolinyl)-1H-pyrazole-4-carbonyl]guanidine; [1-(2-methylbenzimidazol-5-yl)-5-ethyl-1H-pyrazole-4-carbonyl]guanidine; [1-(1,4-benzodioxan-6-yl)-5-ethyl-1H-pyrazole-4-carbonyl]guanidine; [1-(benzotriazol-5-yl)-5-ethyl-1H-pyrazole-4-carbonyl]guanidine; [1-(3-chloroindazol-5-yl)-5-ethyl-1H-pyrazole-4-carbonyl]guanidine; [1-(5-quinolinyl)-5-butyl-1H-pyrazole-4-carbonyl]guanidine; [5-propyl-1-(6-quinolinyl)-1H-pyrazole-4-carbonyl]guanidine; [5-isopropyl-1-(6-quinolinyl)-1H-pyrazole-4-carbonyl]guanidine; [1-(2-chloro-4-methylsulfonylphenyl)-5-cyclopropyl-1H-pyrazole-4-carbonyl]guanidine; [1-(2-chlorophenyl)-5-cyclopropyl-1H-pyrazole-4-carbonyl]guanidine; [1-(2-trifluoromethyl-4-fluorophenyl)-5-cyclopropyl-1H-pyrazole-4-carbonyl]guanidine; [1-(2-bromophenyl)-5-cyclopropyl-1H-pyrazole-4-carbonyl]guanidine; [1-(2-fluorophenyl)-5-cyclopropyl-1H-pyrazole-4-carbonyl]guanidine; [1-(2-chloro-5-methoxyphenyl)-5-cyclopropyl-1H-pyrazole-4-carbonyl]guanidine; [1-(2-chloro-4-methylaminosulfonylphenyl)-5-cyclopropyl-1H-pyrazole-4-carbonyl]guanidine; [1-(2,5-dichlorophenyl)-5-cyclopropyl-1H-pyrazole-4-carbonyl]guanidine; [1-(2,3-dichlorophenyl)-5-cyclopropyl-1H-pyrazole-4-carbonyl]guanidine; [1-(2-chloro-5-aminocarbonylphenyl)-5-cyclopropyl-1H-pyrazole-4-carbonyl]guanidine; [1-(2-chloro-5-aminosulfonylphenyl)-5-cyclopropyl-1H-pyrazole-4-carbonyl]guanidine; [1-(2-fluoro-6-trifluoromethylphenyl)-5-cyclopropyl-1H-pyrazole-4-carbonyl]guanidine; [1-(2-chloro-5-methylsulfonylphenyl)-5-cyclopropyl-1H-pyrazole-4-carbonyl]guanidine; [1-(2-chloro-5-dimethylaminosulfonylphenyl)-5-cyclopropyl-1H-pyrazole-4-carbonyl]guanidine; [1-(2-trifluoromethyl-4-chlorophenyl)-5-cyclopropyl-1H-pyrazole-4-carbonyl]guanidine; [1-(2-chlorophenyl)-5-methyl-1H-pyrazole-4-carbonyl]guanidine; [5-methyl-1-(2-trifluoromethylphenyl)-1H-pyrazole-4-carbonyl]guanidine; [5-ethyl-1-phenyl-1H-pyrazole-4-carbonyl]guanidine; [5-cyclopropyl-1-(2-trifluoromethylphenyl)-1H-pyrazole-4-carbonyl]guanidine; [5-cyclopropyl-1-phenyl-1H-pyrazole-4-carbonyl]guanidine; [5-cyclopropyl-1-(2,6-dichlorophenyl)-1H-pyrazole-4-carbonyl]guanidine or or a pharmaceutically acceptable salt thereof.

The preferred and especially preferred NHE-1 inhibitors disclosed in the above two paragraphs can be prepared according to methods set forth in International Patent Application No. PCT/IB99/00206.

NHE-1 inhibitors are preferably administered in amounts ranging from about 0.001 mg/day to about 100 mg/day, for an average subject depending upon the NHE-1 inhibitor and the route of administration. However, some variation in dosage will necessarily occur depending upon the condition of the subject being treated. An especially preferred dosage contains about 0.01 to 50 mg/day of said NHE-1 inhibitor. The individual responsible for dosing will, in any event, determine the appropriate dose for the individual subject.

As used herein, the term "effective amount" refers to an amount of compound or compounds of the present invention which is capable of inhibiting or preventing diabetic complications and/or cardiac tissue ischemia, herein described. The terms "inhibit" or "inhibiting" refers to prohibiting, treating, alleviating, ameliorating, halting, restraining, slowing or reversing the progression, or reducing the severity of a complication resulting from diabetes, in patients who are at risk for such complications. As such, these methods include both medical therapeutic (acute) and/or prophylactic (prevention) administration as appropriate. The amount and timing of compounds administered will, of course, be dependent on the subject being treated, on the severity of the affliction, on the manner of administration and on the judgement of the prescribing physician. Thus, because of patient to patient variability, the dosages given above are a guideline and the physician may titrate doses of the drug to achieve the treatment that the physician considers appropriate for the patient. In considering the degree of treatment desired, the physician must balance a variety of factors such as age of the patient, presence of preexisting disease, as well as presence of other diseases.

In the aspects of this invention related to therapeutic methods of treating or preventing diabetic complications wherein a compound of Formula I of this invention and a Second Agent are administered together as part of the same pharmaceutical composition and to methods wherein these two agents are administered separately, the appropriate dosage regimen, the amount of each dose administered and the intervals between doses of the active agents will again depend upon the compound of Formula I of this invention and the Second Agent being used, the type of pharmaceutical compositions being used, the characteristics of the subject being treated and the severity of the condition or conditions.

Administration of the compounds and pharmaceutical compositions of this invention may be performed via any method which delivers a compound or composition of this invention preferentially to the desired tissue (e.g., nerve, kidney, lens, retina and/or cardiac tissues). These methods include oral routes, parenteral, intraduodenal routes, etc, and may be administered in single (e.g., once daily) or multiple doses or via constant infusion.

The pharmaceutical compositions of this invention may be administered to a subject in need of treatment by a variety of conventional routes of administration, including orally, topically, parenterally, e.g., intravenously, rectally, subcutaneously or intramedullary. Further, the pharmaceutical compositions of this invention may be administered intranasally, as a suppository or using a "flash" formulation, i.e., allowing the medication to dissolve in the mouth without the need to use water.

The compounds of this invention may be administered alone or in combination with pharmaceutically acceptable carriers, vehicles or diluents, in either single or multiple doses. Suitable pharmaceutical carriers, vehicles and diluents include inert solid diluents or fillers, sterile aqueous solutions and various organic solvents. The pharmaceutical compositions formed by combining the compounds of this invention and the pharmaceutically acceptable carriers, vehicles or diluents are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and/or calcium phosphate may be employed along with various disintegrants such as starch, alginic acid and/or certain complex silicates, together with binding agents such as polyvinylpyrrolidone, sucrose, gelatin and/or acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the active pharmaceutical agent therein may be combined with various sweetening or flavoring agents, coloring matter or dyes and, if desired, emulsifying or suspending agents, together with diluents such as water, ethanol, propylene glycol, glycerin and/or combinations thereof.

For parenteral administration, solutions of the compounds of this invention in sesame or peanut oil, aqueous propylene glycol, or in sterile aqueous solutions may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, the sterile aqueous media employed are all readily available by standard techniques known to those skilled in the art.

Generally, a composition of this invention is administered orally, or parenterally (e.g., intravenous, intramuscular, subcutaneous or intramedullary). Topical administration may also be indicated, for example, where the patient is suffering from gastrointestinal disorders or whenever the medication is best applied to the surface of a tissue or organ as determined by the attending physician.

Buccal administration of a composition of this invention may take the form of tablets or lozenges formulated in a conventional manner.

For intranasal administration or administration by inhalation, the compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of a compound of this invention. Capsules and cartridges (made, for example, from gelatin) for use in an inhaler or insufflator may be formulated containing a powder mix of a compound or compounds of the invention and a suitable powder base such as lactose or starch.

For purposes of transdermal (e.g., topical) administration, dilute sterile, aqueous or partially aqueous solutions (usually in about 0.1% to 5% concentration), otherwise similar to the above parenteral solutions, are prepared.

Methods of preparing various pharmaceutical compositions with a certain amount of active ingredient are known, or will be apparent in light of this disclosure, to those skilled in this art. For examples of methods of preparing pharmaceutical compositions, see *Remington's Pharmaceutical Sciences*, Mack Publishing Company, Easton, Pa., 19th Edition (1995).

In the aspects of this invention related to the combination compositions, wherein the compositions contain an amount of both a compound of Formula I of this invention and a Second Agent, the amount of each such ingredient may independently be 0.0001%–95% of the total amount of the composition, provided, of course, that the total amount does not exceed 100%. In any event, the composition or formulation to be administered will contain a quantity of each of the components of the composition according to the invention in an amount effective to treat the disease/complications of the subject being treated.

Since the present invention has an aspect that relates to the treatment of the disease/complications described herein with a combination of active ingredients which may be administered separately, the invention also relates to combining separate pharmaceutical compositions in kit form. The kit comprises two separate pharmaceutical compositions: a compound of Formula I a prodrug thereof or a pharmaceutically acceptable salt of such compound or prodrug and a Second Agent as described above. The kit comprises a container for containing the separate compositions such as a divided bottle or a divided foil packet. Typically the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

An example of such a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of the tablets or capsules to be packed. Next, the tablets or capsules are placed in the recesses and the sheet of relatively stiff material is sealed against the plastic foil at the face of the foil which is opposite from the direction in which the recesses were formed. As a result, the tablets or capsules are sealed in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide a memory aid on the kit, e.g., in the form of numbers next to the tablets or capsules whereby the numbers correspond with the days of the regimen which the tablets or capsules so specified should be ingested. Another example of such a memory aid is a calendar printed on the card, e.g., as follows "First Week, Monday, Tuesday, . . . etc. . . . Second Week, Monday, Tuesday, . . . " etc. Other variations of memory aids will be readily apparent. A "daily dose" can be a single tablet or capsule or several pills or capsules to be taken on a given day. Also, a daily dose of a compound of Formula I of this invention can consist of one tablet or capsule while a daily dose of the Second Agent can consist of several tablets or capsules and vice versa. The memory aid should reflect this.

In another specific embodiment of the invention, a dispenser designed to dispense the daily doses one at a time in the order of their intended use is provided. Preferably, the dispenser is equipped with a memory-aid, so as to further facilitate compliance with the regimen. An example of such a memory-aid is a mechanical counter which indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

The journal articles and scientific references, patents and patent application publications cited above are wholly incorporated herein by reference.

General Experimental Procedures

Melting points were determined on a Thomas-Hoover capillary melting point apparatus, and are uncorrected. Low-resolution mass spectra were obtained under thermospray (TS) conditions on a Fisons (now Micromass) Trio 1000 Mass Spectrometer (Micromass Inc., Beverly, Mass.), under chemical-ionization (CI) conditions on a Hewlett Packard 5989A Particle Beam Mass Spectrometer (Hewlett Packard Co., Palo Alto, Calif.), or under atmospheric pressure chemical ionization (APCI) on a Fisons (now Micromass) Platform II Spectrometer.

EXAMPLE 1

6-(Indole-2-sulfonyl)-2H-pyridazin-3-one

Step A: 3-Methoxy-6-(indole-2-sulfenyl)-pyridazine. To a solution of 2-mercaptoindole (6.7 mmol, 1.0 g) in acetone (20 mL) was added 2-chloro-6-methoxy-pyridazine (144 mmol, 1.52 g) and potassium carbonate (70 mmol, 0.98 g) and the reaction mixture was refluxed for 2 hours. Excess acetone was removed and the residue was partitioned between $CHCl_3$ (20 mL) and $H_2O$ (20 mL). The $CHCl_3$ layer was collected, dried, filtered and the filtrate was evaporated to a residue, which was purified by silica gel chromatography (eluent:hexanes:EtOAc::4:1) to obtain 3-methoxy-6-(indole-2-sulfenyl)-pyridazine (31%, 534 mg).

Step B: 3-Methoxy-6-(indole-2-sulfonyl)-pyridazine. To a solution of 3-methoxy-6-(indole-2-sulfenyl)-pyridazine (1.9 mmol, 488 mg) in $CHCl_3$ (20 mL) was added meta-chloroperbenzoic acid (MCPBA, 4.1 mmol, 1.0 g) and the reaction mixture was stirred overnight at room temperature. The reaction mixture was filtered and the filtrate was washed with saturated sodium bicarbonate solution (20 mL) and $H_2O$ (20 mL). The chloroform layer was collected, filtered, dried and the filtrate was evaporated to a residue, which was purified by silica gel chromatography (eluent:hexanes:EtOAc::3:1) to obtain the desired product, 3-methoxy-6-(indole-2-sulfonyl)-pyridazine (33%, 180 mg).

Step C: 6-(Indole-2-sulfonyl)-2H-pyridazin-3-one. A mixture of 3-methoxy-6-(indole-2-sulfonyl)-pyridazine (0.58 mmol, 290 mg), conc. HCl (0.5 mL), and dioxane (3 mL) was heated at 100° C. for 2 hours. The reaction mixture was cooled and evaporated to dryness. Water (10 mL) was added to the residue, and the resulting solid, 6-(indole-2-sulfonyl)-pyridazin-3-one was collected and dried (83%, 133 mg); mp 248° C.–249° C.

EXAMPLE 2

6-(5-Chloro-3-methyl-benzofuran-2-sulfonyl)-2H-pyridazin-3-one

Step A: 5-Chloro-2-mercapto-3-methyl benzofuran. n-Butyl lithium (2.5 M in hexane, 0.09 mol, 33 mL) was added dropwise over 15 minutes to a solution of 5-chloro-3-methylbenzofuran (which was prepared as described in J. Chem. Soc., 1965, 744–777, 0.09 mol, 369 mg) in tetrahydrofuran (THF, 160 mL) cooled to −78° C. To this was added sulfur powder (0.09 mol, 2.7 g) and the reaction mixture was stirred for 10 minutes. The reaction mixture was allowed to come to room temperature and was then quenched with ether (200 mL) and $H_2O$ (500 mL). Sufficient 10% HCl was added to adjust the pH to 7. The ether layer was collected, dried, filtered and the filtrate was evaporated to dryness to obtain a pale yellow solid, 5-chloro-2-mercapto-3-methyl benzofuran (90%, 15.1 g).

Step B: 6-(5-Chloro-3-methyl-benzofuran-2-sulfenyl)-pyridazine. To a solution containing 5-chloro-2-mercapto-3-methyl benzofuran (10 mmol, 1.98 g and 3-chloro-6-methoxy pyridazine (10 mmol, 1.44 g) in dimethylformamide (DMF, 10 mL) was added potassium carbonate (20 mmol, 2.76 g) and the reaction mixture was stirred at room temperature for 3 hours. The reaction mixture was quenched with $H_2O$ (200 mL), the precipitated yellow solid was collected and the solid was purified by silica gel chromatography (eluent:hexanes:EtOAc::9:1) to obtain 6-(5-chloro-3-methyl-benzofuran-2-sulfenyl)-pyridazine (93%, 2.87 g); mp 131° C.–134° C.

Step C: 6-(5-Chloro-3-methyl-benzofuran-2-sulfenyl)-2-H-pyridazin-3-one. A mixture of 6-(5-chloro-3-methyl-benzofuran-2-sulfenyl)-pyridazine (1.6 mmol, 500 mg), conc. HCl (1 mL), and dioxane (5 mL) was heated at 100° C. for 2 hours. The reaction mixture was cooled and evaporated to dryness. Water (10 mL) was added to the residue, and the resulting white precipitate was collected and crystallized from ethanol to obtain the desired product, 6-(5-chloro-3-methyl-benzofuran-2-sulfenyl)-2-H-pyridazin-3-one (73%, 113 mg); mp>240° C.

Step D: 6-(5-Chloro-3-methyl-benzofuran-2-sulfonyl)-2-H-pyridazin-3-one. To a mixture of 6-(5-chloro-3-methyl-benzofuran-2-sulfenyl)-2-H-pyridazin-3-one, and acetic acid (30 mL) was added peracetic acid (33 mmol, 7.8 mL). The reaction mixture was allowed to stir overnight and the precipitated solid was collected and washed with $H_2O$. The solid was air dried and crystallized from methanol to give 6-(5-chloro-3-methyl-benzofuran-2-sulfonyl)-2H-pyridazin-3-one, (37%, 1.81 g). mp 247° C.–248° C.

EXAMPLE 3

6-(5-Chloro-3-methyl-benzofuran-2-sulfonyl)-2H-pyridazin-3-one

Step A: 3-Methoxy-6-(5-chloro-3-methyl-benzofuran-2-sulfonyl)-pyridazine. n-Butyl lithium (2.5 M in hexane, 1.2 mmol, 0.48 mL) was added dropwise over 15 minutes to a solution of 5-chloro-2-methyl benzofuran (which was prepared as described in J. Chem. Soc., 1965, 744–777, 1.92 mmol, 369 mg) in THF (6 mL) cooled to −78° C. To this was added 2-fluorosulfonyl-4-methoxy-pyridazine (1.92 mmol, 320 mg) and was stirred for 30 minutes. The reaction mixture was allowed to come to room temperature overnight and then quenched with EtOAc (20 mL) and $H_2O$ (10 mL). The organic portion was collected, dried, filtered and the filtrate was evaporated to dryness to obtain a crude product, which was purified by silica gel chromatography (eluent:hexanes:EtOAc::3:2) to obtain the desired product: 3-methoxy-6-(5-chloro-3-methyl-benzofuran-2-sulfonyl)-pyridazine (22%, 166 mg).

Step B: 6-(3-Methyl-benzofuran-2-sulfonyl)-2H-pyridazin-3-one. A mixture of 3-methoxy-6-(5-chloro-3- methyl-benzofuran-2-sulfonyl)-pyridazine (0.5 mmol, 162 mg), conc. HCl (1 mL), and dioxane (3 mL) was heated at 100° C. for 2 hours. The reaction mixture was cooled and evaporated to dryness. Water (10 mL) was added to the residue. The resulting yellow precipitate was collected and crystallized from ethanol to obtain the desired product: 6-(3-methyl-benzofuran-2-sulfonyl)-2H-pyridazin-3-one (73%, 113 mg); mp 247° C.–248° C.

EXAMPLE 4

6-(5-Chloro-3-methyl-benzofuran-2-sulfonyl)-2H-pyridazin-3-one

Step A: 3-Methoxy-6-(5-chloro-3-methyl-benzofuran-2-sulfonyl)-pyridazine. n-Butyl lithium (2.5 M in hexane, 33 mmol, 13.2 mL) was added dropwise over 15 minutes to a solution of 5-chloro-2-methyl benzofuran (which was prepared as described in J. Chem. Soc., 1965, 744–777, 1.92 mmol, 369 mg) in THF (30 mL) cooled to from between −50° C. to −35° C. This was transferred into a cold-jacketed addition funnel and added drop-wise to a solution of 3-fluorosulfonyl-6-methoxypyridazine (30 mmol, 5.76 g) in THF (30 mL) over 10 minutes. The reaction mixture was allowed to come to room temperature, excess solvents were removed, and the residue was quenched with $H_2O$ (500 mL). The granulated solid was filtered and air dried to obtain 3-methoxy-6-(5-chloro-3-methyl-benzofuran-2-sulfonyl)-pyridazine (75%, 7.62 g).

Step B: 6-(5-Chloro-3-methyl-benzofuran-2-sulfonyl)-2H-pyridazin-2H-pyridazin-3-one. A mixture of 3-methoxy-6-(5-chloro-3-methyl-benzofuran-2-sulfonyl)-pyridazine (22.2 mmol, 7.5 g), conc. HCl (5 mL), and dioxane (50 mL) was heated at 100° C. for 2 hours. The reaction mixture was cooled and evaporated to dryness. Water (20 mL) was added to the residue. The resulting precipitate was collected and crystallized from ethanol to obtain the desired product: 6-(5-chloro-3-methyl-benzofuran-2-sulfonyl)-2H-pyridazin-2H-pyridazin-3-one (89%, 6.42 g).

EXAMPLE 5

6-(Benzofuran-2-sulfonyl)-2H-pyridazin-3-one

The title compound of Example 5 was prepared from benzofuran in a manner analogous to the method of Example 3. (10%); mp 210° C.–211° C.

EXAMPLE 6

6-(5-Methoxy-benzofuran-2-sulfonyl)-2H-pyridazin-3-one

The title compound of Example 6 was prepared from 5-methoxybenzofuran in a manner analogous to the method of Example 3. (28%); mp 222° C.–223° C.

EXAMPLE 7

6-(3,5-Dimethyl-benzofuran-2-sulfonyl)-2H-pyridazin-3-one

The title compound of Example 7 was prepared from 3,5-dimethylbenzofuran in a manner analogous to the method of Example 3. (68%); mp 246° C.–247° C.

EXAMPLE 8

6-(5,7-Dichloro-benzofuran-2-sulfonyl)-2H-pyridazin-3-one

The title compound of Example 8 was prepared from 5,7-dichloro-benzofuran in a manner analogous to the method of Example 3. mp 240° C.–245° C.

EXAMPLE 9

6-(5-Chloro-benzofuran-2-sulfonyl)-2H-pyridazin-3-one

The title compound of Example 9 was prepared from 5-chlorobenzofuran in a manner analogous to the method of Example 5. (68%); mp 246–247° C.

EXAMPLE 10

6-(4-Chloro-3-methyl-benzofuran-2-sulfonyl)-2H-pyridazin-3-one

The title compound of Example 10 was prepared from 4-chloro-3-methyl benzofuran in a manner analogous to the method of Example 5. (25%, mp 232° C.–233° C.).

EXAMPLE 11

6-(3-Methyl-benzofuran-2-sulfonyl)-2H-pyridazin-3-one

Step A: 3-Methoxy-6-(3-methyl-benzofuran-2-sulfonyl)-pyridazine. A solution of 2-bromo-3-methyl benzofuran (Helv. Chim. Acta, 1948, 31, 78) (1.34 mmol, 283 mg) in THF (5 mL) was cooled to −78° C. and n-butyl lithium (2.5 M in hexane, 1.47 mmol, 0.6 mL) was added dropwise. The reaction mixture was stirred for 30 minutes and 2-fluorosulfonyl-4-methoxy-pyridazine (1.34 mmol, 257 mg) was added. The reaction mixture was allowed to come to room temperature overnight and was diluted with EtOAc (20 mL) and $H_2O$ (10 mL). The organic portion was collected, dried, filtered and the filtrate was evaporated to dryness to obtain a brown oil, 3-methoxy-6-(3-methyl-benzofuran-2-sulfonyl)-pyridazine (52%, 212 mg).

Step B: 6-(3-Methyl-benzofuran-2-sulfonyl)-2H-pyridazin-3-one. A mixture of the above product (0.73 mmol, 212 mg), conc. HCl (2 mL), and dioxane (3 mL) was heated at 100° C. for 2 hours. The reaction mixture was cooled and evaporated to dryness to obtain a crude product, which was purified by silica gel chromatography (eluent:EtOAc:hexanes::1:1), to obtain 6-(3-methyl-benzofuran-2-sulfonyl)-2H-pyridazin-3-one (31%, 65 mg); mp 182° C.–183° C.

EXAMPLE 12

6-(5-Trifluoromethyl-3-methyl-benzofuran-2-sulfonyl)-2H-pyridazin-3-one

Step A: α,α,α-Trifluoro-o-iodo-p-cresol. A mixture of iodine (91.6 mmol, 23.2 g) and sodium bicarbonate (91.6 mmol, 7.7 g) was added to a solution of α,α,α-trifluoro-p-cresol (83.3 mmol, 13.5 g) in THF (90 mL) and $H_2O$ (90 mL) and the reaction mixture was allowed to stand at room temperature overnight. Sufficient thiourea (5% solution) was added to remove the excess iodine as indicated by the color change of the reaction from deep violet to brown. The reaction mixture was extracted with ether (3×100 mL), the extract was dried, filtered and the filtrate was concentrated to obtain a brown oil. This oil was distilled (bp 105° C. at 44 mm Hg) to obtain α,α,α-trifluoro-o-iodo-p-cresol (4.1 g, 75% pure, admixed with the starting α,α,α-trifluoro-p-cresol).

Step B: To a mixture of the above 75% pure α,α,α-trifluoro-o-iodo-p-cresol (4.1 g, 17 mmol), potassium carbonate (7.7 g), and DMF (120 mL) was added allyl bromide (6.8 g). After 3 hours the reaction mixture was poured into H₂O (100 mL) and extracted with ether (2×100 mL). The ether layer was collected, dried, filtered and the filtrate was concentrated to obtain a brown oil. This oil was distilled (bp, 95–100° C. at 20 mm Hg) to obtain a mixture (3:1) of allyl compounds.

Step C: 3-Methyl-5-trifluoromethyl benzofuran. To a mixture of the above allyl compounds (3.9 g, 8.83 mmol of the desired isomer), sodium carbonate (22.1 mmol, 2.3 g), sodium formate (8.83 mmol, 0.81 g), n-butyl ammonium chloride (9.72 mmol, 2.7 g) and DMF (15 mL) was added palladium di-acetate (0.44 mmol, 0.1 g). The reaction mixture was heated to 80° C. and maintained at that temperature overnight. The reaction mixture was cooled to room temperature, filtered and the filtrate was dried and evaporated to give a crude product, which was purified by silica gel chromatography (eluent:hexanes) to obtain 3-methyl-5-trifluoromethyl benzofuran as a clear oil (44%, 780 mg).

Step D: 3-Methoxy-6-(5-trifluoromethyl-3-methyl-benzofuran-2-sulfonyl)-pyridazine. n-Butyl lithium (2.5 M in hexane, 4.2 mmol, 1.7 mL) was added dropwise over 15 minutes to a solution of 3-methyl-5-trifluoromethyl benzofuran (3.82 mmol, 765 mg) in THF (10 mL) cooled to −78° C. To this was added 2-fluorosulfonyl-4-methoxy-pyridazine (3.82 mmol, 734 mg) and stirred for 30 minutes. The reaction mixture was allowed to come to room temperature overnight and then quenched with EtOAc (20 mL) and H₂O (10 mL). The organic portion was collected, dried, filtered and the filtrate was evaporated to dryness to obtain a crude product, which was purified by silica gel chromatography (eluent:hexanes:EtOAc::3:1) to obtain the desired product, 3-methoxy-6-(5-trifluoromethyl-3-methyl-benzofuran-2-sulfonyl)-pyridazine (35%, 501 mg).

Step E: 6-(5-Trifluoromethyl-3-methyl-benzofuran-2-sulfonyl)-2H-pyridazin-3-one. A mixture of 3-methoxy-6-(5-trifluoromethyl-3-methyl-benzofuran-2-sulfonyl)-pyridazine (1.34 mmol, 500 mg), conc. HCl (2 mL), and dioxane (4 mL) was heated at 100° C. for 2 hours. The reaction mixture was cooled and evaporated to dryness. Water (10 mL) was added to the residue. The resulting white solid was collected and air dried to obtain the desired product: 6-(5-trifluoromethyl-3-methyl-benzofuran-2-sulfonyl)-2H-pyridazin-3-one (56%, 270 mg); mp 244° C.–245° C.

EXAMPLE 13

6-(5-Chloro-3-isopropyl-benzofuran-2-sulfonyl)-2H-pyridazin-3-one

Step A: 3-Methoxy-6-(5-chloro-3-isopropyl-benzofuran-2-sulfonyl)-pyridazine. n-Butyl lithium (2.5 M in hexane, 4.04 mmol, 1.62 mL) was added dropwise over 15 minutes to a solution of 5-chloro-3-isopropyl benzofuran (which was prepared as described in J. Am. Chem. Soc., 1950, 72, 5308,3.67 mmol, 715 mg) in THF (10 mL) cooled to −78° C. To this was added 2-fluorosulfonyl-4-methoxy-pyridazine (3.67 mmol, 706 mg) and the reaction mixture was stirred for 30 minutes. The reaction mixture was allowed to come to room temperature overnight and then quenched with EtOAc (20 mL) and H₂O (10 mL). The organic portion was collected, dried, filtered and the filtrate was evaporated to dryness to obtain a crude product, which was purified by silica gel chromatography (eluent:hexanes:EtOAc::4:1) to obtain the desired product: 3-methoxy-6-(5-chloro-3-isopropyl-benzofuran-2-sulfonyl)-pyridazine (21%, 283 mg).

Step B: 6-(5-Chloro-3-isopropyl-benzofuran-2-sulfonyl)-2H-pyridazin-3-one. A mixture of the above product (0.77 mmol, 283 mg), conc. HCl (1.5 mL), and dioxane (3 mL) was heated at 100° C. for 2 hours. The reaction was cooled and evaporated to dryness. The dried residue was triturated with water (10 mL), and filtered to obtain the desired product, 6-(5-chloro-3-isopropyl-benzofuran-2-sulfonyl)-2H-pyridazin-3-one. (79%, 215 mg); mp 211° C.–212° C.

EXAMPLE 14

6-(5-Fluoro-3-methyl-benzofuran-2-sulfonyl)-2H-pyridazin-3-one

Step A: (2-Acetyl-4-fluoro-phenoxy)-acetic acid. Chloroacetic acid (99.3 mmol, 9.4 g) was added to a suspension of 5-fluoro-2-hydroxy acetophenone (33.1 mmol, 5.1 g) in water (60 mL) containing sodium hydroxide (165.4 mmol, 6.6 g) and the reaction mixture was refluxed for 3.5 hours. The reaction mixture was cooled to room temperature, poured into a separatory funnel and the oily liquid at the bottom of the funnel was discarded. The aqueous top layer was collected, cooled to 0° C. and acidified with conc. HCl. The white precipitate was collected, and air died. The dry solid was crystallized from toluene to obtain (2-acetyl-4-fluoro-phenoxy)-acetic acid, (57%, 4.3 g).

Step B: 5-Fluoro-3-methyl benzofuran. Anhydrous sodium acetate (139.3 mmol, 11.4 g) was added to a solution of the title compound of Example 14, Step A (3.24 mmol, 1.6 g) in acetic anhydride (70 mL) and heated for 3 hours at 110° C. After cooling, the reaction mixture was poured into water (100 mL) and stirred for 1 hour. The aqueous solution was extracted with ether (2×100 mL), washed with 3% aqueous KOH (2×20 mL) and water (2×20 mL). The washed ether layer was collected, dried, filtered and the filtrate was evaporated to a brown residue, which was purified by silica gel chromatography (eluent:hexanes) to obtain the desired product, 5-fluoro-3-methyl benzofuran (59%, 1.77 mg).

Step C: 3-Methoxy-6-(5-fluoro-3-methyl-benzofuran-2-sulfonyl)-pyridazine. n-Butyl lithium (2.5 M in hexane, 11 mmol, 4.83 mL) was added dropwise over 15 minutes to a solution of 5-fluoro-3-methyl benzofuran (11 mmol, 1.65 mg) in THF (20 mL) cooled to −78° C. To this was added 3-fluorosulfonyl-6-methoxy-pyridazine (11 mmol, 2.11 g) and stirred for 30 minutes. The reaction mixture was allowed to come to room temperature overnight and was then quenched with EtOAc (40 mL) and H₂O (10 mL). The organic portion was collected, dried, filtered and the filtrate was evaporated to dryness to obtain a crude product, which was purified by silica gel chromatography (eluent:hexanes:EtOAc::4:1) to obtain the desired product: 3-methoxy-6-(5-fluoro-3-methyl-benzofuran-2-sulfonyl)-pyridazine (22%, 781 mg).

Step D: 6-(5-Fluoro-3-methyl-benzofuran-2-sulfonyl)-2H-pyridazin-3-one. A mixture of 3-methoxy-6-(5-fluoro-3-methyl-benzofuran-2-sulfonyl)-pyridazine (2.4 mmol, 775 mg), conc. HCl (1.5 mL), and dioxane (3 mL) was heated at 100° C. for 2 hours. The reaction mixture was cooled and evaporated to dryness. The dried residue was triturated with water (10 mL), and filtered to obtain the desired product, 6-(5-fluoro-3-methyl-benzofuran-2-sulfonyl)-2H-pyridazin-3-one (84%, 620 mg); mp 232° C.–233° C.

EXAMPLE 15

6-(6-Chloro-3-methyl-benzofuran-2-sulfonyl)-2H-pyridazin-3-one

The title compound of Example 15 was prepared from 4-chloro-2-hydroxy acetophenone in a manner analogous to the method of Example 14. mp>240° C.

EXAMPLE 16

6-(3-Hydroxy-benzofuran-2-sulfonyl)-2H-pyridazin-3-one

Step A: 3-Methoxy-6-(3-hydroxy-benzofuran-2-sulfonyl)-pyridazine. n-Butyl lithium (12 mmol, 4.7 mL) was added dropwise to a solution of diisopropyl amine (12 mmol, 1.7 mL) in THF (5 mL) at −78° C. After 10 minutes, a solution of 3-coumaranone (10 mmol, 1.92 g) in THF (10 mL) was added. The temperature was maintained at −78° C. and stirred for 10 minutes. To this was added a solution of 3-fluorosulfonyl-6-methoxy-pyridazine. The reaction mixture was brought to room temperature over one hour and quenched with ammonium chloride (1 g) and extracted with EtOAc (2×25 mL). The EtOAc extract was washed with $H_2O$, the organic layer was collected, dried, filtered and the filtrate was evaporated to a residue. This residue was purified by silica gel chromatography (eluent:hexanes:EtOAc::9:1) to yield 3-methoxy-6-(3-hydroxy-benzofuran-2-sulfonyl)-pyridazine (17%, 622 mg).

Step B: 6-(3-Hydroxy-benzofuran-2-sulfonyl)-2H-pyridazin-3-one. A mixture of 3-methoxy-6-(3-hydroxy-benzofuran-2-sulfonyl)-pyridazine (2.7 mmol, 820 mg), conc. HCl (2 mL), and dioxane (10 mL) was heated at 100° C. for 2 hours. The reaction mixture was cooled and evaporated to dryness. The dried residue was extracted with EtOAc (2×20 mL). The extract was dried, filtered, and the filtrate was evaporated to a residue, which was purified by silica gel chromatography (eluent:EtOAc:n-hexanes::3:1), triturated with water (10 mL), and filtered to obtain the desired product: 6-(3-hydroxy-benzofuran-2-sulfonyl)-2H-pyridazin-3-one (35%, 284 mg); mp 186° C.–189° C.

EXAMPLE 17

6-(5-Chloro-3-hydroxy-benzofuran-2-sulfonyl)-2H-pyridazin-3-one

The title compound of Example 17 was prepared from from 5-chloro-3-comaranone in place of 3-comaranone in a manner analogous to the method of Example 16. (22%); mp>240° C.

EXAMPLE 18

6-(5-Chloro-3-methyl-benzothiophene-2-sulfonyl)-2H-pyridazin-3-one

Step A: 3-Methoxy-6-(5-chloro-3-methyl-benzothiophene-2-sulfonyl)-pyridazine. n-Butyl lithium (2.5 M in hexane, 2.1 mmol, 0.84 mL) was added dropwise over 15 minutes to a solution of 5-chloro-3-methyl benzothiophene (1.91 mmol, 348 mg, which was prepared as described in J. Chem. Soc., 1965, 774–777), in THF (6 mL) cooled to −78° C. To this was added 2-fluorosulfonyl-4-methoxy-pyridazine (1.91 mmol, 366 mg) and stirred for 30 minutes. The reaction mixture was allowed to come to room temperature overnight and then quenched with EtOAc (20 mL) and $H_2O$ (10 mL). The organic portion was collected, dried, filtered and the filtrate was evaporated to dryness to obtain a crude product, which was purified by silica gel chromatography (eluent:hexanes:EtOAc::4:1) to obtain the desired product, 3-methoxy-6-(5-chloro-3-methyl-benzothiophene-2-sulfonyl)-pyridazine (29%, 197 mg).

Step B: 6-(5-Chloro-3-methyl-benzothiophene-2-sulfonyl)-2H-pyridazin-3-one. A mixture of 3-methoxy-6-(5-chloro-3-methyl-benzothiophene-2-sulfonyl)-pyridazine, (0.55 mmol, 197 mg), conc. HCl (1 mL), and dioxane (3 mL) was heated at 100° C. for 2 hours. The reaction mixture was cooled and evaporated to dryness. Water (10 mL) was added to the residue and the resulting yellow precipitate, 6-(5-chloro-3-methyl-benzothiophene-2-sulfonyl)-2H-pyridazin-3-one, was collected (29%, 55 mg); mp 258° C.–259° C.

EXAMPLE 19

6-(5-Methyl-benzothiophene-2-sulfonyl)-2H-pyridazin-3-one

The title compound of Example 19 was prepared from 5-methyl-benzothiophene in a manner analogous to the method of Example 18 (mp 240° C.–242° C.).

EXAMPLE 20

6-(Benzothiophene-2-sulfonyl)-2H-pyridazin-3-one

The title compound of Example 20 was prepared from benzothiophene in a manner analogous to the method of Example 18. mp 209° C.–210° C.

EXAMPLE 21

6-(3-Phenyl-benzofuran-2-sulfonyl)-2H-pyridazin-3-one

The title compound of Example 21 was prepared from 3-phenyl-benzofuran in a manner analogous to the method of Example 3. (65%); mp>220° C.

EXAMPLE 22

6-(3-[4-Fluorophenyl]-benzofuran-2-methylsulfonyl)-2H-pyridazin-3-one

The title compound of Example 22 was prepared from 4-fluorophenyl-benzofuran in a manner analogous to the method of Example 3. mp>240° C.

EXAMPLE 23

6-(Thieno[2,3b]pyridine-2-sulfonyl)-2H-pyridazin-3-one

Step A: 3-Methoxy-6-(thieno[2,3b]pyridine-2-sulfonyl)-pyridazine. n-Butyl lithium (2.5 M in hexane, 2.44 mmol, 0.97 mL) was added dropwise over 15 minutes to a solution of thieno[2,3b]pyridine (2.22 mmol, 300 mg, which was prepared according to International Patent Application Publication Number WO 005910), in THF (6 mL) cooled to −78° C. To this was added 2-fluorosulfonyl-4-methoxy-pyridazine (2.22 mmol, 426 mg) and stirred for 30 minutes. The reaction mixture was allowed to come to room temperature overnight and then quenched with EtOAc (20 mL) and $H_2O$ (10 mL). The organic portion was collected, dried, filtered and the filtrate was evaporated to dryness to obtain a crude product, which was purified by silica gel chromatography (eluent, EtOAc) to obtain the desired product, 3-methoxy-6-(thieno[2,3b]pyridine-2-sulfonyl)-pyridazine (24%, 166 mg).

Step B: 6-(Thieno[2,3b]pyridine-2-sulfonyl)-2H-pyridazin-3-one. A mixture of 3-methoxy-6-(thieno[2,3b]pyridine-2-sulfonyl)-pyridazine, without further purification, (0.54 mmol, 166 mg), conc. HCl (1 ML), and dioxane (3 mL) was heated at 100° C. for 2 hours. The reaction mixture was cooled and evaporated to dryness. Water (10 mL) was added to the residue, and sufficient solid $NaHCO_3$ was added to adjust the pH to 6. It was then extracted with CHCl₃ (2×20 mL), and the CHCl₃ layer was collected, dried, filtered and the filtrate was evaporated to a residue, which was purified by silica gel chromatography (eluent:EtOAc:MeOH::9:1) to yield 6-(thieno[2,3b]pyridine-2-sulfonyl)-2H-pyridazin-3-one: (29%, 30 mg); mp 225° C.–230° C.

EXAMPLE 23a 6-(Furano[2,3b]pyridine-2-sulfonyl)-2H-pyridazin-3-one

The title compound of Example 23a was prepared from furano[2,3b]pyridine in a manner analogous to the method of Example 23.

EXAMPLE 24

2-(6-Oxo-1,6-dihydro-pyridazine-3-sulfonyl)-5H-furo[3,2-c]pyridin-4-one

Step A: 3-Methoxy-6-(thieno[2,3b]pyridine-4-chloro-2-sulfonyl)-pyridazine. The title compound of Example 24, Step A was prepared from 4-chloro-thieno[2,3b]pyridine (which was prepared according to the method described in International Patent Application Publication Number WO00/59510) in a manner analogous to the method of Example 23.

Step B: 2-(6-Oxo-1,6-dihydro-pyridazine-3-sulfonyl)-5H-furo[3.2-c]pyridin-4-one. A mixture of 3-methoxy-6-(thieno[2,3b]pyridine-4-chloro-2-sulfonyl)-pyridazine (0.51 mmol, 157 mg), concentrated HCl (5 mL) and dioxane (3 mL) was heated at 100° C. overnight. The reaction mixture was cooled and evaporated to dryness. Water (10 mL) was added to the residue and the precipitated solid was collected to yield 53 mg of the title compound of Example 24. (35%); mp>275° C.

EXAMPLE 25

6-(5-Chloro-3-ethyl-benzofuran-2-sulfonyl)-2H-pyridazin-3-one

Step A: 4-Chloro-2-iodo phenol. To a solution of 4-chlorophenol in THF (75 mL), and H₂O (75 mL) was added a mixture of crushed iodine (78.7 mmol, 20 g) and sodium bicarbonate (78.7 mmol, 6.6 g). The reaction mixture was stirred at room temperature overnight, then quenched with sufficient 5% sodium thiosulfate solution to turn the color of the reaction mixture from deep violet to light yellow and extracted with ether (2×200 mL). The ether layer was collected, washed with H₂O, and the washed ether layer was dried, filtered and the filtrate was evaporated to a crude product, which was purified by distillation to obtain 4-chloro-2-iodo phenol (7%, 1.3 g); mp 79° C.–82° C.

Step B: 4-Chloro-2-iodo O-crotyl phenol. To a mixture of 4-chloro-2-iodo phenol (5.11 mmol, 1.3 g) in DMF (40 mL) and potassium carbonate (10 mmol, 1.4 g) was added crotyl bromide (10.2 mmol, 1.6 g) and the reaction mixture was stirred at room temperature for one hour. The reaction was quenched with H₂O (100 mL) and extracted with EtOAc (2×50 mL). The EtOAc layer was collected, dried, filtered and the filtrate was evaporated to obtain 4-chloro-2-iodo O-crotyl phenol (94%, 1.5 g).

Step C: 5-Chloro-3-ethyl-benzofuran. To a mixture of 4-chloro-2-iodo O-crotyl phenol (1.5 g, 4.86 mmol), sodium carbonate (12.2 mmol, 1.3 g), sodium formate (4.86 mmol, 330 mg), n-butyl ammonium chloride (5.34 mmol, 1.5 g) and DMF (10 mL) was added palladium di-acetate (0.24 mmol, 55 mg). The reaction was heated at 80° C. and maintained at that temperature overnight. After bringing the reaction to room temperature, the mixture was filtered. The filtrate was dried and evaporated to give a crude product, which was purified by silica gel chromatography (eluent:hexanes) to obtain 5-chloro-3-ethyl-benzofuran as a clear oil (60%, 530 mg).

Step D: 3-Methoxy-6-(5-chloro-3-ethyl-benzofuran-2-sulfonyl)-pyridazine. n-Butyl lithium (2.5 M in hexane, 3.2 mmol, 1.3 mL) was added dropwise over 15 minutes to a solution of 5-chloro-3-ethyl-benzofuran (2.88 mmol, 520 mg) in THF (8 mL) cooled to −78° C. To this was added 2-fluorosulfonyl-4-methoxy-pyridazine (2.88 mmol, 553 mg) and the reaction mixture was stirred for 30 minutes. The reaction mixture was allowed to come to room temperature overnight and then quenched with EtOAc (20 mL) and H₂O (10 mL). The organic portion was collected, dried, filtered and the filtrate was evaporated to dryness to obtain a crude product, which was purified by silica gel chromatography (eluent:hexanes:EtOAc::4:1) to obtain the desired product: 3-methoxy-6-(5-chloro-3-ethyl-benzofuran-2-sulfonyl)-pyridazine (35%, 352 mg).

Step E: 6-(5-Chloro-3-ethyl-benzofuran-2-sulfonyl)-2H-pyridazin-3-one. A mixture of 3-methoxy-6-(5-chloro-3-ethyl-benzofuran-2-sulfonyl)-pyridazine, without further purification, (1.04 mmol, 352 mg), conc. HCl (1.5 mL), and dioxane (3 mL) was heated at 100° C. for 2 hours. The reaction mixture was cooled and evaporated to dryness. Water (10 mL) was added to the residue and the resulting solid, 6-(5-chloro-3-ethyl-benzofuran-2-sulfonyl)-2H-pyridazin-3-one, was collected. (46%, 155 mg); mp 209° C.–210° C.

EXAMPLE 26

6-(Imidazo[1,2a]pyridine-3-sulfonyl)-2H-pyridazin-3-one

Step A: 6-(Imidazo[1,2a]pyridine-3-sulfonyl)-3-methoxy-pyridazine. n-Butyl lithium (2.5 M in hexane, 5 mmol, 2 mL) was added dropwise over 15 minutes to a solution of [1,2a]imidazopyridine (5 mmol, 590 mg) in THF (10 mL) cooled to −78° C. To this was added 3-fluorosulfonyl-6-methoxy-pyridazine (5 mmol, 960 mg) and the reaction mixture was stirred for 30 minutes. The reaction mixture was allowed to come to room temperature overnight and then quenched with EtOAc (20 mL) and H₂O (10 mL). The organic portion was collected, dried, filtered and the filtrate was evaporated to dryness to obtain a crude product, which was purified by silica gel chromatography (eluent:EtOAc) to obtain the desired product: 6-(imidazo[1,2a]pyridine-3-sulfonyl)-3-methoxy-pyridazine (8%, 121 mg).

Step B: 6-(Imidazo[1,2a]pyridine-3-sulfonyl)-2H-pyridazin-3-one. A mixture of 6-(imidazo[1,2a]pyridine-3-sulfonyl)-3-methoxy-pyridazine (0.341 mmol, 100 mg), conc. HCl (0.5 mL) and dioxane (5 mL) was heated at 100° C. for two hours. The reaction mixture was cooled and evaporated to dryness. Water (10 mL) was added to the residue, the pH adjusted to 7 and the resulting solid, 6-(imidazo[1,2a]pyridine-3-sulfonyl)-2H-pyridazin-3-one, was collected (72%, 67 mg); mp>240° C.

EXAMPLE 27

6-(Indole-2-sulfonyl)-2H-pyridazin-3-one

Step A: 3-Methoxy-6(N-phenylsulfonylindole-2-sulfonyl)-pyridazine. t-Butyl lithium (2.5M in hexane, 6.5 mmol, 4.3 mL) was added dropwise over 15 minutes to a solution of N-sulfonylphenyl indole (2.88 mmol, 520 mg) in tetrahydrofuran (8 mL) cooled to −78° C. To this was added 2-fluorosulfonyl-4-methoxypyridazine (5.2 mmol, 1.0 g) and stirred for 30 minutes. The reaction mixture was allowed to come to room temperature overnight and then quenched with EtOAc (20 mL) and $H_2O$ (10 mL). The organic portion was collected, dried, filtered and the filtrate was evaporated to dryness to obtain a crude product, which was purified by silica gel chromatography (eluent:hexanes:EtOAc::7:1) to obtain the desired product: 3-methoxy-6(N-phenylsulfonylindole-2-sulfonyl)-pyridazine (39%, 867 mg).

Step B: 2-Methoxy-6(indole-2-sulfonyl)-pyridazine. To a solution of sodium metal (18.6 mmol, 428 mg) dissolved in methanol (8 mL) was added a solution of 3-methoxy-6-(N-phenylsulfonylindole-2-sulfonyl)-pyridazine (1.86 mmol, 850 mg) and the reaction was stirred for 10 minutes. The reaction mixture was quenched with $H_2O$ (10 mL) and $CHCl_3$ (25 mL). The $CHCl_3$ layer was collected, dried, filtered, and the filtrate was evaporated to obtain 2-methoxy-6-(indole-2-sulfonyl)-pyridazine (82%, 440 mg).

Step C: 6-(Indole-2-sulfonyl)-2H-pyridazin-3-one. A mixture of-2-methoxy-6-(indole-2-sulfonyl)-pyridazine (1.03 mmol, 300 mg), conc. HCl (1 mL), and dioxane (6 mL) was heated at 100° C. for two hours. The reaction mixture was cooled and evaporated to dryness. Water (10 mL) was added to the residue and the resulting solid was triturated with methanol (2 mL) to yield 6-(indole-2-sulfonyl)-2H-pyridazin-3-one (37%, 106 mg); mp 248° C.–249° C.

EXAMPLE 28

6-(6-Chloro-indole-2-sulfonyl)-2H-pyridazin-3-one

The title compound of Example 28 was prepared from 6-chloro-N-p-tolylsulfonyl indole in a manner analogous to the method of Example 27. (95%); mp>250° C.

EXAMPLE 29

6-(5-Methoxy-indole-2-sulfonyl)-2H-pyridazin-3-one

The title compound of Example 29 was prepared from 5-methoxy-N-p-tolylsulfonyl indole in a manner analogous to the method of Example 27. (63%); mp>250° C.

EXAMPLE 30

6-(5-Chloro-indole-2-sulfonyl)-2H-pyridazin-3-one

The title compound of Example 30 was prepared from 5-chloro-N-p-tolylsulfonyl indole in a manner analogous to the method of Example 27. (64%); mp>250° C.

EXAMPLE 31

6-(6-Fluoro-indole-2-sulfonyl)-2H-pyridazin-3-one

The title compound of Example 31 was prepared from 6-fluoro-N-p-tolylsulfonyl indole in a manner analogous to the method of Example 27. (90%); mp>250° C.

EXAMPLE 32

6-(5,6-Methylenedioxy-indole-2-sulfonyl)-2H-pyridazin-3-one

The title compound of Example 32 was prepared from 5,6-methylenedioxy-N-p-tolylsulfonyl indole in a manner analogous to the method of Example 27. (67%).

EXAMPLE 33

6-(5,7-Dichloro-indole-2-sulfonyl)-2H-pyridazin-3-one

The title compound of Example 33 was prepared from 5,7-dichloro-N-p-tolylsulfonyl indole in a manner analogous to the method of Example 27. (80%); mp>250° C.

EXAMPLE 34

6-(7-Chloro-indole-2-sulfonyl)-2H-pyridazin-3-one

The title compound of Example 34 was prepared from 7-chloro-N-p-tolylsulfonyl indole in a manner analogous to the method of Example 27. (76%); mp 248–250° C.

EXAMPLE 35

6-(5-Chloro-3-phenyl-benzofuran-2-sulfonyl)-2H-pyridazin-3-one

The title compound of Example 35 was prepared from 5-chloro-3-phenyl-benzofuran in a manner analogous to the method of Example 27. mp>240° C.

EXAMPLE 36

6-(3-Chloro-indole-2-sulfonyl)-2H-pyridazin-3-one

Step A: 3-Methoxy-6-(3-chloro-indole-2-sulfenyl)-pyridazine. A mixture of 3-methoxy-6-(indole-2-sulfenyl)-pyridazine) (2.92 mmol, 750 mg), N-chloro-succinimide (2.92 mmol, 390 mg) and methanol (15 mL) was stirred overnight at room temperature. Excess methanol was removed and the residue was extracted with EtOAc (3×10 mL). The EtOAc extract was collected, dried, filtered and evaporated to dryness to obtain a residue, which was purified by silica gel chromatography (eluent:hexanes:EtOAc::19:5) to yield 3-methoxy-6-(3-chloro-indole-2-sulfenyl)-pyridazine (40%, 338 mg).

Step B: 3-Methoxy-6-(3-chloro-indole-2-sulfonyl)-pyridazine. A mixture of 3-methoxy-6-(3-chloro-indole-2-sulfenyl)-pyridazine (0.72 mmol, 210 mg), MCPBA (1.58 mmol, 385 mg) and $CHCl_3$ (20 mL) was stirred overnight at room temperature. The reaction mixture was diluted with $CHCl_3$ (20 mL), the $CHCl_3$ layer was collected and washed with 2N NaOH (2×5 mL). The washed $CHCl_3$ layer was collected, dried, filtered, and evaporated to dryness and the residue was purified by silica gel chromatography (eluent, $CHCl_3$) to yield 3-methoxy-6-(3-chloro-indole-2-sulfonyl)-pyridazine.

Step C: 6-(3-Chloro-indole-2-sulfonyl)-2H-pyridazin-3-one. A mixture of 3-methoxy-6-(3-chloro-indole-2-sulfonyl)-pyridazine (0.34 mmol, 110 mg), conc. HCl (1 mL), and dioxane (3 mL) was heated at 100° C. for 2 hours. The reaction mixture was cooled and evaporated to dryness. The dried residue was triturated with water (10 mL), and filtered to obtain 6-(3-chloro-indole-2-sulfonyl)-2H-pyridazin-3-one (99%, 108 mg); mp 250° C.

EXAMPLE 37

6-(N-Benzylindole-5-sulfonyl)-2H-pyridazin-3-one

Step A: 3-Methoxy-6-(N-benzylindole-5-sulfonyl)-2H-pyridazine. sec-Butyl lithium (1.3 M in hexane, 5.25 mmol, 4 mL) was added dropwise to a solution of N-benzyl-5-bromo indole (3.5 mmol, 1.0 g) in THF (5 mL) at −78° C. After 15 minutes, 2-fluorosulfonyl-4-methoxy-pyridazine (4.2 mmol, 808 mg) was added and the reaction mixture was stirred for 30 minutes. The reaction mixture was allowed to come to room temperature overnight and was then quenched with EtOAc (20 mL) and H$_2$O (10 mL). The organic portion was collected, dried, filtered and the filtrate was evaporated to dryness to obtain a crude product, which was purified by silica gel chromatography (eluent:hexanes:EtOAc::7:1) to obtain the desired product: 3-methoxy-6-(N-benzylindole-5-sulfonyl)-2H-pyridazine (19%, 258 mg).

Step B: 6-(N-Benzylindole-5-sulfonyl)-2H-pyridazin-3-one. A mixture of 3-methoxy-6-(N-benzylindole-5-sulfonyl)-2H-pyridazine (0.64 mmol, 245 mg), conc. HCl (0.5 mL), and dioxane (3 mL) was heated at 100° C. for 2 hours. The reaction mixture was cooled and evaporated to dryness. Water (10 mL) was added to the residue and the resulting solid, 6-(N-benzylindole-5-sulfonyl)-2H-pyridazin-3-one, was collected (55%, 102 mg).

EXAMPLE 38

6-(5-Chloro-3-methyl-benzofuran-2-methylsulfonyl)-2H-pyridazin-3-one

Step A: 5-Chloro-3-methyl benzofuran-2-carboxaldehyde. n-Butyl lithium (2.5 M in hexane, 6.6 mmol, 2.6 mL) was added dropwise over 15 minutes to a solution of 5-chloro-3-methyl benzofuran (6.0 mmol, 1 g) in THF (8 mL) cooled to −78° C. To this was added DMF (12 mmol, 0.6 mL) and stirred for one hour. The reaction mixture was allowed to come to room temperature overnight and then quenched with EtOAc (20 mL) and H$_2$O (10 mL). The organic portion, was collected, dried, filtered and the filtrate was evaporated to dryness to obtain 5-chloro-3-methyl benzofuran-2-carboxaldehyde (96%, 1.12 g), which was carried on without further purification.

Step B: 5-Chloro-3-methyl benzofuran 2-methanol. To a solution of 5-chloro-3-methyl benzofuran-2-carboxaldehyde (5.55 mmol, 1.08 g) in ethanol (25 mL) was added portionwise sodium borohydride (16.6 mmol, 630 mg). After one hour, the ethanol was evaporated and the residue was partitioned between CHCl$_3$ and H$_2$O. The CHCl$_3$ layer was collected, filtered, dried, and evaporated to dryness to obtain 5-chloro-3-methyl benzofuran 2-methanol (88%, 965 mg); mp 112° C.–113° C.

Step C: 2-Bromomethyl-5-chloro-3-methyl benzofuran. A solution of 5-chloro-3-methyl benzofuran 2-methanol (18.3 mmol, 3.6 g) in ether (200 mL) was cooled to 0° C. To this was added drop-wise phosphorus tribromide (29.3 mmol, 7.9 g) and then DMF (2 mL). After allowing the reaction mixture to come to room temperature over three hours, the reaction was quenched with ice water (100 mL). The ether layer was collected, dried, filtered and the filtrate was evaporated to a yellow solid: 2-bromomethyl-5-chloro-3-methyl benzofuran (88%, 4.2 g); mp 81° C.–82° C.

Step D: 3-Methoxy-6-(3-methyl-benzofuran-2-methylsulfenyl)-pyridazine. A solution of 2-mercapto-5-methoxy pyridazine (4.33 mmol, 750 mg) in DMF (5 mL) was added dropwise to a suspension of sodium hydride (60%, 4.7 mmol, 191 mg) in DMF (5 mL) cooled to 0° C. After 10 minutes, a solution of 2-bromomethyl-5-chloro-3-methyl benzofuran (2.9 mmol, 750 mg) in DMF (5 mL) was added to the reaction mixture. After two hours, the reaction mixture was quenched with water (100 mL) and extracted with EtOAc (2×50 mL). The EtOAc layer was collected, dried, filtered and the filtrate was evaporated to obtain a yellow solid: 3-methoxy-6-(3-methyl-benzofuran-2-methylsulfenyl)-pyridazine (97%, 906 mg).

Step E: 3-Methoxy-6-(3-methyl-benzofuran-2-methylsulfonyl)pyridazine. A mixture of 3-methoxy-6-(3-methyl-benzofuran-2-methylsulfenyl)-pyridazine (2.5 mmol, 800 mg), MCPBA (75%, 7.5 mmol, 1.7 g) and CHCl$_3$ (20 mL) was stirred at room temperature overnight. The reaction mixture was filtered and the filtrate was washed with H$_2$O (50 mL), and saturated sodium bicarbonate solution (10 mL). The CHCl$_3$ layer was collected, dried, filtered, and evaporated to dryness to obtain 3-methoxy-6-(3-methyl-benzofuran-2-methylsulfonyl)pyridazine (96%, 850 mg).

Step F: 6-(3-Methyl-benzofuran-2-methylsulfonyl)-2H-pyridazin-3-one. A mixture of 3-methoxy-6-(3-methyl-benzofuran-2-methylsulfonyl)-pyridazine (2.4 mmol, 850 mg), conc. HCl (1.5 mL), and dioxane (3 mL) was heated at 100° C. for two hours. The reaction mixture was cooled and evaporated to dryness. Water (10 mL) was added to the residue, the resulting solid was collected and triturated with hot isopropyl ether (55%, 102 mg). The precipitated white solid, 6-(3-methyl-benzofuran-2-methylsulfonyl)-2H-pyridazin-3-one, was collected (41%, 336 mg); mp 240° C.–241° C.

EXAMPLE 39

6-(Indole-3-sulfonyl)-2H-pyridazin-3-one

Step A: 3-Methoxy-6-(N-sulfonylphenyl-indole-3-sulfonyl)pyridazine. Ethyl magnesium bromide (1 M in THF, 1.8 mmol, 1.8 mL) was added to an ice cold solution of 3-iodo-N-sulfonylphenyl-indole (1.5 mmol, 575 mg, which was prepared according to Tetrahedron Letters 1998, 6849–6852) in THF (10 mL) and the reaction mixture was allowed to come to room temperature over 30 minutes. To this was added 3-fluorosulfonyl-6-methoxypyridazine (2.25 mmol, 192 mg) and the reaction mixture was stirred overnight at room temperature. The reaction mixture was quenched with H$_2$O (10 mL) and extracted with EtOAc (2×10 mL). The EtOAc extract was dried, filtered and the filtrate was evaporated to obtain a thick liquid, which was purified by silica gel chromatography (eluent:hexanes:EtOAc::3:1 to obtain 3-methoxy-6-(N-sulfonylphenyl-indole-3-sulfonyl)pyridazine (22%, 142 mg).

Step B: 3-Methoxy-6-(indole-3-sulfonyl)-pyridazine. To a solution of sodium metal (3 mmol, 70 mg) in methanol (1 mL) was added a solution of 3-methoxy-6-(N-sulfonylphenyl-indole-3-sulfonyl)pyridazine (0.3 mmol, 130 mg) in tetrahydrofuran (2 mL) and the reaction mixture was stirred at room temperature for 15 minutes. Cold water (5 mL) was added to the reaction mixture and extracted with ethyl acetate (2×10 mL) and the extract was dried, filtered and the filtrate was evaporated to dryness to obtain a residue, which was purified by silica gel chromatography (eluent:ethyl acetate:hexanes::1:1) to obtain 3-methoxy-6-(indole-3-sulfonyl)-pyridazine (90%); mass spectrum, m+, 289.

Step C: 6-(Indole-3-sulfonyl)-2H-pyridazin-3-one. The title compound of Example 39 was prepared from 3-methoxy-6-(indole-3-sulfonyl)pyridazine in a manner analogous to the method of Example 1. (76%); mp 248° C.–250° C.

EXAMPLE 40

6-(N-Methylindole-2-sulfonyl)-2H-pyridazin-3-one

Step A: 6-(Indole-N-methyl-2-sulfonyl)-3-methoxy-pyridazine. n-Butyl lithium (2.5 M in hexane, 0.83 mmol, 0.52 mL) was added dropwise over 15 minutes to a solution of 3-methoxy-6-(indole-2-sulfonyl)-pyridazine (0.69 mmol, 200 mg) in DMF (5 mL) cooled to −30° C. Methyl iodide (1.38 mmol, 0.1 mL) was added to the solution and the reaction mixture was stirred for another 10 minutes. The reaction mixture was quenched with H$_2$O (10 mL) and EtOAc (20 mL) and the EtOAc layer was collected, dried and evaporated to obtain 6-(indole-N-methyl-2-sulfonyl)-3-methoxy-pyridazine as pale yellow solid (97%, 203 mg).

Step B: 6-(N-Methylindole-2-sulfonyl)-2H-pyridazin-3-one. A mixture of 6-(indole-N-methyl-2-sulfonyl)-3-methoxy-pyridazine (6.6 mmol, 303 mg), concentrated HCl (0.5 mL), and dioxane (5 mL) was heated at 100° C. for 2 hours. The reaction was cooled and evaporated to dryness. Water (10 mL) was added to the residue and the resulting solid was collected to obtain 6-(N-methylindole-2-sulfonyl)-2H-pyridazin-3-one (87%, 166 mg); mp 233° C.–235° C.

EXAMPLE 41

6-(Pyrrole-1-sulfonyl)2H-pyridazin-3-one

Step A: 3-Methoxy-6-(pyrrole-1-sulfonyl)-pyridazine. To an ice-cold suspension of sodium hydride (1.86 mmol, 74 mg) in DMF (1 mL) was added a solution of pyrrole (1.86 mmol, 125 mg) in DMF (2 mL). To this was added 3-fluorosulfonyl-6-methoxypyridazine (1.55 mmol, 298 mg) and the reaction mixture was stirred overnight at room temperature. The reaction mixture was quenched with H$_2$O (20 mL) and EtOAc (20 mL) and the EtOAc layer was collected, dried, filtered and evaporated to a residue. The residue was purified by silica gel chromatography (eluent:hexanes:EtOAc::9:1) to obtain 3-methoxy-6-(pyrrole-1-sulfonyl)-pyridazine (30%, 112 mg).

Step B: 6-(Pyrrole-1-sulfonyl)-2H-pyridazin-3-one. A mixture of 3-methoxy-6-(pyrrole-1-sulfonyl)-pyridazine (0.46 mmol, 112 mg), conc. HCl (1 mL) and dioxane (3 mL) was heated at 100° C. for 2 hours. The reaction mixture was cooled and evaporated to dryness. Water (10 mL) was added to the residue and the resulting solid was collected to obtain 6-(pyrrole-1-sulfonyl)-2H-pyridazin-3-one (69%, 73 mg); mp 140° C.–145° C.

EXAMPLE 42

6-(Imidazole-1-sulfonyl)2H-pyridazin-3-one

The title compound of Example 42 was prepared from imidazole in a manner analogous to Example 41. (73%); mp 55° C.–60° C.

EXAMPLE 43

6-(Indole-1-sulfonyl)2H-pyridazin-3-one

The title compound of Example 43 was prepared from indole in a manner analogous to Example 41. (87%); mp 169–170° C.

EXAMPLE 44

6-(3-Chloro-indole-1-sulfonyl)2H-pyridazin-3-one

The title compound of Example 44 was prepared from 3-chloroindole in a manner analogous to Example 41. (73%); mp>220° C.

EXAMPLE 45

6-(3-Chloro-Indazole-1-sulfonyl)2H-pyridazin-3-one

The title compound of Example 45 was prepared from 3-chloro-indazole in a manner analogous to Example 41. (32%); mp 238° C.–239° C.

EXAMPLE 46

6-(3-Methyl-indole-1-sulfonyl)-2H-pyridazin-3-one

The title compound of Example 46 was prepared from 3-methyl-indole in a manner analogous to Example 41. (32%); mp>220° C.

EXAMPLE 47

6-(Tetrahydroquinoline-1-sulfonyl)-2H-pyridazin-3-one

Step A: 3-Methoxy-6-(tetrahydroquinoline-1-sulfonyl-pyridazine. A mixture of 3-fluorosulfonyl-6-methoxypyridazine (2 mmol, 384 mg) and tetrahydroquinoline (4 mmol, 532 mg) was heated at 140° C. for two hours. The reaction mixture was cooled, extracted with EtOAc (20 mL), and the EtOAc extract was dried, filtered and evaporated to obtain 3-methoxy-6-(tetrahydroquinoline-1-sulfonyl)-pyridazine (73%, 451 mg).

Step B: 6-(Tetrahydroquinoline-1-sulfonyl)-2H-pyridazin-3-one. A mixture of 3-methoxy-6-(tetrahydroquinoline-1-sulfonyl)-pyridazine (1.14 mmol, 112 mg), conc. HCl (2 mL), and dioxane (5 mL) was heated at 100° C. for two hours. The reaction mixture was cooled and evaporated to dryness. Water (10 mL) was added to the residue and extracted with EtOAc. The EtOAc extract was washed with water, collected, dried, filtered and the filtrate was evaporated to a residue, which was crystallized from ether to yield 6-(tetrahydroquinoline-1-sulfonyl)-2H-pyridazin-3-one (33%, 11 mg); mp 200° C.

EXAMPLE 48

6-(2,3-Tetrahydro-indole-1-sulfonyl)2H-pyridazin-3-one

The title compound of Example 48 was prepared from 2,3-tetrahydro-indole in a manner analogous to Example 47. (44%); mp>220° C.

EXAMPLE 49

6-(5-Chloro-3-methyl-benzofuran-2-sulfinyl)-2H-pyridazin-3-one

A mixture of 6-(5-chloro-3-methyl-benzofuran-2-sulfenyl)-2H-pyridazin-3-one (prepared according to the method of Example 2, Step B) (5.0 g, 17.0 mmol), peracetic acid (1.9 g, 25.0 mmol) and acetic acid (20 mL) was stirred at room temperature for two hours. The reaction mixture was quenched with ice-cold water (30 mL) and the precipitated solid was filtered. The solid residue was washed with water (2×10 mL) and then air-dried to obtain the title compound of Example 50 (3.55 g, 73%); mp 234° C.–236° C.

EXAMPLE 50

6-(5-Chloro-3-methyl-benzofuran-2-sulfonyl)-2H-pyridazin-3-one, Sodium Salt

To a solution of 6-(5-chloro-3-methyl-benzofuran-2-sulfonyl)-2H-pyridazin-3-one (2 mmol, 696 mg) in acetone (200 mL) was added powdered sodium hydroxide (2 mmol, 80 mg). After a precipitate formed in the clear solution, the solid was filtered off to obtain the title compound of Example 50 (90%, 628 mg). mp>260° C.

EXAMPLE 51

Protocol for Determination of Aldose Reductase Inhibition

Test compound (TC) solutions were prepared by dissolving TC in 20 μl 20% dimethylsulfoxide (DMSO) and diluting with 100 mM potassium phosphate buffer, pH 7.0, to various TC concentrations, typically ranging from 5 mM to 1 μM. A "zero TC" solution was prepared that started with only 20 μl DMSO (no TC).

The assay for aldose reductase activity was performed in a 96-well plate. Initiation of the reaction (with substrate) was preceded by a 10 minute pre-incubation at 24° C. of 200 μl 100 mM potassium phosphate buffer, pH 7.0, containing 125 μM NADPH and 12.5 nM human recombinant Aldose Reductase (Wako Chemicals, Inc., #547-00581) with 25 μl TC solution. The reaction was initiated by the addition of 25 μl 20 mM D-glyceraldehyde (Sigma, St. Louis). The rate of decrease in $OD_{340}$ was monitored for 15 minutes at 24° C. in a 340 ATTC Plate Reader (SLT Lab Instruments, Austria). Inhibition by TC was measured as the percentage decrease in the rate of NADPH oxidation as compared to a non-TC containing sample.

Preparation 1

3-Fluorosulfonyl-6-methoxypyridazine

Step A: 3-Mercapto-6-methoxy pyridazine. A mixture of 3-chloro-6-methoxy pyridazine (0.69 mol, 100 g), thiourea (1.38 mol, 105 g) and ethyl methyl ketone (1.8 L) was refluxed for 3 hours. The reaction was cooled and the supernatant was poured into water and extracted with 1M sodium hydroxide (4×100 mL). The sodium hydroxide solution was washed with EtOAc (2×50 mL), the aqueous extract was acidified with sufficient conc. HCl to lower the pH to 5 and the resulting yellow solid was collected and air-dried to obtain 3-mercapto-6-methoxy pyridazine (24%, 23 g); mp 198° C.–200° C.

Step B: 3-Fluorosulfonyl-6-methoxypyridazine. A mixture of 3-mercapto-6-methoxy pyridazine (50 mmol, 7.1 g), methanol (100 mL), water (100 mL) and potassium hydrogen fluoride (500 mmol, 39 g) was cooled to –10° C. and stirred for 30 minutes. Chlorine gas was bubbled into the reaction mixture at such a rate to ensure that the temperature of the reaction mixture did not rise above –10° C. The whitish-yellow reaction mixture was poured into ice-cold water (50 mL). The white solid was filtered and dried to afford 3-fluorosulfonyl-6-methoxypyridazine (74%, 7.1 g); mp 87° C.–88° C.

Preparation 2

3-Benzyloxy-6-fluorosulfonyl-pyridazine

Step A: 3-Benzyloxy-6-chloro-pyridazine. Sodium metal (130 mmol, 3.1 g) was added to benzyl alcohol (75 mL) and gently warmed to 50° C. for 30 minutes until all the sodium metal had dissolved. To this was added a solution of 3,6-dichloropyridazine (135 mmol) in benzyl alcohol (75 mL). The reaction was heated at 100° C. for 24 h. Excess benzyl alcohol was evaporated and the residue was extracted with EtOAc (3×100 mL). The EtOAc extract was washed with $H_2O$. The EtOAc layer was collected, dried, filtered and the filtrate was evaporated to yield 3-benzyloxy-6-chloro-pyridazine (90%, 26.7 g); mp 77° C.–78° C.

Step B: 3-Benzyloxy-6-mercapto-pyridazine. A mixture of 3-benzyloxy-6-chloro-pyridazine (18.2 mmol, 4 g), thiourea (36.3 mmol, 2.8 g) and ethyl methyl ketone (75 mL) was refluxed overnight. Excess ethyl methyl ketone was evaporated, the residue was extracted with 2M sodium hydroxide (25 mL) and the sodium hydroxide solution was washed with EtOAc (2×30 mL). The aqueous layer was collected and sufficient conc. HCl was added to bring the pH to 5 and extracted with EtOAc (2×30 mL). The EtOAc extract was collected, dried, filtered and the filtrate was evaporated to yield 3-benzyloxy-6-mercapto-pyridazine (15%, 605 mg); mp 155° C.–157° C.

Step C: 3-Benzyloxy-6-fluorosulfonyl-pyridazine. A mixture of 3-benzyloxy-6-mercapto-pyridazine (2.34 mmol, 510 mg), methanol (10 mL), water (1.0 mL), and potassium hydrogen fluoride (23.4 mmol, 1.83 g) was cooled to –10° C. and stirred for 30 minutes. Chlorine gas was bubbled into the mixture at a such rate to ensure that the temperature of the reaction mixture did not rise above –10° C. The whitish-yellow reaction mixture was poured into ice-cold water (50 mL) and the resulting white solid was filtered and air-dried to obtain 3-benzyloxy-6-fluorosulfonyl-pyridazine (89%, 560 mg). mp 85° C.–86° C.

Preparation 3

2-Methyl-5-trifluoromethyl benzofuran

The title compound of Preparation 3 was prepared by following the procedure described in Tetrahedron Letters, 1988, 29, 4687–4690.

Preparation 4

4-Fluorophenyl-benzofuran

To an ice-cold solution of 3-coumaranone (10 mmol, 1.34 g) in ether (20 mL) was added 4-fluoro-phenyl magnesium bromide (2 M in ether, 20 mmol, 10 mL) and the reaction stirred for 3.5 hours. The reaction was quenched with $H_2O$ (10 mL), the pH was adjusted to 7 with sufficient 10% HCl and extracted with ether (3×10 mL). The ether extract was collected, dried, filtered, and evaporated to dryness. The residue was purified by silica gel chromatography (eluent:hexanes) to obtain 4-fluorophenyl-benzofuran.

What is claimed is:

1. A compound of Formula I

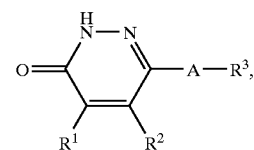

a prodrug thereof or a pharmaceutically acceptable salt of said compound or said prodrug, wherein:

A is S, SO or $SO_2$;

$R^1$ and $R^2$ are each independently hydrogen or methyl;

$R^3$ is $Het^1$, —$CHR^4Het^1$ or $NR^6R^7$;

$R^4$ is hydrogen or $(C_1-C_3)$alkyl;

$R^6$ is $(C_1-C_6)$alkyl, aryl or $Het^2$;

$R^7$ is $Het^3$;

$Het^1$ is pyridyl, pyrimidyl, pyrazinyl, pyridazinyl, quinolyl, tetrahydroquinolyl, isoquinolyl, quinazolyl, quinoxalyl, phthalazinyl, cinnolinyl, naphthyridinyl, pteridinyl, pyrazinopyrazinyl, pyrazinopyridazinyl, pyrimidopyridazinyl, pyrimidopyrimidyl, pyridopyrimidyl, pyridopyrazinyl, pyridopyridazinyl, pyrrolyl, furanyl, thienyl, imidazolyl, oxazolyl, thiazolyl, pyrazolyl, isoxazolyl, isothiazolyl, triazolyl, oxadiazolyl, thiadiazolyl, tetrazolyl, indolyl, tetrahydroindolyl, benzofuranyl, benzothienyl, benzimidazolyl, benzoxazolyl, benzothiazolyl, indazolyl, benzisoxazolyl, benzisothiazolyl, pyrrolopyridyl, furopyridyl, thienopyridyl, imidazolopyridyl, oxazolopyridyl, thiazolopyridyl, pyrazolopyridyl, isoxazolopyridyl, isothiazolopyridyl, pyrrolopyrimidyl, furopyrimidyl, thienopyrimidyl, imidazolopyrimidyl, oxazolopyrimidyl, thiazolopyrimidyl, pyrazolopyrimidyl, isoxazolopyrimidyl, isothiazolopyrimidyl, pyrrolopyrazinyl, furopyrazinyl, thienopyrazinyl, imidazolopyrazinyl, oxazolopyrazinyl, thiazolopyrazinyl, pyrazolopyrazinyl, isoxazolopyrazinyl, isothiazolopyrazinyl, pyrrolopyridazinyl, furopyridazinyl, thienopyridazinyl, imidazolopyridazinyl, oxazolopyridazinyl, thiazolopyridazinyl, pyrazolopyridazinyl, isoxazolopyridazinyl or isothiazolopyridazinyl; Het$^1$ is optionally substituted with up to a total of four substituents each independently selected from halo, formyl, $(C_1-C_6)$ alkoxycarbonyl, $(C_1-C_6)$alkylenyloxycarbonyl, $(C_1-C_4)$alkoxy-$(C_1-C_4)$alkyl, $C(OH)R^{12}R^{13}$, $(C_1-C_4)$ alkylcarbonylamido, $(C_3-C_7)$ cycloalkylcarbonylamido, phenylcarbonylamido, benzyl, phenyl, naphthyl, imidazolyl, pyridyl, triazolyl, benzimidazolyl, oxazolyl, isoxazolyl, thiazolyl, oxadiazolyl, thiadiazolyl, tetrazolyl, thienyl, benzothiazolyl, pyrrolyl, pyrazolyl, quinolyl, isoquinolyl, benzoxazolyl, pyridazinyl, pyridyloxy, pyridylsulfonyl, furanyl, phenoxy, thiophenoxy, $(C_1-C_4)$alkylsulfenyl, $(C_1-C_4)$alkylsulfonyl, $(C_3-C_7)$ cycloalkyl, $(C_1-C_6)$alkyl optionally substituted with up to three fluoro, or $(C_1-C_4)$alkoxy optionally substituted with up to five fluoro; said benzyl, phenyl, naphthyl, imidazolyl, pyridyl, triazolyl, benzimidazolyl, oxazolyl, isoxazolyl, thiazolyl, oxadiazolyl, thiadiazolyl, tetrazolyl, thienyl, benzothiazolyl, pyrrolyl, pyrazolyl, quinolyl, isoquinolyl, benzoxazolyl, pyridazinyl, pyridyloxy, pyridylsulfonyl, furanyl, phenoxy, thiophenoxy, in the definition of substituents for Het$^1$ are optionally substituted with up to three substituents independently selected from hydroxy, halo, hydroxy-$(C_1-C_4)$alkyl, $(C_1-C_4)$alkoxy-$(C_1-C_4)$alkyl, $(C_1-C_6)$alkylsulfenyl, $(C_1-C_6)$alkylsulfinyl, $(C_1-C_6)$alkylsulfonyl, $(C_1-C_6)$alkyl optionally substituted with up to five fluoro, and $(C_1-C_4)$alkoxy optionally substituted with up to five fluoro; said imidazolyl, oxazolyl, isoxazolyl, thiazolyl and pyrazolyl in the definition of substituents for Het$^1$ are optionally substituted with up to two substituents independently selected from hydroxy, halo, $C_1-C_4$) alkyl, hydroxy-$(C_1-C_4)$alkyl, $(C_1-C_4)$alkoxy-$(C_1-C_4)$ alkyl, $C_1-C_4$)alkyl-phenyl optionally substituted in the phenyl portion with one Cl, Br, OMe, Me or SO$_2$-phenyl wherein said SO$_2$-phenyl is optionally substituted in the phenyl portion with one Cl, Br, OMe, Me, $(C_1-C_4)$alkyl optionally substituted with up to five fluoro, or $(C_1-C_4)$alkoxy optionally substituted with up to three fluoro; $R^{12}$ and $R^{13}$ are each independently hydrogen or $(C_1-C_4)$alkyl;

Het$^2$ and Het$^3$ are each independently imidazolyl, pyridyl, triazolyl, benzimidazolyl, oxazolyl, isoxazolyl, thiazolyl, oxadiazolyl, thiadiazolyl, tetrazolyl, thienyl, benzothiazolyl, pyrrolyl, pyrazolyl, quinolyl, isoquinolyl, benzoxazolyl, pyridazinyl, pyridyloxy, pyridylsulfonyl, furanyl, phenoxy, thiophenoxy; Het$^2$ and Het$^3$ are each independently optionally substituted with up to a total of four substituents each independently selected from halo, formyl, $(C_1-C_6)$ alkoxycarbonyl, $(C_1-C_6)$alkylenyloxycarbonyl, $(C_1-C_4)$alkoxy-$(C_1-C_4)$alkyl, $C(OH)R^{18}R^{19}$, $(C_1-C_4)$ alkylcarbonylamido, $(C_3-C_7)$ cycloalkylcarbonylamido, phenylcarbonylamido, phenyl, naphthyl, imidazolyl, pyridyl, triazolyl, benzimidazolyl, oxazolyl, isoxazolyl, thiazolyl, oxadiazolyl, thiadiazolyl, tetrazolyl, thienyl, benzothiazolyl, pyrrolyl, pyrazolyl, quinolyl, isoquinolyl, benzoxazolyl, pyridazinyl, pyridyloxy, pyridylsulfonyl, furanyl, phenoxy, thiophenoxy, $(C_1-C_4)$alkylsulfenyl, $(C_1-C_4)$alkylsulfonyl, $(C_3-C_7)$ cycloalkyl, $(C_1-C_4)$alkyl optionally substituted with up to three fluoro or $(C_1-C_4)$alkoxy optionally substituted with up to five fluoro; said phenyl, naphthyl, imidazolyl, pyridyl, triazolyl, benzimidazolyl, oxazolyl, isoxazolyl, thiazolyl, oxadiazolyl, thiadiazolyl, tetrazolyl, thienyl, benzothiazolyl, pyrrolyl, pyrazolyl, quinolyl, isoquinolyl, benzoxazolyl, pyridazinyl, pyridyloxy, pyridylsulfonyl, furanyl, phenoxy, thiophenoxy, in the definition of substituents for Het$^2$ and Het$^3$ are optionally substituted with up to three substituents independently selected from hydroxy, halo, hydroxy-$(C_1-C_4)$alkyl, $(C_1-C_4)$ alkoxy-$(C_1-C_4)$alkyl, $(C_1-C_4)$alkyl optionally substituted with up to five fluoro and $(C_1-C_4)$alkoxy optionally substituted with up to five fluoro; said imidazolyl, oxazolyl, isoxazolyl, thiazolyl and pyrazolyl in the definition of substituents for Het$^2$ and Het$^3$ are optionally substituted with up to two substituents independently selected from hydroxy, halo, hydroxy-$(C_1-C_4)$ alkyl, $(C_1-C_4)$alkoxy-$(C_1-C_4)$alkyl, $(C_1-C_4)$alkyl optionally substituted with up to five fluoro and $(C_1-C_4)$alkoxy optionally substituted with up to three fluoro; and $R^{18}$ and $R^{19}$ are each independently hydrogen or $(C_1-C_4)$alkyl;

provided that when $R^3$ is $NR^6R^7$, then A is SO$_2$, with the proviso that 6-(5-chloro-3-methyl-benzofuran-2-sulfonyl)-2H-pyridazine-3-one and the pharmaceutically acceptable salts thereof is excluded, and further provided that when $R^1$ and $R^2$ are both hydrogen and $R^3$ is unsubstituted 2-pyridinyl, A is not SO.

2. A compound of claim 1, a prodrug thereof or a pharmaceutically acceptable salt of said compound or said prodrug, wherein A is SO$_2$; $R^1$ and $R^2$ are each hydrogen; $R^3$ is Het$^1$ optionally substituted with up to a total of four substituents.

3. A compound of claim 2, a prodrug thereof or a pharmaceutically acceptable salt of said compound or said prodrug, wherein Het$^1$ is 5H-furo-[3,2c]pyridin-4-one-2-yl, furano[2,3b]pyridin-2-yl, thieno[2,3b]pyridin-2-yl, indol-2-yl, indol-3-yl, benzofuran-2-yl, benzothien-2-yl, imidazo[1,2a]pyridin-3-yl, pyrrol-1-yl, imidazol-1-yl, indazol-1-yl, tetrahydroquinol-1-yl or tetrahydroindol-1-yl, wherein said Het$^1$ is optionally independently substituted with up to a total of two substituents each independently selected from fluoro, chloro, bromo, $(C_1-C_6)$alkyl, $(C_1-C_6)$alkoxy, trifluoromethyl, hydroxy, benzyl or phenyl; said benzyl and phenyl are each optionally independently substituted with up to three halo, $(C_1-C_6)$alkyl, $(C_1-C_6)$alkoxy, $(C_1-C_6)$ alkylsulfonyl, $(C_1-C_6)$alkylsulfinyl, $(C_1-C_6)$alkylsulfenyl, trifluoromethyl or hydroxy.

4. A compound of claim 3, a prodrug thereof or a pharmaceutically acceptable salt of said compound or said prodrug, wherein Het$^1$ is indol-2-yl, benzofuran-2-yl, benzothiophen-2-yl, furano[2,3b]pyridin-2-yl, thieno[2,3b] pyridin-2-yl or imidazo[1,2a]pyridin-4-yl, wherein said Het$^1$ is optionally independently substituted with up to a total of two substituents each independently selected from fluoro, chloro, bromo, ($C_1$–$C_6$)alkyl, ($C_1$–$C_6$)alkoxy, trifluoromethyl or phenyl; said phenyl being optionally substituted with up to two substituents independently selected from fluoro, chloro and ($C_1$–$C_6$)alkyl.

5. A compound of claim 4, a prodrug thereof or a pharmaceutically acceptable salt of said compound or said prodrug, wherein $Het^1$ is indol-2-yl or indol-3-yl, said indol-2-yl or indol-3-yl being optionally independently substituted with up to two substituents each independently selected from fluoro, chloro and methyl.

6. A compound of claim 5, a prodrug thereof or a pharmaceutically acceptable salt of said compound or said prodrug, wherein $Het^1$ is 5-chloro-indol-2-yl.

7. A compound of claim 5, a prodrug thereof or a pharmaceutically acceptable salt of said compound or said prodrug, wherein $Het^1$ is 5-fluoro-indol-2-yl.

8. A compound of claim 5, a prodrug thereof or a pharmaceutically acceptable salt of said compound or said prodrug, wherein $Het^1$ is indol-2-yl.

9. A compound of claim 5, a prodrug thereof or a pharmaceutically acceptable salt of said compound or said prodrug, wherein $Het^1$ is indol-3-yl.

10. A compound, a prodrug thereof or a pharmaceutically acceptable salt of said compound or said prodrug, selected from 6-(indole-2-sulfonyl)-2H-pyridazin-3-one, 6-(5-chloro-indole-2-sulfonyl)-2H-pyridazin-3-one, 6-(5-fluoro-indole-2-sulfonyl)-2H-pyridazin-3-one and 6-(indole-3-sulfonyl)-2H-pyridazin-3-one.

11. A compound of claim 4, a prodrug thereof or a pharmaceutically acceptable salt of said compound or said prodrug, wherein $Het^1$ is benzofuran-2-yl optionally substituted with up to two substituents each independently selected from methyl, methoxy, chloro, fluoro, ethyl, 4-fluorophenyl, trifluoromethyl, isopropyl, phenyl and hydroxy.

12. A compound of claim 11, a prodrug thereof or a pharmaceutically acceptable salt of said compound or said prodrug, wherein $Het^1$ is 5-chloro-benzofuran-2-yl, 5,7-dichloro-benzofuran-2-yl, benzofuran-2-yl, 5-fluoro-3-methyl-benzofuran-2-yl, 3-methyl-5-trifluoromethyl-benzofuran-2-yl, 5-chloro-3-phenyl-benzofuran-2-yl, 3-phenyl-benzofuran-2-yl, 3-(4-fluoro-phenyl)-benzofuran-2-yl, 5-chloro-benzofuran-2-yl and 3-ethyl-5-methyl-benzofuran-2-yl or 3-methyl-benzofuran-2-yl.

13. A compound of claim 11, a prodrug thereof or a pharmaceutically acceptable salt of said compound or said prodrug, wherein $Het^1$ is 3-methylbenzofuran-2-yl, optionally substituted with up to one additional substituent each independently selected from methyl, methoxy, chloro, fluoro, ethyl, 4-fluorophenyl, trifluoromethyl, isopropyl, phenyl and hydroxy.

14. A compound of claim 13, a prodrug thereof or a pharmaceutically acceptable salt of said compound or said prodrug, wherein said additional substituent is 5-fluoro.

15. A compound of claim 13, a prodrug thereof or a pharmaceutically acceptable salt of said compound or said prodrug, wherein said additional substituent is 5-trifluoromethyl.

16. A compound of claim 11, a prodrug thereof or a pharmaceutically acceptable salt of said compound or said prodrug, selected from 6-(5-fluoro-3-methyl-benzofuran-2-sulfonyl)-2H-pyridazin-3-one and 6-(5-trifluoromethyl-3-methyl-benzofuran-2-sulfonyl)-2H-pyridazin-3-one.

17. A compound of claim 4, a prodrug thereof or a pharmaceutically acceptable salt of said compound or said prodrug, wherein $Het^1$ is benzothien-2-yl optionally substituted with up to two substituents each independently selected from methyl and chloro.

18. A compound of claim 17, a prodrug thereof or a pharmaceutically acceptable salt of said compound or said prodrug, wherein $Het^1$ is benzothien-2-yl.

19. A compound of claim 17, a prodrug thereof or a pharmaceutically acceptable salt of said compound or said prodrug, wherein $Het^1$ is 5-chloro-3-methylbenzothien-2-yl.

20. A compound of claim 17, a prodrug thereof or a pharmaceutically acceptable salt of said compound or said prodrug, selected from 6-(5-chloro-3-methyl-benzothiophene-2-sulfonyl)-2H-pyridazin-3-one and 6-(benzothiophene-3-sulfonyl)-2H-pyridazin-3-one.

21. A compound of claim 1, a prodrug thereof or a pharmaceutically acceptable salt of said compound or said prodrug, wherein $R^3$ is $CHR^4Het^1$, said $Het^1$ being optionally substituted with up to a total of four substituents each independently selected from halo, formyl, ($C_1$–$C_6$) alkoxycarbonyl, ($C_1$–$C_6$)alkylenyloxycarbonyl, ($C_1$–$C_4$) alkoxy-($C_1$–$C_4$)alkyl, $C(OH)R^{12}R^{13}$, ($C_1$–$C_4$) alkylcarbonylamido, ($C_3$–$C_7$)cycloalkylcarbonylamido, phenylcarbonylamido, benzyl, phenyl, naphthyl, imidazolyl, pyridyl, triazolyl, benzimidazolyl, oxazolyl, isoxazolyl, thiazolyl, oxadiazolyl, thiadiazolyl, tetrazolyl, thienyl, benzothiazolyl, pyrrolyl, pyrazolyl, quinolyl, isoquinolyl, benzoxazolyl, pyridazinyl, pyridyloxy, pyridylsulfonyl, furanyl, phenoxy, thiophenoxy, ($C_1$–$C_4$)alkylsulfenyl, ($C_1$–$C_4$)alkylsulfonyl, ($C_3$–$C_7$)cycloalkyl, ($C_1$–$C_6$)alkyl optionally substituted with up to three fluoro, or ($C_1$–$C_4$) alkoxy optionally substituted with up to five fluoro; said benzyl, phenyl, naphthyl, imidazolyl, pyridyl, triazolyl, benzimidazolyl, oxazolyl, isoxazolyl, thiazolyl, oxadiazolyl, thiadiazolyl, tetrazolyl, thienyl, benzothiazolyl, pyrrolyl, pyrazolyl, quinolyl, isoquinolyl, benzoxazolyl, pyridazinyl, pyridyloxy, pyridylsulfonyl, furanyl, phenoxy, thiophenoxy, in the definition of substituents for $Het^1$ are optionally substituted with up to three substituents independently selected from hydroxy, halo, hydroxy-($C_1$–$C_4$)alkyl, ($C_1$–$C_4$)alkoxy-($C_1$–$C_4$)alkyl, ($C_1$–$C_6$)alkylsulfenyl, ($C_1$–$C_6$)alkylsulfinyl, ($C_1$–$C_6$)alkylsulfonyl, ($C_1$–$C_6$)alkyl optionally substituted with up to five fluoro and ($C_1$–$C_6$) alkoxy optionally substituted with up to five fluoro; said imidazolyl, oxazolyl, isoxazolyl, thiazolyl and pyrazolyl in the definition of substituents for $Het^1$ are optionally substituted with up to two substituents independently selected from hydroxy, halo, $C_1$–$C_6$)alkyl, hydroxy-($C_1$–$C_4$)alkyl, ($C_1$–$C_4$)alkoxy-($C_1$–$C_4$)alkyl, $C_1$–$C_4$)alkyl-phenyl optionally substituted in the phenyl portion with one Cl, Br, OMe, Me or $SO_2$-phenyl wherein said $SO_2$-phenyl is optionally substituted in the phenyl portion with one Cl, Br, OMe, Me, ($C_1$–$C_4$)alkyl optionally substituted with up to five fluoro, or ($C_1$–$C_4$)alkoxy optionally substituted with up to three fluoro; $R^{12}$ and $R^{13}$ are each independently hydrogen or ($C_1$–$C_4$)alkyl.

22. A compound of Formula I,

I a prodrug thereof or a pharmaceutically acceptable salt of said compound or said prodrug, wherein:

A is $SO_2$;

$R^1$ and $R^2$ are each independently selected from hydrogen and methyl;

R³ is Het¹;
Het¹ is indol-2-yl, indol-3-yl, benzofuran-2-yl, benzofuran-3-yl, benzothien-2-yl, benzothien-3-yl, imidazo[1,2a]pyridinyl, pyrrolyl, imidazolyl, indazolyl, tetrahydroquinolyl or tetrahydroindolyl, wherein said Het¹ is optionally independently substituted with up to a total of two substituents each independently selected from chloro, methyl, benzyl, methoxy, fluoro, 4-fluorophenyl, isopropyl, phenyl, trifluoromethyl, ethyl and hydroxy.

23. A compound of Formula I, a prodrug thereof or a pharmaceutically acceptable salt of said compound or said prodrug, wherein:

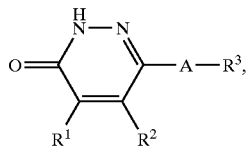

A is SO₂;
R¹ and R² are each independently selected from hydrogen and methyl;
R³ Het¹;
Het¹ is indol-2-yl or indol-3-yl, said indol-2-yl or indol-3-yl being optionally independently substituted with up to two substituents each independently selected from methyl, methoxy and chloro.

24. A compound of Formula I, a prodrug thereof or a pharmaceutically acceptable salt of said compound or said prodrug, wherein:

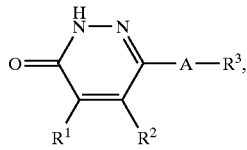

A is SO₂;
R¹ and R² are each independently selected from hydrogen and methyl;
R³ is Het¹;
Het¹ is benzofuran-2-yl, said benzofuran-2-yl being optionally independently substituted with up to two substituents each independently selected from methyl, methoxy, chloro, fluoro, ethyl, 4-fluorophenyl, trifluoromethyl, isopropyl, phenyl and hydroxy.

25. A compound selected from 6-(indole-2-sulfonyl)-2H-pyridazin-3-one; 6-(benzofuran-2-sulfonyl)-2H-pyridazin-3-one; 6-(5-methoxy-benzofuran-2-sulfonyl)-2H-pyridazin-3-one; 6-(3,5-dimethyl-benzofuran-2-sulfonyl)-2H-pyridazin-3-one; 6-(5,7-dichloro-benzofuran-2-sulfonyl)-2H-pyridazin-3-one; 6-(5-chloro-benzofuran-2-sulfonyl)-2H-pyridazin-3-one; 6-(3-methyl-benzofuran-2-sulfonyl)-2H-pyridazin-3-one; 6-(5-trifluoromethyl-3-methyl-benzofuran-2-sulfonyl)-2H-pyridazin-3-one; 6-(5-chloro-3-isopropyl-benzofuran-2-sulfonyl)-2H-pyridazin-3-one; 6-(5-fluoro-3-methyl-benzofuran-2-sulfonyl)-2H-pyridazin-3-one; 6-(6-chloro-3-methyl-benzofuran-2-sulfonyl)-2H-pyridazin-3-one; 6-(3-hydroxy-benzofuran-2-sulfonyl)-2H-pyridazin-3-one; 6-(5-chloro-3-hydroxy-benzofuran-2-sulfonyl)-2H-pyridazin-3-one; 6-(5-chloro-3-methyl-benzothiophene-2-sulfonyl)-2H-pyridazin-3-one; 6-(5-methyl-benzothiophene-2-sulfonyl)-2H-pyridazin-3-one; 6-benzothiophene-2-sulfonyl)-2H-pyridazin-3-one; 6-(3-phenyl-benzofuran-2-sulfonyl)-2H-pyridazin-3-one; 6-(3-[4-fluorophenyl]-benzofuran-2-methylsulfonyl)-2H-pyridazin-3-one; 6-(thieno[2,3b]pyridine-2-sulfonyl)-2H-pyridazin-3-one; 2-(6-oxo-1,6-dihydro-pyridazine-3-sulfonyl)-5H-furo[3.2-c]pyridin-4-one; 6-(5-chloro-3-ethyl-benzofuran-2-sulfonyl)-2H-pyridazin-3-one; 6-(imidazo[1,2a]pyridine-3-sulfonyl)-2H-pyridazin-3-one; 6-(6-chloro-indole-2-sulfonyl)-2H-pyridazin-3-one; 6-(5-methoxy-indole-2-sulfonyl)-2H-pyridazin-3-one; 6-(5-chloro-indole-2-sulfonyl)-2H-pyridazin-3-one; 6-(6-fluoro-indole-2-sulfonyl)-2H-pyridazin-3-one; 6-(5,6-methylenedioxy-indole-2-sulfonyl)-2H-pyridazin-3-one; 6-(7-chloro-indole-2-sulfonyl)-2H-pyridazin-3-one; 6-(5-chloro-3-phenyl-benzofuran-2-sulfonyl)-2H-pyridazin-3-one; 6-(3-chloro-indole-2-sulfonyl)-2H-pyridazin-3-one; 6-(N-benzylindole-5-sulfonyl)-2H-pyridazin-3-one; 6-(5-chloro-3-methyl-benzofuran-2-methylsulfonyl)-2H-pyridazin-3-one; 6-(indole-3-sulfonyl)-2H-pyridazin-3-one; 6-(N-methylindole-2-sulfonyl)-2H-pyridazin-3-one; 6-(pyrrole-1-sulfonyl)2H-pyridazin-3-one; 6-(imidazole-1-sulfonyl)2H-pyridazin-3-one; 6-(indole-1-sulfonyl)2H-pyridazin-3-one; 6-(3-chloro-indole-1-sulfonyl)2H-pyridazin-3-one; 6-(3-chloro-indazole-1-sulfonyl)2H-pyridazin-3-one; 6-(3-methyl-indole-1-sulfonyl)-2H-pyridazin3one; 6-(tetrahydroquinoline-1-sulfonyl)-2H-pyridazin-3-one; 6-(3-[4-fluorophenyl]-benzofuran-2-sulfonyl)-2H-pyridazin-3-one; 6-(imidazo[1,2a]pyridine-4-sulfonyl)-2H-pyridazin-3-one and 6-(2,3-tetrahydro-indole-1-sulfonyl)2H-pyridazin-3-one.

26. A compound of claim 25 selected from 6-(indole-2-sulfonyl)-2H-pyridazin-3-one; 6-(benzofuran-2-sulfonyl)-2H-pyridazin-3-one; 6-(5,7-dichloro-benzofuran-2-sulfonyl)-2H-pyridazin-3-one; 6-(5-chloro-benzofuran-2-sulfonyl)-2H-pyridazin-3-one; 6-(3-methyl-benzofuran-2-sulfonyl)-2H-pyridazin-3-one; 6-(5-trifluoromethyl-3-methyl-benzofuran-2-sulfonyl)-2H-pyridazin-3-one; 6-(5-fluoro-3-methyl-benzofuran-2-sulfonyl)-2H-pyridazin-3-one; 6-(3-hydroxy-benzofuran-2-sulfonyl)-2H-pyridazin-3-one; 6-(5-chloro-3-methyl-benzothiophene-2-sulfonyl)-2H-pyridazin-3-one; 6-benzothiophene-2-sulfonyl)-2H-pyridazin-3-one; 6-(3-[4-fluorophenyl]-benzofuran-2-sulfonyl)-2H-pyridazin-3-one; 6-(thieno[2,3b]pyridine-2-sulfonyl)-2H-pyridazin-3-one; 6-(5-chloro-3-ethyl-benzofuran-2-sulfonyl)-2H-pyridazin-3-one; 6-(5-chloro-indole-2-sulfonyl)-2H-pyridazin-3-one; 6-(5-chloro-3-phenyl-benzofuran-2-sulfonyl)-2H-pyridazin-3-one; 6-(5-chloro-3-methyl-benzofuran-2-methylsulfonyl)-2H-pyridazin-3-one; 6-(indole-3-sulfonyl)-2H-pyridazin-3-one; 6-(furano[2,3b]pyridine-2-sulfonyl)-2H-pyridin-3-one; 6-(5-methyl-benzofuran-2-sulfonyl)-2H-pyridazin-3-one; and 6-(imidazo[1,2a]pyridine-4-sulfonyl)-2H-pyridazin-3-one.

27. A compound of claim 26 selected from 6-(benzofuran-2-sulfonyl)-2H-pyridazin-3-one; 6-(5,7-dichloro-benzofuran-2-sulfonyl)-2H-pyridazin-3-one; 6-(5-chloro-benzofuran-2-sulfonyl)-2H-pyridazin-3-one; 6-(3-methyl-benzofuran-2-sulfonyl)-2H-pyridazin-3-one; 6-(5-trifluoromethyl-3-methyl-benzofuran-2-sulfonyl)-2H-pyridazin-3-one; 6-(5-fluoro-3-methyl-benzofuran-2-sulfonyl)-2H-pyridazin-3-one; 6-(5-chloro-3-methyl-benzothiophene-2-sulfonyl)-2H-pyridazin-3-one; 6-benzothiophene-2-sulfonyl)-2H-pyridazin-3-one; 6-(3-[4-fluorophenyl]-benzofuran-2-sulfonyl)-2H-pyridazin-3-one; 6-(5-chloro-3-ethyl-benzofuran-2-sulfonyl)-2H-pyridazin- 3-one; 6-(5-chloro-3-phenyl-benzofuran-2-sulfonyl)-2H-pyridazin-3-one; and 6-(5-methyl-benzofuran-2-sulfonyl)-2H-pyridazin-3-one.

28. A compound of claim 27 selected from 6-(5-trifluoromethyl-3-methyl-benzofuran-2-sulfonyl)-2H-pyridazin-3-one; and 6-(5-fluoro-3-methyl-benzofuran-2-sulfonyl)-2H-pyridazin-3-one.

29. A pharmaceutical composition comprising a compound of claim 1, a prodrug thereof or a pharmaceutically acceptable salt of said compound or said prodrug, and a pharmaceutically acceptable vehicle, carrier or diluent.

30. A compound of claim 1 wherein A is S or SO; $R^1$ and $R^2$ are each H; and $R^3$ is $Het^1$ or a pharmaceutically acceptable salt thereof.

31. A compound of claim 30 wherein A is S and $Het^1$ is 5H-furo-[3,2c]pyridin-4-one-2-yl, furano[2,3b]pyridin-2-yl, thieno[2,3b]pyridin-2-yl, indol-2-yl, indol-3-yl, benzofuran-2-yl, benzothien-2-yl, imidazo[1,2a]pyridin-3-yl, pyrrol-1-yl, imidazol-1-yl, indazol-1-yl, tetrahydroquinol-1-yl or tetrahydroindol-1-yl, wherein said $Het^1$ is optionally independently substituted with up to a total of two substituents each independently selected from fluoro, chloro, bromo, $(C_1-C_6)$alkyl, $(C_1-C_6)$alkoxy, trifluoromethyl, hydroxy, benzyl and phenyl; said benzyl and phenyl are each optionally independently substituted with up to three halo, $(C_1-C_6)$alkyl, $(C_1-C_6)$alkoxy, $(C_1-C_6)$alkylsulfonyl, $(C_1-C_6)$alkylsulfinyl, $(C_1-C_6)$alkylsulfenyl, trifluoromethyl or hydroxy, or a pharmaceutically acceptable salt thereof.

32. A compound of claim 31 wherein $Het^1$ is indol-2-yl, benzofuran-2-yl or benzothien-2-yl, wherein said $Het^1$ is optionally independently substituted with up to a total of two substituents each independently selected from fluoro, chloro, bromo, $(C_1-C_6)$alkyl, $(C_1-C_6)$alkoxy, trifluoromethyl, hydroxy, benzyl and phenyl; said benzyl and phenyl are each optionally independently substituted with up to three halo, $(C_1-C_6)$alkyl, $(C_1-C_6)$alkoxy, $(C_1-C_6)$alkylsulfonyl, $(C_1-C_6)$alkylsulfinyl, $(C_1-C_6)$alkylsulfenyl, trifluoromethyl or hydroxy, or a pharmaceutically acceptable salt thereof.

33. A compound of claim 32 wherein $Het^1$ is 5-chloro-3-methyl-benzofuran-2-yl or a pharmaceutically acceptable salt thereof.

34. 6-(5-Chloro-3-methyl-benzofuran-2-sulfenyl)-2H-pyridazin-3-one.

35. A compound of claim 30 wherein A is SO and $Het^1$ is 5H-furo-[3,2c]pyridin-4-one-2-yl, furano[2,3b]pyridin-2-yl, thieno[2,3b]pyridin-2-yl, indol-2-yl, indol-3-yl, benzofuran-2-yl, benzothien-2-yl, imidazo[1,2a]pyridin-3-yl, pyrrol-1-yl, imidazol-1-yl, indazol-1-yl, tetrahydroquinol-1-yl or tetrahydroindol-1-yl, wherein said $Het^1$ is optionally independently substituted with up to a total of two substituents each independently selected from fluoro, chloro, bromo, $(C_1-C_6)$alkyl, $(C_1-C_6)$alkoxy, trifluoromethyl, hydroxy, benzyl and phenyl; said benzyl and phenyl are each optionally independently substituted with up to three halo, $(C_1-C_6)$alkyl, $(C_1-C_6)$alkoxy, $(C_1-C_6)$alkylsulfonyl, $(C_1-C_6)$alkylsulfinyl, $(C_1-C_6)$alkylsulfenyl, trifluoromethyl or hydroxy, or a pharmaceutically acceptable salt thereof.

36. A compound of claim 35 wherein $Het^1$ is indol-2-yl, benzofuran-2-yl or benzothien-2-yl, wherein said $Het^1$ is optionally independently substituted with up to a total of two substituents each independently selected from fluoro, chloro, bromo, $(C_1-C_6)$alkyl, $(C_1-C_6)$alkoxy, trifluoromethyl, hydroxy, benzyl and phenyl; said benzyl and phenyl are each optionally independently substituted with up to three halo, $(C_1-C_6)$alkyl, $(C_1-C_6)$alkoxy, $(C_1-C_6)$alkylsulfonyl, $(C_1-C_6)$alkylsulfinyl, $(C_1-C_6)$alkylsulfenyl, trifluoromethyl or hydroxy, or a pharmaceutically acceptable salt thereof.

37. A compound of claim 36 wherein $Het^1$ is 5-chloro-3-methyl-benzofuran-2-yl.

38. 6-(5-Chloro-3-methyl-benzofuran-2-sulfinyl)-2H-pyridazin-3-one.

39. A method of inhibiting the activity of aldose reductase in a mammal in need of inhibition of the activity of aldose reductase comprising administering an aldose reductase activity inhibiting amount of a compound of claim 1.

40. A method of inhibiting the activity of aldose reductase in a mammal in need of inhibition of the activity of aldose reductase comprising administering a pharmaceutical composition of claim 29.

41. A method for treating cardiac tissue ischemia in a mammal comprising administering to said mammal an effective amount of a compound of claim 1, a prodrug thereof or a pharmaceutically acceptable salt thereof.

42. A method for treating cardiac tissue ischemia in a mammal comprising administering to said mammal an effective amount of a pharmaceutical composition of claim 29.

43. A method for treating one or more diabetic complications in a mammal suffering from one or more diabetic complications comprising administering to said mammal an effective amount of a pharmaceutical composition of claim 29.

44. A method for treating one or more diabetic complications in a mammal suffering from one or more diabetic complications comprising administering to said mammal an effective amount of a compound of claim 1, a prodrug thereof or a pharmaceutically acceptable salt of said compound or said prodrug.

45. A method of claim 44 wherein said diabetic complication is diabetic neuropathy.

46. A method of claim 44 wherein said diabetic complication is diabetic nephropathy.

47. A method of claim 44 wherein said diabetic complication is diabetic cardiomyopathy.

48. A method of claim 44 wherein said diabetic complication is diabetic retinopathy.

49. A method of claim 44 wherein said diabetic complication is cataracts.

50. A method of claim 44 wherein said diabetic complication is foot ulcers.

51. A method of claim 44 wherein said diabetic complication is diabetic macroangiopathy.

52. A method of claim 44 wherein said diabetic complication is diabetic microangiopathy.

* * * * *